US012678189B2

(12) United States Patent (10) Patent No.: US 12,678,189 B2
Vetter et al. (45) Date of Patent: *Jul. 14, 2026

(54) EXCISIONAL DEVICES AND METHODS

(71) Applicant: TransMed7, LLC, Portola Valley, CA (US)

(72) Inventors: James W Vetter, Portola Valley, CA (US); Paul A Vetter, Portola Valley, CA (US); Eugene H Vetter, Portola Valley, CA (US)

(73) Assignee: Transmed7, LLC, Portola Valley, CA (US)

( * ) Notice: Subject to any disclaimer, the term of this patent is extended or adjusted under 35 U.S.C. 154(b) by 114 days.

This patent is subject to a terminal disclaimer.

(21) Appl. No.: 18/822,319

(22) Filed: Sep. 2, 2024

(65) Prior Publication Data

US 2025/0160880 A1 May 22, 2025

Related U.S. Application Data

(63) Continuation of application No. 18/081,298, filed on Dec. 14, 2022, now Pat. No. 12,178,468, which is a
(Continued)

(51) Int. Cl.
*A61B 17/3207* (2006.01)
*A61B 5/00* (2006.01)
(Continued)

(52) U.S. Cl.
CPC ...... *A61B 17/32075* (2013.01); *A61B 5/0036* (2018.08); *A61B 5/0066* (2013.01);
(Continued)

(58) Field of Classification Search
CPC ........ A61B 17/32075; A61B 17/22031; A61B 17/320758; A61B 2017/22069;
(Continued)

(56) References Cited

U.S. PATENT DOCUMENTS 5,174,300 A 12/1992 Bales et al.
5,251,641 A 10/1993 Xavier
(Continued)

FOREIGN PATENT DOCUMENTS

EP 2196155 A2 6/2010
EP 3829450 B1 11/2023

OTHER PUBLICATIONS

BD EleVation Breast Biopsy System Quick Reference Guide © 2019 BD. All rights reserved. BD-10898 (6 pages).
(Continued)

*Primary Examiner* — Tuan V Nguyen
(74) *Attorney, Agent, or Firm* — YOUNG LAW FIRM, P.C.

(57) ABSTRACT

A platform device for material excision or removal from vascular structures for either handheld or stereotactic table or robotics platform use may comprise a work element or elements configured to selectively open and close at least one articulable beak or scoopula configured to penetrate and remove intra-vascular materials or obstructions or follow a central lumen of another device or over a wire in a longitudinal direction. Flush and vacuum tissue transport mechanisms may be incorporated as well as single or multiple arrays of image guidance elements, directional elements, ablation elements and other interventional assistance elements. A single tube or an inner sheath and an outer sheath which may be co-axially disposed relative to a work element may be configured to actuate a beak or beaks or scoopulas and provisions for simultaneous or differential beak or scoopula closing under their differential rotation may be incorporated.

10 Claims, 73 Drawing Sheets

Related U.S. Application Data continuation of application No. 16/840,715, filed on Apr. 6, 2020, now Pat. No. 11,596,436.

(60) Provisional application No. 62/829,187, filed on Apr. 4, 2019.

(51) Int. Cl.
*A61B 8/12* (2006.01)
*A61B 17/22* (2006.01)

(52) U.S. Cl.
CPC .............. *A61B 5/0084* (2013.01); *A61B 8/12* (2013.01); *A61B 17/22031* (2013.01); *A61B 17/320758* (2013.01); *A61B 2017/22038* (2013.01); *A61B 2017/22069* (2013.01)

(58) Field of Classification Search
CPC ........ A61B 2017/22038; A61B 5/0066; A61B 5/0084; A61B 8/12
See application file for complete search history.

(56) References Cited

U.S. PATENT DOCUMENTS

| | | | |
|---|---|---|---|
| 5,415,169 A | 5/1995 | Siczek et al. | |
| 5,526,822 A | 6/1996 | Burbank | |
| 5,873,886 A | 2/1999 | Larsen et al. | |
| 6,139,508 A | 10/2000 | Simpson et al. | |
| 2002/0165580 A1 | 11/2002 | Zwiefel et al. | |
| 2003/0032955 A1 | 2/2003 | Mulier | |
| 2003/0125639 A1 | 7/2003 | Fisher et al. | |
| 2003/0208153 A1* | 11/2003 | Stenzel .............. | A61B 17/3417 |
| | | | 604/60 |
| 2004/0230157 A1 | 11/2004 | Perry et al. | |
| 2005/0070885 A1 | 3/2005 | Nobis et al. | |
| 2005/0209564 A1 | 9/2005 | Bonner et al. | |
| 2006/0004323 A1 | 1/2006 | Chang | |
| 2006/0205992 A1 | 9/2006 | Lubock et al. | |
| 2007/0249999 A1 | 10/2007 | Sklar et al. | |
| 2007/0282197 A1 | 12/2007 | Bill et al. | |
| 2008/0015466 A1 | 1/2008 | Lerman | |
| 2008/0167524 A1 | 7/2008 | Goldwasser et al. | |
| 2009/0287114 A1* | 11/2009 | Lee .................... | A61B 10/0266 |
| | | | 600/564 |
| 2010/0049162 A1 | 2/2010 | Hameed | |
| 2010/0121153 A1 | 5/2010 | To | |
| 2010/0168610 A1 | 7/2010 | Lacombe et al. | |
| 2011/0060188 A1 | 3/2011 | Sharon et al. | |
| 2011/0245725 A1 | 10/2011 | Flatland et al. | |
| 2013/0041256 A1 | 2/2013 | Flebig | |
| 2013/0096459 A1 | 4/2013 | Vetter | |
| 2014/0180079 A1 | 6/2014 | Brown | |
| 2014/0213932 A1 | 7/2014 | Knoll et al. | |
| 2016/0089208 A1 | 3/2016 | Vetter et al. | |
| 2016/0287223 A1 | 10/2016 | Hingston et al. | |
| 2016/0367311 A1 | 12/2016 | Gerrans | |
| 2017/0020554 A1 | 1/2017 | Vetter | |
| 2019/0254649 A1 | 8/2019 | Walters et al. | |
| 2020/0214661 A1 | 7/2020 | Tropello | |

OTHER PUBLICATIONS

BD EleVation Breast Biopsy Value Analysis Brief, © 2021 BD. All rights reserved. 0921/6110 BD-27449 2797 (8 pages).

Mammotome Breast Biopsy System ST EX MR, © 2012 Devicor Medical Products, Inc. MDM 12-0016 (11 pages).

Finesse Ultra Breast Biopsy System Ultrasound Guided Breast Biopsy Technical Guide.

© Copyright C. R. Bard, Inc., 2009. All Rights Reserved. S11704-0 (2 pages).

Boston Scientific Radial Jaw 4 Single Use Biopsy Forceps, © 2016 Boston Scientific Corporation or its affiliates. ENDO-392404-AA Jun. 2016 (2 pages).

Comprehensive Review Mammotome Elite tetherless Vacuum-Assisted Biopsy System, Kimberly C. Hutcherson, MD / North Metropolitan Radiology Associates, LLP Northside Gwinnett Breast Center / Northside Hospital Gwinnett / Lawrenceville, GA 30046, © 2023 Devicor Medical Products, Inc. MDM# 210526 Rev 10/23.

David S. Zimmon, MD et al., Endoscopic multiple biopsy and rapid diagnosis by in situ fixation and histopathologic processing, www.giejournal.org vol. 86, No. 2 : 2017 Gastrointestinal Endoscopy 333-342 (10 pages).

Anwarul Islam, A New Single-Use Bone Marrow Biopsy Needle with Core Retention Design, Sci & Tech Res| BJSTR. MS.ID. 003294, DOI: 10.26717/BJSTR.2019.19.003294 (7 pages).

Hologic, Breast Biopsy Solutions, PB-00884 Hologic Inc. © 2021 All rights reserved. Hologic (7 pages).

Diversatek Healthcare GIJaw Single Use Biopsy Forceps, © 2018 Diversatek, Inc. | All Rights Reserved. 080-0073 08/18 (2 pages).

* cited by examiner

EXCISIONAL DEVICES AND METHODS

BACKGROUND

Embodiments relate to medical devices and methods. More particularly, embodiments relate to hand-held or mounted, manually or robotically guided, single or multiple insertion, single or multiple excisional and interventional devices and corresponding methods for vascular imaging, evaluation, clearing, restoration and regenerative applications. Embodiments further relate to improvements over currently used acute and chronic total and subtotal vessel occlusion removal or interventional systems, specifically in providing minimally invasive and more widely capable, reliable cardio-vascular excisional and interventional devices and methods.

SUMMARY

Embodiments are drawn to various medical devices and methods that may be used for intra-vascular interventional procedures and in any area of the body where tissue removal or therapeutic procedures are needed for diagnostic and therapeutic purposes. Many of the embodiments herein are drawn to vascular applications, however embodiments are likewise applicable to many other tubular areas including pulmonary, central and peripheral neural spaces, including the spinal canal, genitourinary spaces, bone marrow spaces and other areas of soft and hard tissue excisions or interventions throughout the body, including where the embodiments themselves create temporary or permanent spaces for access, restoration of channels that have been obliterated by diseases and other processes such as natural healing processes. An important aspect of embodiments is to include, in a portable way, chambers to aid imaging where they may be used in areas where, without such portability, clarity of imaging may be distorted or impeded altogether. Several embodiments combine excision and delivery with integrated imaging capabilities, which provides a means for bringing all needed capabilities to a site in some cases far removed from the manipulating mechanisms. According to one embodiment, an excisional device may be configured to remove liquids, solids, semi-solids and single or multiple material samples during a single insertion through the skin (percutaneous) into any vascular area of the body where such a targeted interventional site may be found. Embodiments may comprise structures and functionality for different phases of a multi-phase vascular clearing or restoration or regenerative procedure, whose stages, though of necessarily altered steps, may equally apply to several other areas of the body, whether tubular or non-tubular in anatomic structure, and which may be performed by hand, by robotic manipulation or by device attachment to a specialized imaging table stage or Magnetic Resonance Imaging (MRI) stage whether manually controlled, fully automated or a combination of the two. Embodiments may also be partially or fully manipulated and operated remotely using robotic mechanisms that may be fully guided by an operator and may be enhanced by machine learning, interpretive imaging, post-processing and other adaptive intelligence enhancements or systems that may provide virtual structures from raw input data, which may further be refined as a result of multi-source shared inputs, data compression, data analysis and data logic techniques or processes. These refinements and information analyses may in turn be used to further refine which of the mechanical, imaging and other features and components described herein may be subtracted as a result of information thus gained, paired and further analyzed in the context of pathology and clinical outcomes results. Embodiments may also comprise devices configured for insertion through the central lumen of another compatible excisional or interventional device. Embodiments of a device, along with associated related subcomponents described herein, may provide the capability to retrieve solid, contiguous and/or fragmented materials as well as liquid and semi-solid tissues for analysis, diagnosis and treatment, and to exhibit improvements in functionality and performance relative to present devices and methods for clearing chronic total occlusions and other vascular anomalies. Although some embodiments find particular utility in cardio-vascular intervention procedures, other embodiments also find utility in, for instance, urologic and gynecologic applications, as well as various endoscopic (flexible scopes inserted into various hollow organs) interventions—and are not limited therefore to vascular applications described, shown and claimed herein. Embodiments and elements thereof may be deployed in interventional procedures in coronaries, including bypass vessels (veins, internal mammary arteries, free radial grafts and in the case of peripheral vessels, synthetic grafts, native and bypass peripheral vessels including carotid arteries, renals, iliacs, femorals and distal vessels including venous and arterial vessels in various locations). Embodiments may include atherectomy and thrombectomy devices (those that remove plaque and other components of diseased vessel walls), which also contain a subset that may be used to treat both acute and chronic thromboembolic lesions and another subset that may be used to remove restenotic "scar" tissue obstructions (intimal hyperplasia); chronic total occlusion devices, which include a variety of devices some of which may be considered variants of atherectomy devices and finally, delivery devices to deliver medications, implants, stem cells, scaffolding or stents and devices such as other interventional devices performing functions listed above including use of laser energy, radiofrequency energy and others to ablate or otherwise alter pathophysiology of lesions that may contain calcific inclusions such as old plaque, areas of injury and healing as well as intimal and neo-intimal hyperplasia in native vessels, bypass vessels and implanted structures such as stents whether permanent or temporary, as well to be used, in various embodiments, as guiding elements including catheters and various types of guiding and interventional wires, imaging catheters and wires, contrast media, oxygenation elements, sensing instruments, radiation delivery elements, protective and shielding devices, downstream safety devices, high frequency ultrasound, high frequency pulsed lasers, and radiofrequency ablation devices among others. Embodiments may be configured to be fully or partially portable, disposable or reusable and may be, for example, electrically/electronically-, mechanically-, hydraulically-, pneumatically-, magnetically-, remotely and/or manually-powered, controlled and operated.

DETAILED DESCRIPTION

Figure 1:
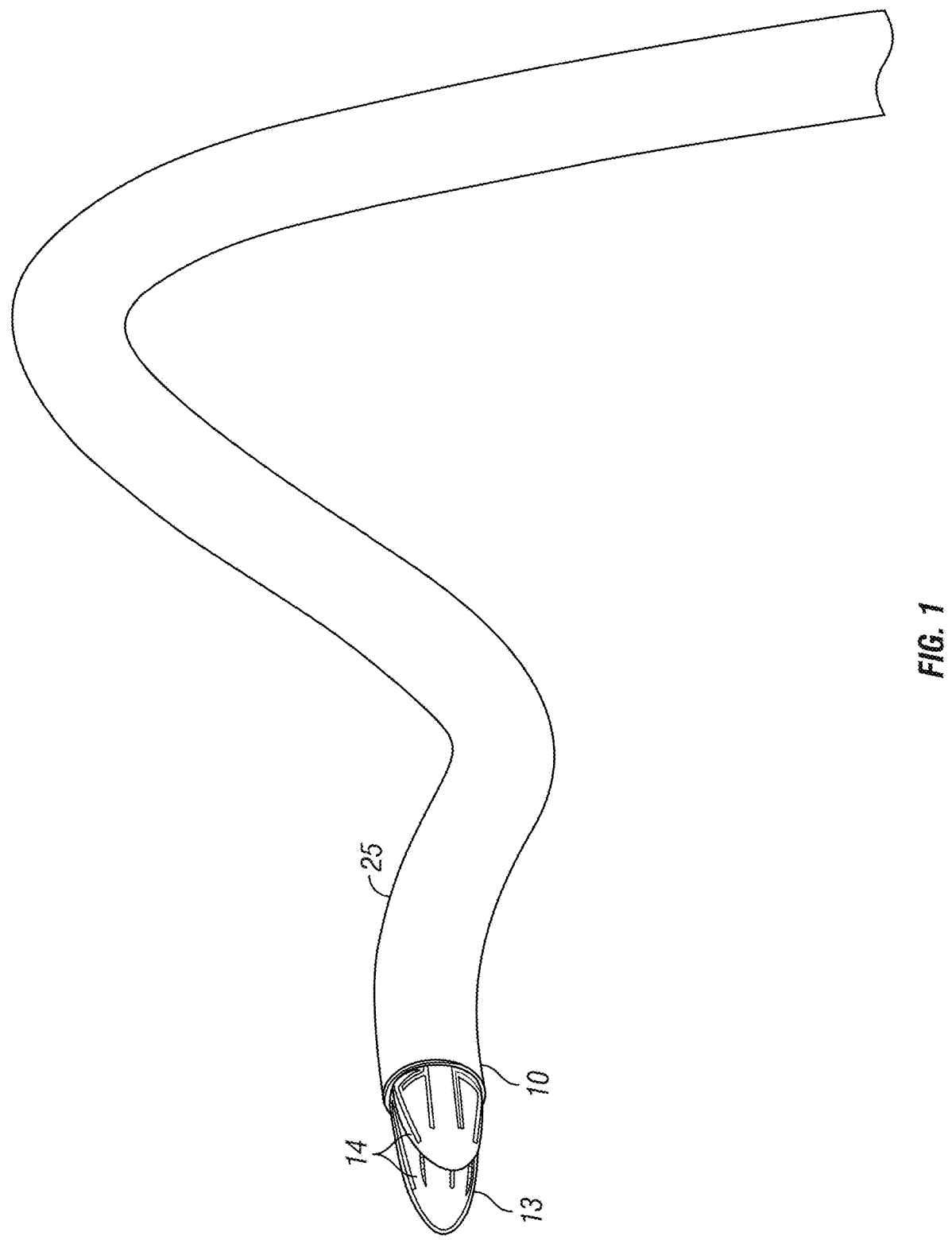
FIG. 1 is a perspective side view of a work element and its flexible shaft comprising an excisional device, according to one embodiment.

Reference will now be made in detail to the construction and operation of implementations of the embodiments illustrated in the accompanying drawings. The following description is only exemplary of the embodiments described and shown herein. The embodiments, therefore, are not limited to these implementations, but may be realized by other implementations. Indeed, although the figures are variously described as showing "an embodiment" or characterized as being "according to embodiments", all of the structures and associated functionalities may be present in a single device or one or more of the structures and associated functionalities may be omitted from one device or present in another device. Alternatively, some of the structures and functionalities shown and described herein may be included in some devices according to one or more embodiments, while other structures and functionalities shown and described herein may be included in in or more other devices according to embodiments. Similarly, the acts or steps shown and described herein may form a single embodiment of a single method or some acts or steps may be added or omitted in other sequences to form one or more embodiments of one or more other disclosed methods.

According to embodiments, a device for material or tissue excision may be configured to remove intra-vascular materials, whether totally occluding a vessel or subtotally occluding vessels and may comprise a range of work element dimensions ranging from, for example, approximately 0.002" to 0.249" diameter (⅓ French to 19 French), or other appropriate dimensions both larger and smaller depending on applications and field of use requirements. According to embodiments, an excisional device may comprise a single tube or a single tube at least partially disposed within a coaxially-disposed or non-coaxially disposed outer tube or tubes, which outer tube or tubes may include other non- or coaxially disposed additional tubes attached to or co-extruded therewith and may comprise or include a fixed or removable distal scoopula(s) or beak(s). A work element may comprise one or more scoopulas and/or one or more beaks, as well as one or more blade elements. Such scoopula(s) and/or beak(s) may be fixed or articulable, sharpened or unsharpened at their tips or along their side axes, and combinations of the two may be interchanged, according to embodiments. In the case of either articulable beaks or scoopulas, the principles of action as described herein and according to embodiments may be similar or different to that used for one relative to the other.

Herein, beaks may refer to that portion of a work element whose primary functions may comprise coring, shaving, penetrating with or without coring, dissecting, widening, isolating areas generally, articulating for purposes of positioning, shielding, isolating delivering agents or other components such as imaging equipment, guiding wires or tubes, inflatables or sensing equipment, or for retrieving liquids, solids or semi-solids and therefor may also be fixed, articulable, sharpened or unsharpened, and may have various features and shapes according to various embodiments. Beaks may comprise longitudinal living hinge elements such that the beaks may be expanded "out of round" to a more flattened shape, or alternatively to a different shape than when at rest. A beak driving assembly or assemblies in the device may have operating characteristics and features to enable rotational speeds advantageously to be chosen to optimize "sweep" ultrasound imaging using mechanical array or at a different speed to increase the information provided with phased array imaging, for example and may include longitudinal and "off angle" sweep capabilities as they are articulated to "shine" ultrasound or light energy at various structures of interest. These capabilities can also be used to receive signals in return and/or for reference signal processing. These capabilities can also be used together with "light out, sound in" systems that combine light and sound efferent and afferent signal processing to increase information available using a combination of these modalities. These rotational, longitudinal "pullback" and angular speeds may be generally in the same range as useful cutting, pullback/advancement and angular speeds associated with a desired interventional procedure, or they may be outside that normal range and activated separately for diagnostic or other therapeutic procedures (radiation delivery, medication "painting", injecting or other delivery).

A driving assembly or assemblies (hereafter, collectively "driving assembly" for ease of reference) for beaks may be controllable at the handle end of the device (e.g., proximally and outside the body) and can be quite sophisticated, reusable and electronically optimized for torque, rotational speed (rpm) and frequency (in the cases of translation, angular changes and oscillation motions). The driving assembly may also comprise variable control as needed and may also include the ability to halt work element motions at a part-off phase (a phase at which a cut or cored piece of tissue is separated from surrounding tissue), with automated rearward (proximal) translation for purposes of delivering excised materials (e.g., pieces of tissue) to a transport portion of the device where, according to one embodiment, vacuum along with fluid management flows and swirling action may complete the rearward delivery (for example, into a serial collection magazine or receptacle of the device). According to embodiments herein, driving mechanisms may also include delivery of electrical, mechanical, radiant, ultrasonic, electromagnetic, electron beam and simple magnetic, among other, energies distally to a work element in a desired target work area, whereby conversion or re-conversion to another energy form may be made in the work area. As examples, electrical energy may be delivered to a receiving electromagnetic device to mechanically actuate a distal element, or turbine power generated may be transmitted distally via inert gases or mechanical spinning of elements acting directly on a distal element or simply via fluids that may be present or introduced in the presence of spinning elements of a device according to embodiments, that may function to both create vacuum at the distal work element area while also creating mechanical motion in another or the same element, such as a high speed, low torque rotational element, such that simultaneous dissolution and sucking of debris such as clotted blood or particulate matter rearward and safely out of the work area may be accomplished. Yet another example is that an e-beam sent distally may be directionally guided or influenced by elements in the work area in which case energy may be precisely redirected and focused by embodiments herein, rather than merely converted to another form of energy per se. Multiple energies such as "light in, sound out" technologies among others, combining more than one modality to interrogate an area and supply more detailed information based on the modalities utilized in such a combination may be, at the same time, delivered, received and in some cases advantageously altered by elements of the present embodiments.

Energized excisional elements may refer to high energy, focused ultrasound, laser energies and other forms of energies capable of disrupting, dis-attaching, vaporizing, dissolution, or other modalities to remove from a site, or break down into small enough particles that may be easily cleared naturally, components of obstructing lesions, including, as shown in various figures that follow, the use of a plurality of such devices as may be required for specific applications of such energy delivery devices, according to embodiments herein.

In general, a scoopula may be a portion of the work element or elements of the device or may be a separate structure from the primary work element. A scoopula may be characterized by an elongated portion of its morphology and may have among its principle functions to define and/or isolate a work area within a vascular structure, and may for that purpose be fixed or articulable, with sharpened or unsharpened edges, and with a variety of shapes, according to various embodiments. Another principal function of a scoopula or multiple scoopulas may be to lead the way for following work elements, owing to the extreme streamlining of the structure such that areas to which access is difficult may be readily accessed due to the shape of the scoopula. Once in place, a scoopula may then be configured to deliver other work elements to perform their own functions, while the scoopula may continue to form a stable base from which to operate within a more defined space as a result. In that way, a scoopula structure may also be thought of as a protective element that may be cycled between closed-end or, in its more natural resting shape for example, as an open-ended element, yet capable of functioning as a directing device. In one embodiment, the scoopula may for example, refer to a beak element in combination with an elongated half-round cutout section (not necessarily exactly "half" of the whole tubular section) where a portion of a tubular section proximal to a beak element has part of its wall removed, as described and shown herein, and according to various embodiments. Additionally, both scoopulas and beaks may be primarily designated for rotation at low speeds. In other embodiments, beaks may be configured for rotation at speeds varying, for example, from 1 revolution per minute (RPM) to several thousand RPM.

A scoopula may perform functions that are the same or similar to the functions discharged by the beak or beaks. Indeed, according to one embodiment, a first scoopula may isolate a portion of a work area while a second scoopula may isolate a part of a work area in concert with the first scoopula, and either may be used to core or shave materials as though it or they were a beak or beaks. Another work element having articulable beaks, according to one embodiment, may be configured to capture and remove materials in the thus isolated work area. In this manner, an operator need not be limited to using a beak versus a scoopula at any stage of an intervention, based on the demands of the operation, including for example specific functions or vascular anatomic limitations for which one or the other may be better suited, to be performed and the objectives to be achieved with the present device and the elements of and accessories thereto. In the case of imaging equipment delivery, a scoopula may be used to adjust the scope, elevation, rotation, direction and distance to a target for the particular imaging modality, as well as for an excisional or other penetrating element, including guiding wires, micro-catheters, energy delivery devices, including ablative and dissolution devices and also imaging elements including imaging catheters and imaging guiding wires. This function could be quite useful particularly when imaging modalities utilizing higher frequencies and shorter penetration capabilities might otherwise be out of their range, according to embodiments. As shown herein, a transparent, expandable imaging element may serve by limiting absorption or distortion, to "transfer" or project a capability to image and visualize structures that may otherwise be beyond the reach of imaging frequencies or power specific to such a modality, a case in point being the enlargement of depth available to optical coherence tomography, by providing a near field that is relatively distortion and absorption free. Additionally, a chamber such as illustrated in the figures and described in the present disclosure, could exclude the unwanted absorption of light as a consequence of blood for example in a vascular structure, where such a chamber could be utilized together with a supporting element that would permit blood flow around such a supporting element and also around such an imaging chamber. In this way, downstream flow may be permitted while at the same time imaging fields between and imaging element and areas of interest can proceed without the absorption due to blood flow. Likewise, when certain imaging or sensing equipment may need to operate in a blood free environment, a fixed or an articulating scoopula with or without an additional sealing element such as an inflatable cuff, could function to lessen the need for flushing fluids, by fully or partially isolating an area of interest from contamination of the image by blood for example. This isolation capability could also provide for a stable volume from which to clear and aspirate intravascular disease materials such as clotted blood, both fresh and aged, as well as particulate material from intimal disease such as plaque materials or various combinations of several of these frequently encountered materials including debris that may form as a consequence of a clearing, shaving or other intervention. In the case of an expandable cuff element, as well as a plurality of expandable elevating elements, perfusion could be controlled to a minimum level to prevent downstream tissue damage or even minimal levels of temporary ischemia for example.

Embodiments of devices comprising variations of scoopula(s) may be configured to isolate the working surface(s) from the flow surfaces of a vessel. According to methods herein, in use in a vascular lumen, for example, this means that in the lumen and/or potential lumen (tight stenoses and complete occlusions, whether chronic or acute) a targeted workspace will be established and protected before and additionally as soon as there is sufficient space to permit blood flow, immediately upon improvement in flow channels as a result of removal of obstructing materials. Such elements may likewise permit providing gently forced flow for the purposes of downstream oxygenation and nutrition, introduction of imaging equipment while minimizing ischemic time and also quickly enhancing natural flows based on driving pressures relieved by new or widened lumens. The lumen space may be isolated from the working space so that any elements that are released during removal actions may also be prevented from impairing flow in the protected flow lumen of the vessel being widened in caliber. This space may then be utilized such that vacuum may be maximized in the working side of the vessel as defined by the scoopula, and also in certain embodiments, while protecting the flow side. For example, according to methods, an embodiment may simultaneously press against the wall on the flow side (opposite to the working side) causing the working side of a catheter to be pressed against the lesion side of the vessel so that the elements on the working side of a device may be held precisely at the desired depth (for example for removing as much or little of a lesion as may be optimal for various considerations such as transport, degree of aggressiveness, rate of removal, particulate size of the material being removed, as the working beak element(s) are given purchase). Embodiments may also provide a stable, (geometrically) straight reference platform. This reference platform may be used to straighten a desired segment of a vessel such that a uniform depth of lesion material may be safely removed without the concern for asymmetrically removing deep-wall elements (for example in an otherwise naturally or as a result of disease, tortuous section of a vessel) that may lead to weakening, aneurism formation or even perforation during the procedure, according to methods and embodiments herein.

Thus, according to one embodiment, the scoopula may serve as an isolating element, as a reference platform, as a delivery platform permitting downstream element introduction, as a stabilizing element and as a preventer of distal embolization. A living hinge or hinges may be defined in one or more portions of the scoopula. These living hinges or locally elastically deformable regions may include straight longitudinal (axial) curved longitudinal (spirals, complex diagonals, etc.,) and crossways configurations, as defined by kerfs cut into the tube from which the scoopula may be constructed. Embodiments may utilize any of these for example, depending on particular function, desired radius and degree of flexion and/or deflection, for use in specific vascular anatomic considerations among other considerations (whether or not more than one scoopula is used for example), according to methods. Such configurations may enable expansion, variable, controllable rigidity, and geometry changes that enable tailored cuts that function as tip deflections, as well as for the purpose of temporary or permanent vessel expansion, the resultant forces of which may advantageously be directed in a radial direction, and scaffolding prior to stenting implant procedures or as stand-alone therapeutic procedures such as angioplasty of vessels, advantageously without the inherent strength limitations and non-directional expansion (radially) of typical balloon angioplasty technologies.

Advantageously, distal flow around and/or through such structures may be less restrictive than balloon-based technologies that occupy the entire cross-section of a vessel such as an artery, according to embodiments. Even when, in certain cases, very narrow spaces for distal flows are provided in specialized balloon devices, these are significantly limited in practical application and make these devices necessarily bulkier and harder to maneuver as a consequence. In contrast, according to embodiments and methods herein, flow rates can be significantly higher based on expansion elements free of such relatively thicker material and inflation materials. These configurations may also be used to enhance isolation and flow control on the proximal and distal ends of the isolation (working, non- or restricted-flow) chamber. The sides of a scoopula may also be controllable with these living hinges to enhance working chamber isolation control. The back side of a scoopula may be configured to enable pressing the working side against the obstructive material. Such urging may be carried out with, for example, incorporated elements of the scoopula such as pontoon-type inflatables, struts that are themselves living hinge elements, and/or may be a portion of the existing beak-actuating tendons or may be separate elements, and/or may include structural living hinge portions that change the effective caliber and or geometrical configuration(s) of the device work element or distal tip such that pressure may be applied in the direction opposite the obstructive material direction within a vascular structure. Cuts for spiral(s), lateral expansions (longitudinal scoopula living hinge(s)), and combinations of the above may all be incorporated into the scoopula or scoopulas, according to embodiments.

One embodiment is a device comprising two co-axially-disposed work elements. Whether a work element comprises one or more scoopulas or beaks, or combinations thereof, two or more co-axially placed work elements (referred to herein as a complex work element) may have particular advantages with regard to cutting or coring efficiencies in certain tissue types or with certain obstruction matrices. For example, a first work element or portion thereof, may be configured as a tubular structure ending in a fixed or articulable scoopula. A second work element may be co-axially placed inside or outside of the first work element and may comprise one or more articulable beaks. According to one embodiment, the beak driving assembly and the scoopula driving assembly (which may be one and the same) may differentially rotate the first and second work elements such that the beak or beaks of the first work element may be driven in rotation at a first speed and/or direction and the scoopula or scoopulas of the second work element may be driven in rotation at a second rotational speed and/or direction that may be different from the first rotational speed and/or direction. In such an embodiment, open beaks may be extended distally along the length of the scoopula, and the beaks rotating differentially (at different speeds or in different directions, relatively) may create a shearing action between edges of the beak(s) and the sides of the scoopula(s), for example. Additionally, as the beaks are extended distally up to and even beyond the end of the extended portion of the scoopula(s), the scoopula(s) may serve as a tissue or obstruction anchoring mechanism and cutting efficiency of the beak tips may be greatly enhanced as a result.

According to one embodiment, a complex work element may be composed of work elements comprising two or more beaks. The ability to fine tune the length or degree of beak tip exposure of one work element versus the other, and the ability to fine tune the differential rim speeds (rim in this case referring to rotating beak tips as tissue or obstructions are penetrated and severed) enables a clean coring action accompanied by a gentle attack on materials to be cored. If oppositely-rotating work elements are used, the tissue or obstruction to be cored may be presented with, for example, sabre-shaped cutting surfaces that minimally expose the tissue to the cutting blades and vice versa for maximum coring efficiency. Additionally, precisely opposed cutting action may advantageously prevent twisting of underlying deeper wall components, which is a known risk factor for tearing, dissection and other unfavorable tissue disruptions with resulting complete occlusion and flow obstruction, as well as frank vessel wall perforation, often requiring emergency open surgical intervention. Even without discernable acute events, deeper subclinical tissue disruption may lead to more aggressive healing responses in time leading to thrombus formation during the initial recovery period and restenosis due to intimal or deeper, hyperplasia of a vessel during the more extended recovery period. A stable scoopula edge in combination with a rotating inner or outer cutting element, according to embodiments, achieves this favorable effect (non-twisting cutting action) as may two or more oppositely rotating, separate beaks or scoopulas with their crossing distal edges, according to other embodiments. The above-described element may be included in various embodiments herein as may other elements that further stabilize complex work elements, for example, backside struts among others (asymmetry of expansion forces as another example).

Several of the embodiments described herein include luminal access channels arranged in various locations designed to take advantage of a particular type of imaging modality and to likewise minimize their limitations. For example, when an access lumen is expected to image structures that require a longer depth of penetration, then typically an ultrasound element may be utilized. Likewise, if an access lumen is expected to be located in an area where blood is flowing, then again, ultrasound imaging catheters may be the imaging modality of choice in that location. On the other hand, given its higher resolution, optical coherence tomography (OCT) may be the imaging modality of choice where closer examination and more accurate guidance would be desirable, particularly when its limitations such as reduced depth of penetration can be overcome by positioning in close approximation of the desired field of study. This accounts for the variety of locations illustrated throughout many of the configurations. An additional issue for the higher resolution optical coherence tomography imaging modality is that there is absorption and scattering caused by certain tissues that impede its ability to image effectively. Such issues are encountered within vascular structures in particular, where blood flow is needed for delivering nutrients and oxygen to prevent ischemia and cell death and so in certain embodiments, blood flow is reduced or even stopped for a short period of time during OCT imaging.

Other methods and devices are shown in various illustrations and descriptions including the use of imaging chambers that can be used without interrupting blood flow to downstream locations, such as the several embodiments of imaging chambers described herein, many of which have other capabilities incorporated within the imaging chambers, such as cutting ribbons, parting off functions and supporting functions. Being transparent, expandable structures that can be filled with saline or other transparent fluids and being constructed so as not to distort or impede optical transmission and reception, these may also function to extend the reach of OCT for example and thereby increase the capabilities of OCT by overcoming or partially overcoming some of its inherent characteristics, including distortion, scattering and obstruction of the optical signals and receptions sent and received for the purpose of analysis and precise guidance, according to embodiments herein. Additionally, such imaging chambers often include, in the various embodiments herein, internal channels permitting the introduction, positioning and supporting of various excisional modalities such as those utilizing physically sharp blade elements, flush and vacuum to excise, entrap, collect and transport disease elements partially or completely occluding vessels such as arteries, veins and other tubular structures. Other therapeutic elements may likewise be introduced and optimally positioned via these internal channels, which themselves may be elevated, positioned and otherwise supported with various structures including scoopula elements, inflatables, other types of expandable elements as well as simple tubular elements as shown and described in various embodiments herein. Such therapeutic elements may include ablative modalities such as high frequency, focused ultrasound, lasers, radiofrequency delivery elements whether unipolar or bipolar, as well as high energy spark impulses among others for example when encountering a particularly hard proximal cap in a chronically totally occluded vascular channel. Likewise, channels may be optimized for specific delivery of other modalities, including for example, delivering high speed jets of liquid to break up, dissolve or ablate offending materials such as thrombus and other debris, according to embodiments. Additionally, in certain embodiments, delivery of fluids, agents or locally activated physical disruptive solutions, while simultaneously applying vacuum to transport and remove such offending materials are shown and described, in some assemblies as described and illustrated, in concert with other elements that help isolate, trap and augment in other ways, the effectiveness of the mobilization and removal of these abnormal materials, according to methods and embodiments.

The luminal channels are also available for flushing to help clear debris, dilute the effects of blood to obstruct optical imaging, and for such methods as comparative flow, such as Fractional Flow Reserve or other techniques and processes, and pressure measuring for diagnostic flow reserve assessment as well as for before and after treatment comparisons as endpoint determinates.

The role of the basic excisional structures described herein, particularly with or without a scoopula, is likewise multifunctional, according to embodiments. Their roles include excision and removal of offending obstructing materials. In the process of doing so, however, such devices may be often called upon for delivery of other elements specialized for dealing with chronic total occlusions and other stepwise therapeutic maneuvers. For example, several embodiments demonstrate how smaller working elements may be strongly supported by the larger working assembly, positioned proximal to the either subtotally or totally occluded segments of a vessel, the larger element temporarily serving as a platform for imaging using various modalities. The larger primary assembly or work element(s) may also be called upon to strongly, precisely elevate, provide back support to, angle and otherwise optimally position smaller elements, while providing a robust, precise and stable platform from which the smaller elements can image, guide and operate together with other elements delivered to the site of activity. The larger device may also provide a stable reference point and may also ensure adequate flow beyond the area upon which the smaller elements are engaged. The larger elements may provide directionality, shielding and isolation to the smaller elements to optimize safety and ensure that an area of interventional activity is completely cleared of materials while protecting against clearances that proceed too deeply into normal vascular layers and structures, in some cases based upon optimal positioning of guidance modalities either leading the way, or directly adjacent to a cutting, coring or ablating element. Another method described and illustrated herein makes use of depth limiting elements, which are described in several of the embodiments herein and that may be used together with or independently of imaging as desired.

Another significant aspect of the various embodiments disclosed herein includes the use of staged introduction of elements. In simple cases, where all that would be required is the use of the primary excisional device, then other elements need not be introduced at the beginning of a procedure, but may thereafter be introduced at will through available channels. For example, one embodiment of the excisional device may be used in a standalone manner for penetrating through or around, excising, parting off, collecting and transporting out of the body, offending obstructive materials. The same instrument, however, can be utilized with imaging for more precise interventions. In a like manner, a standalone excising embodiment may utilize a distally-delivered parting off chamber, whether equipped with inherent parting off capabilities or not. In certain use cases, where a scoopula may not be needed or even desirable, the one simpler embodiment is fully capable of all the functionalities with or without the scoopula, except for the directionality it provides as well as the inherent protection of a vessel wall that has obstructive disease on one side, but other sides are not affected. In that instance, therefore, it may be desirable to shield it from the cutting effects of blades or other cutting and excising modalities.

A significant aspect of the staged introduction capabilities disclosed herein is that when dealing with obstructive materials, there may be multiple acceptable options. For example, in the case of a mixed obstructive lesion where thrombus may be anticipated, a first phase clearing of thrombus may involve certain elements to be combined to clear the clot(s), which after accomplishment of that phase, the firmer plaque material may then be precisely excised without as much risk of downstream embolization. Throughout the illustrations and descriptions herein, there are generally provisions for a multitude of combinations of elements and embodiments as are shown. Moreover, there are other combinations that are not shown but are clearly optional and may be favorable, and all such combinations are considered to be encompassed by the disclosure of embodiments herein. One such combination involves certain elements providing elevation while others may then by utilizing that platform positioning, angle an excisional or imaging element to permit penetration or excision. Once penetration is achieved, a small channel may be enlarged, or an expandable element may simply be utilized to provide powerful backup support in certain embodiments. Likewise, an elevation platform may be optimally utilized with a centering expandable element that may then create an opportunity for clearing an off-center obstruction.

A significant capability that is illustrated and described in several embodiments herein is the overall commonality of access and imaging enhancements that is provided by devices and methods described herein that is enabled by carrying certain structures far distally to a site by introducing needed elements in a tailored approach for a given area in the body, with the uniquely different requirements specific to the anatomy and composition. The elements of an interventional or excisional device that may contribute to an overall assembly specific for a region of interest, according to embodiments herein, may include various cannula channels and other chambers whose functions are optimized by shared capabilities with other elements for enabling image optimization and for providing directionality including rotation, angulation and other coordinates manipulations in a platform described and illustrated herein that provides stability and support. Such elements demonstrate that the devices described and illustrated herein are equally suited to, for example, bronchial passageways as they are for vascular spaces, one example being the portability of elements that are utilized for recreating an optimized ultrasound or optical guidance pathway in an area that may be lacking a natural medium through which to transmit and receive minimally obstructive, minimally distorted signals. In order to take advantage of the in-situ and precision imaging available in this manner, further embodiments include elements designed to enhance local control of parameters such as precision directionality and depth of excision, imaging and sampling according to embodiments and methods herein.

Several embodiments are shown that may be more or less effective on their own depending on the nature of the material being excised, ablated, or otherwise disrupted for removal or clearing and in order to maximize effectiveness, elements are described and illustrated that work together with other elements in assemblies that overcome limitations that would otherwise exist.

The terms "imaging" or "imaging element", or "excising and imaging" generally refer to elements that can have multiple capabilities. For example, tubular lumens, expandable chambers and the imaging elements themselves may be referred to with such terms indicating that the designs of the embodiments can be presumed to be optimized for the option of including imaging modalities of various types in these elements or may refer to the imaging elements themselves in which case it can be presumed that the various modalities are generally interchangeable. It should also be noted that the dimensions of the illustrated structures may change as newer iterations of modalities as well as the types and sizes of excisional elements that may also be forthcoming due to advances in construction, materials, methods and manufacturing, as these can be presumed to enhance the capabilities of the embodiments herein. All such variations are within the scope of the embodiments disclosed herein.

Many of the illustrations herein reference use of the disclosed devices and methods in vascular structures. However, these devices and methods may be used in a variety of tissues and organ systems, including lymphatic channels, nerve conduits, urinary channels and other closed and open living structures such as gynecologic and other ductal, hollow spaces such as airways, spinal cord channels, central nervous system spaces and any of many more potential spaces. The specific application likewise may require dimensions other than those suggested by the illustrated proportions and scale. However, it is presumed that the same principles of action and function would be preserved and that such other use cases and variations are well within the scope of the present disclosure.

As used throughout this disclosure, the term "work element" or "work elements" may comprise one or more tubes, and the terms "inner" and "outer" tubes may be used with reference to a single work element, or in reference to two or more co-axially located work elements (or "complex work elements", as used herein), which may comprise one or more tubes to enable their specific function. Generally speaking, the terms "distal" and 'forward" refer to downstream positions (e.g., away from the surgeon or practitioner), whereas "proximal to" or "back end" generally refer to positions more upstream in a flowing vessel (e.g., closer to surgeon or practitioner). Likewise, "inferior to" or "underside" refers to a location that appears at or near the bottom in an illustration, opposite a "top" or "upper" area, although it must be understood that where working in blood vessels is concerned, these are relative terms that may be inferior in an illustration for example but may actually be at the top depending on the rotation of the vessel as well as the rotation of the elements of an embodiment or embodiments. A coaxially-disposed outer tube, according to one embodiment, may also comprise one or more coatings. According to one embodiment, an outer tube may comprise a stainless-steel hypodermic tubing ("hypo tube"). Such a stainless hypo tube, according to one embodiment, may be provided with (e.g., laser) cuts to selectively remove tube material to define a monolithic distal assembly that defines beaks, a living hinge that attaches the beak(s) to the generally tubular body of the device or that homogeneously spans between the beak(s) and the generally tubular body of the device. According to one embodiment, cuts in the hypo tube may define one or more tendons configured to actuate the beak(s). The cuts in the hypo tube may also define one or more tendon actuation tabs or body portion actuation tabs that enable actuation (e.g., opening and closing) the beak(s) through the tendons or body portion, according to embodiments, and limit the travel thereof. The tendon actuator tab(s) or body portion tab(s) may be located at any location along the length of the hypo tube. According to one embodiment, portions of the tube may be rigid. According to another embodiment, laser cuts along the proximally extended body portion of the tube may enable flexibility over its entire length or one or more portions thereof. The device may also comprise materials other than stainless steel, such as plastics or other suitable materials, which may incorporate the features of the beak(s), tendon(s), and, according to embodiments, tendon actuation tab(s) or an internal tube actuator element. Aspects of the devices and methods disclosed herein are related to the devices and methods disclosed in co-pending and/or commonly assigned U.S. Pat. No. 9,463,001 entitled "SOFT TISSUE CORING BIOPSY DEVICES AND METHODS"; U.S. Pat. No. 10,070,884 entitled "SOFT TISSUE CORING BIOPSY DEVICES AND METHODS"; U.S. Pat. No. 9,155,527 entitled "SOFT TISSUE CORING BIOPSY DEVICES AND METHODS"; U.S. Pat. No. 8,992,441 entitled "AUTOMATED, SELECTABLE, SOFT TISSUE EXCISION BIOPSY DEVICES AND METHODS"; U.S. Pat. No. 9,039,633 entitled "AUTOMATED SELECTABLE SOFT TISSUE EXCISION BIOPSY DEVICES AND METHODS"; U.S. Pat. No. 10,076,315 entitled "SOFT TISSUE BIOPSY OR EXCISIONAL DEVICES AND METHODS"; U.S. Pat. No. 9,999,758 entitled "IN SITU MATERIAL DELIVERY DEVICES AND METHODS"; and U.S. Pat. No. 10,231,750 entitled "EXCISIONAL DEVICE DISTAL WORKING END ACTUATION MECHANISM AND METHOD"; the entire disclosures of which are hereby incorporated herein in their entirety.

Reference will now be made in detail to the construction and operation of implementations of the embodiments illustrated in the accompanying drawings. The following description is only exemplary of the embodiments and methods described and shown herein. The embodiments, therefore, are not limited to these implementations, but may be realized by other implementations.

FIG. 1 is a perspective view of a flexible excisional and imaging device 10 according to an embodiment. As shown, the imaging device 10 may include a work element 13 constructed of and from, in one embodiment, a monolithic tube with an articulated beak set 14 and a flexible outer sleeve 25.

Figure 2:
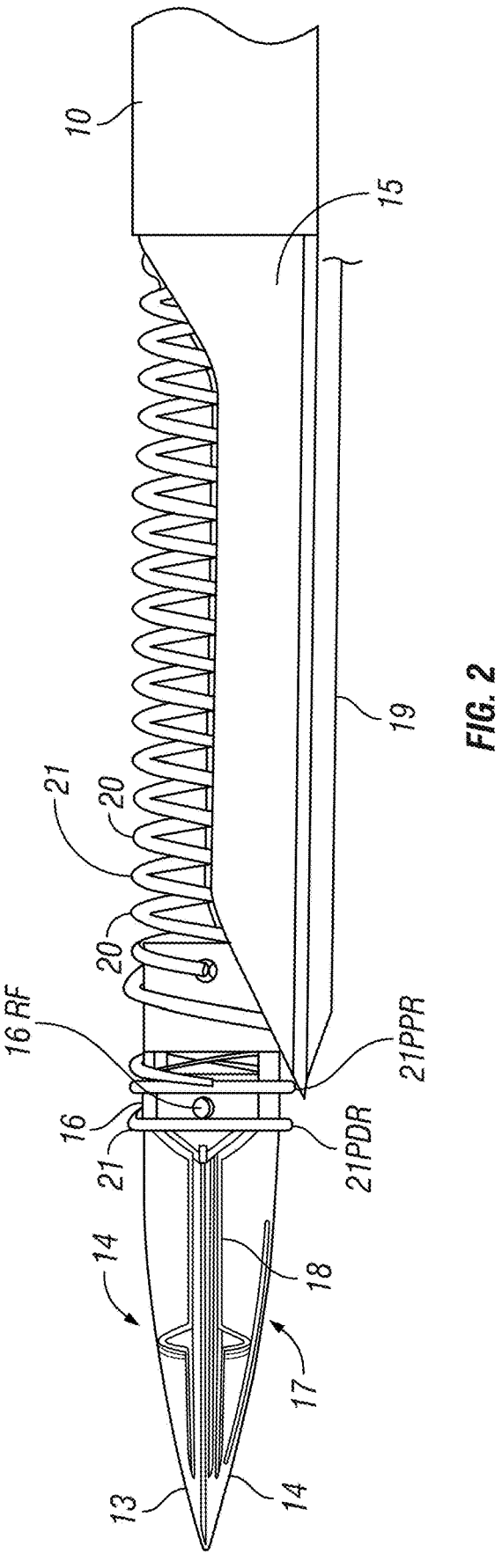
FIG. 2 is a side view of an excisional device in a closed configuration, according to one embodiment.

FIG. 2 is a side view of an excisional device in a closed configuration, according to one embodiment. As previously described, the features of the work element may be cut from a single tube. Such a work element enables matching lips or tips only, with scissors mating at lateral lips overlap during, and at closure, and includes living hinge element 17, living tendons 18, travel limiting structures such as keystone-shaped, or tendon actuation element 16 (hereinafter referred to as the "keystone" element), and a movable scoopula 15. According to embodiments, travel limiting element 16 may include a race follower element 16RF that may circulate around the work element 13's inner diameter, within an area defined axially by the forward termination of the coil of helical actuator 21 including roughly parallel over a portion of its flight, distal race limiter 21PDR and roughly parallel over a portion of its flight, proximal race limiter 21PPR. According to embodiments, helical actuator element 20 may be a helical tubular element whose flights or windings of revolution may nest between flights or turns of helical actuator 21, whose revolutions may be of similar pitch for example, so that when two such helical elements thus configured rotate together at the same speed, no relative axial motion between the two occurs. However, were one of the elements 20, 21 to be rotated at a different pace or rotational speed from the other, then a relative or differential axial motion between the two would necessarily occur. Referring to FIG. 2 then, were proximal actuator element 20 made to spin faster in, for instance, a clockwise direction (rotational direction referenced to looking from proximal vantage point to distal) than distal actuator 21, the relative axial motion between the two would cause actuator 21 to crawl forward along actuator element 20's windings until their rotational speeds were equalized at which point axial motion would cease. To return actuator 21 to its original axial starting position relative to actuator element 20, its rotational speed would simply need to speed up higher relative to actuator element 20's rotational speed until such original starting point were again reached. Thereafter, maintaining equal rotational speeds for actuator 21 and actuator element 20 would ensure that further axial changes between the two would cease and stabilize—to the extent relative rotational speeds of the two actuator elements were held stable, according to embodiments. Alternatively, actuator element 20's speed could be slowed to match that of actuator 21, with the same result of synchronous rotational speed. Referring again to FIG. 2, actuator 21's termination in parallel distal and proximal race elements, enables continuous equal pace rotation of actuators 21 and 20, resulting in axial stability as well as permits advanced and retarded rotation of work element 13 brought about as a result of its solid attachment to actuator element 20, relative to actuator 21, whenever rotational speeds of actuator elements 20 and 21 are different. In the event rotational speeds of actuator 21 and 20 are different, not only would work element 13 progress or regress in rotation, with keystone (i.e., travel limiter) or tendon actuation element race follower 16RF progressing and regressing rotationally together with the rest of work element 13, within the axial area defined by edge limiters 211 and 212, but race follower 16RF together with its attached travel limiter (keystone) 16, and living tendons 18 would move axially distally or proximally relative to the rest of work element 13 including its living hinge backbones 17, the direction of axial motion depending on whether actuator element 21 were rotating faster in a clockwise direction (direction of rotation referenced looking from a vantage point proximally to distally). In that case, the travel limiter 16, its race follower 16RF and attached tendons 18 would all retract axially in a proximal direction relative to the backbones 17 of work element 13 as a result of work element 13's attachment to actuator element 20, as actuator element 21's flights crawled back between actuator element 20's similar flights, all of which would cause the beak elements 14 to progressively close to a tightly apposed position for rotational dissection and penetration purposes or other purposes such as for severing off tissue cut by beak elements 14, according to embodiments.

Also illustrated in FIG. 2 is scoopula 15, which though shown straight, may be flexible along with outer flexible tube 10, according to embodiments and as shown in FIG. 1. The scoopula or trough 15 may be entirely or partially transparent over its entire extent or in key areas where optical transmission may be desirable. An additional, optional non-rotating flexible sheath may be provided to cover over actuator elements 20 and 21, is not shown in FIG. 2 but such an optional element is shown in subsequent figures. Additional tubular element 19, similar in function but different in location to, elements 23 and 24 shown in subsequent illustrations, may also be provided and may enable independent movement of guiding elements for example, with proximal entry point(s) (purposely undefined in this figure, since various choices of entry point(s) may satisfy specific indications, according to embodiments).

Figure 3:
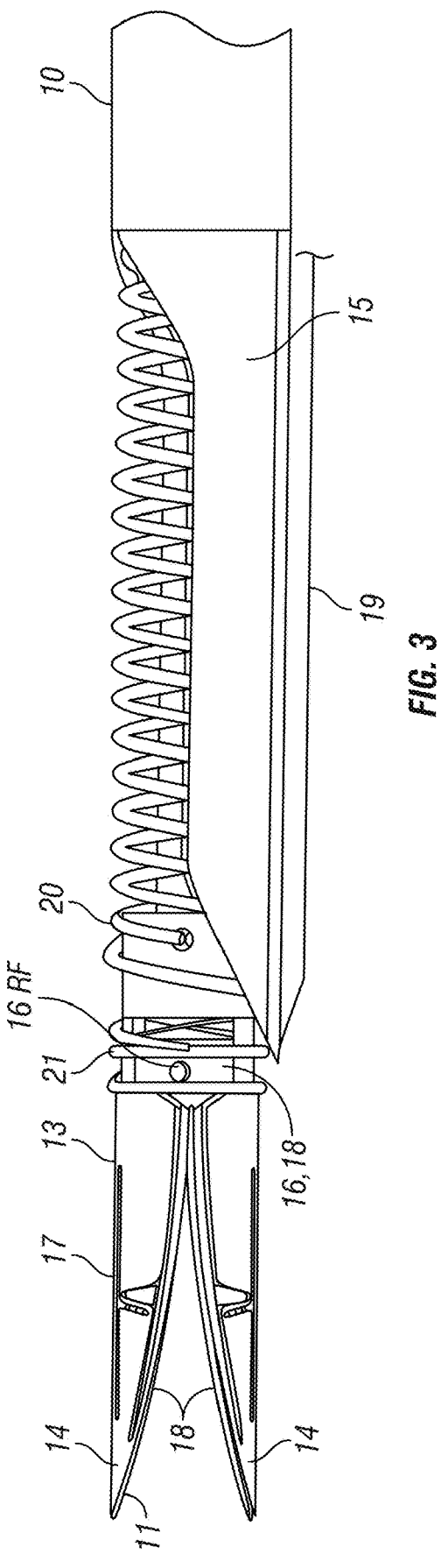
FIG. 3 is a side view of an excisional device in an open configuration, according to one embodiment.

FIG. 3 is a side view of an excisional device in an open configuration, according to one embodiment and illustrates another state of the work element 13 of FIG. 2, this time with the beak elements 14 widely open and extending beyond scoopula 15 (noting that keystone 16 and its race follower element 16RF are now in an axially advanced position, forcing tendons 18 also distally, while actuator element 20 is holding back living hinge backbones 17, as may be compared to keystone 16's position shown in FIG. 2. It is these relative changes that actuate beak elements 14, which themselves are enabled to be rotating during the entirety of the transitions from closed to open and back to closed as may be clinically desired, as often as may be useful, during a diagnostic and a therapeutic procedure)). The position of the keystone element shows additional space for "diving" or overdrive closure of the beak elements 14 as well as for overdriving opening (i.e., beak tips 14 will be extended to an expanded diameter that may be greater than the diameter of the tube from which they were formed). Another embodiment utilizing the same mechanism of converting differential angular motion into axial excursion for the purpose of actuating beaks is directly attaching a spiral element or a plurality of elements spaced between a number of one or more additional spiral elements, directly to the keystones (or a keystone or keystone equivalent) in embodiments, while the one or more spiral elements are (is) attached directly to the tubular base (backbone) structure(s) of the beak element(s) which, according to the illustrated embodiments, are of a single monolithic structure—that is, formed from a single tube of material from which material is selectively removed such that the remaining material forms the desired structures.

According to embodiments, a multi-strand much more linearly oriented than illustrated in this figure and FIG. 2 would impart little twist on the backbone structure nor on the keystones, which could then, with any additional side clearance that may be required, function in exactly the same manner, that is, that by twisting multiple, even only slightly angulated in some cases, (mostly co-linear with the longitudinal axis, but with a small degree of twist, for example in a multi-strand winding, every other strand or group of strands could be independently rotated relative to others in the winding assembly) elements differentially, one or one group to another, a small angular degree of rotation—one group being attached to the backbone slightly more or less than another group (keystone group) would achieve the same result as shown in FIG. 3 and other figures, and according to embodiments. Likewise, a minimally-twisted set of bands attached to or an extension of keystones themselves could nest between another one or more similar bands and again, with differential (slight) rotation could activate the beaks for opening and closing. Such bands, multiple strands or flexible tubes could also in addition to causing beak opening and closing, provide rotational motion and control according to embodiments.

Therefore, an embodiment may include a flexible tube, braids, windings, bands or any combination thereof to provide a mechanisms for differentially causing keystones and backbones to open and close during spinning or reciprocating rotation, and also during non-rotation of the beaks for penetration, excision and parting off purposes. Additionally, the scoopula portion is in a slightly more proximal or slid back position (relative to the flexible beak element(s) 14) to show the relative independence of scoopula 15 and work element 13 with its flexible actuators and other components, to project forward while being rotated, as well as optionally utilizing beaks open and closed to penetrate a total vascular occlusion for example. The degree of extension of the scoopula portion beyond the beak elements 14 could be used to limit exposure of vascular walls to the bulk of working assembly 13 as well as to its extremely sharp elements such as beak tips of beak elements 14 particularly when these are in the open position for example, until such time as using the working elements of 13's full capabilities may be deemed useful. It should be noted that the inclusion of a scoopula element enables beaks to excise effectively without the need for a non-rotating sheath (NRS) to cover the majority of the beaks for maximum efficiency of excision. Several illustrations in which the scoopula is included purposely indicate the relative independence of the beak elements 14, of a an NRS element 22 covering according to embodiments. The scoopula 15 shown and described in several illustrations may be fully transparent, or specific sections of a scoopula may be transparent to optical signals and others along the electromagnetic spectrum for purposes of optimal, direct local imaging, according to embodiments. The scoopula 15 may also be constructed with non- or minimally ferromagnetic materials such that it may be pre-placed in precise position, for use during magnetic resonance imaging where magnetic elements cannot be used. Once a stable position is established, other elements may be introduced and manipulated manually directly or robotically, or utilizing an automated, robotically controlled series of steps. The side tubular element 19 may have numerous uses, particularly since the scoopula 15 of which it is a part, may be independently rotatable from other elements of the device, such that the access provided by tubular element 19 may be used for a variety of additional elements, such as a flexible (non-rigid) "flap" or one-way distal valve element(s) (not shown) which may be introduced to prevent distal embolization or to further isolate certain areas for pressure augmentation via channels in this and other embodiments. Additional lumens or channels similar to tubular element 19 may be added and used for contrast injection, flow augmentation, guide wire passage, imaging element passage such as phased-array "ultrasound on a wire" intravascular ultrasound (IVUS), fractional flow reserve (FFR) and instant wave-free ratio (iFR) devices among others, which are available on flexible wires ranging from about 0.009"-0.018" for example. The scoopula 15 itself or the beak elements 14 can be a mounting point for imaging technologies such as optical coherence tomography (OCT), IVUS, near infrared and other imaging modalities and combinations to assess such factors as plaque vulnerability among others. Channels may be provided for fluid management including delivery and vacuum. A channel could be used for example, to over-pressurize a proximal segment while measuring iFR or FFR distally, to augment functional gradient measurement to gauge functional significance of stenotic segments before, during and after interventions, particularly in cases where it may be helpful to overcome limitations of abnormally decreased ambient intraluminal pressure as a result of impaired left ventricular function or sequential stenoses, and in cases where there may be a desire to avoid use of pharmaco-dynamic agents such as adenosine when performing functional studies. Such elements are shown in subsequent illustrations, along with additional tubular access channels associated with various elements of embodiments of the present device.

Figure 4:
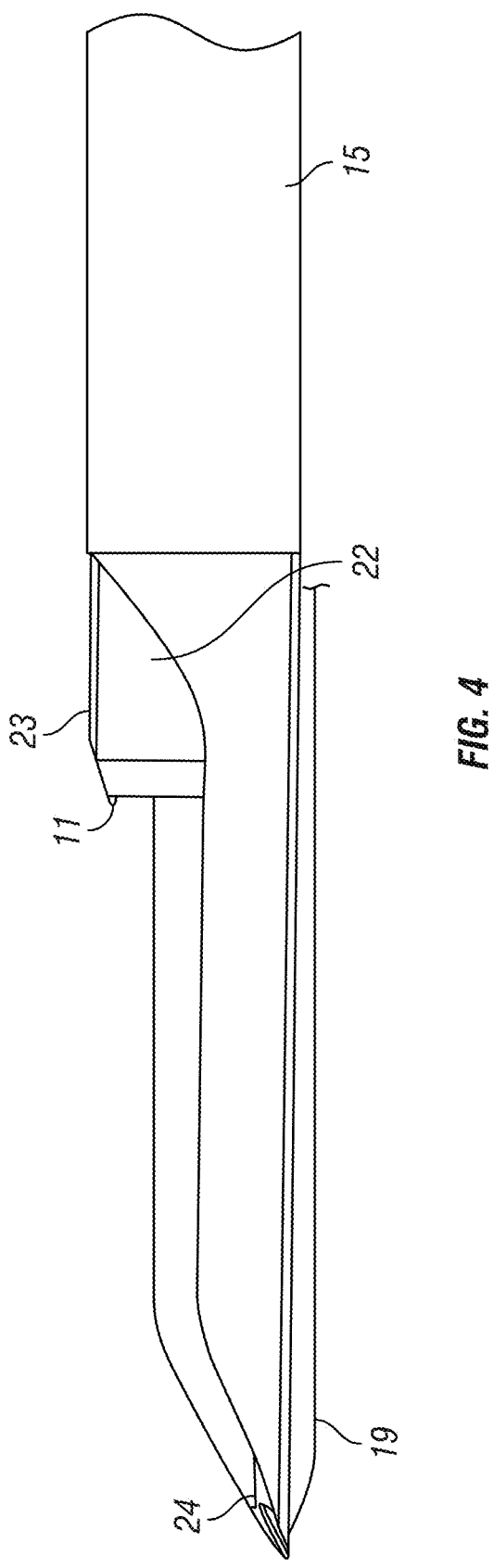
FIG. 4 is a side view of an excisional device, according to an additional configuration in one embodiment.

FIG. 4 is a side view of an excisional device, according to an additional configuration of one embodiment comprising a scoopula 15 with two additional access tubular elements 19, located on the outer surface; and reference 24, coaxially co-extruded with the scoopula's wall, which may provide an additional lumen or lumens for example for a guide wire or other working element close to a tubular lumen that can provide an access path along access tubular element 19 for an imaging catheter or wire in close proximity to coaxial tubular element 24 according to embodiments. Additionally, FIG. 4 shows an outer non- or differentially rotating sheath 22 covering the beak elements of beak elements 14, exposing, as may be desired, only the forward lateral and distalmost portions of beak edges 11 and their distal tips to any desired depth. The non- or differentially rotating sheath element 22 is shown equipped with an additional tubular lumen element 23 that may provide access as desired for an imaging catheter or wire and may be rotated by machine or by hand to sweep by rotation as well as axially in a distal and proximal direction to interrogate an area with close up views, particularly if the vessel being treated happened to be of large caliber, potentially beyond the range of an imaging modality that otherwise might be positioned less closely to the subject matter of interest, when utilizing a modality such as optical coherence tomography (OCT).

An additional feature of the use of element 23 lumen, whether collapsible and then expanded by filling its internal lumen with another element such as an imaging wire or catheter, is that when it is placed between the cutting elements and the tissue being excised, its position being so close to the cutting elements' edges 11, coupled to the depth limiting effect of beak edges 11 being so minimally exposed, then together or separately these may be utilized to more precisely control depth of cutting into the vascular disease, to avoid traumatizing deeper, normal (e.g., non-diseased or stenosed) wall components, for example, or for the purpose of enabling several, increasing diameter excisional passes for purposes of positively controlling the removal of lesion material and, therefore, limiting potential embolic material release into the bloodstream. Also, given that imaging elements can be placed in various locations often with the scoopula in the field of view, and that the entire or partial distal area of the scoopula 15 beginning in the trough section may include or may be formed of transparent material such as clear polymer or other such material, full sweep interrogation is enabled by certain imaging modalities that provide great detail such as optical coherence tomography (OCT) according to embodiments. Likewise, marking elements may be incorporated in the scoopula, or actually delivered to a vascular wall by device 10 to indicate which parts are facing away from the protective faces of the scoopula, for imaging reference purposes. The choices of access locations for imaging elements may thus be coupled with aggressive penetrating elements such as stiffer, more controllable guide wires and catheters among others as will be shown in further illustrations to follow, according to embodiments.

Figure 5:
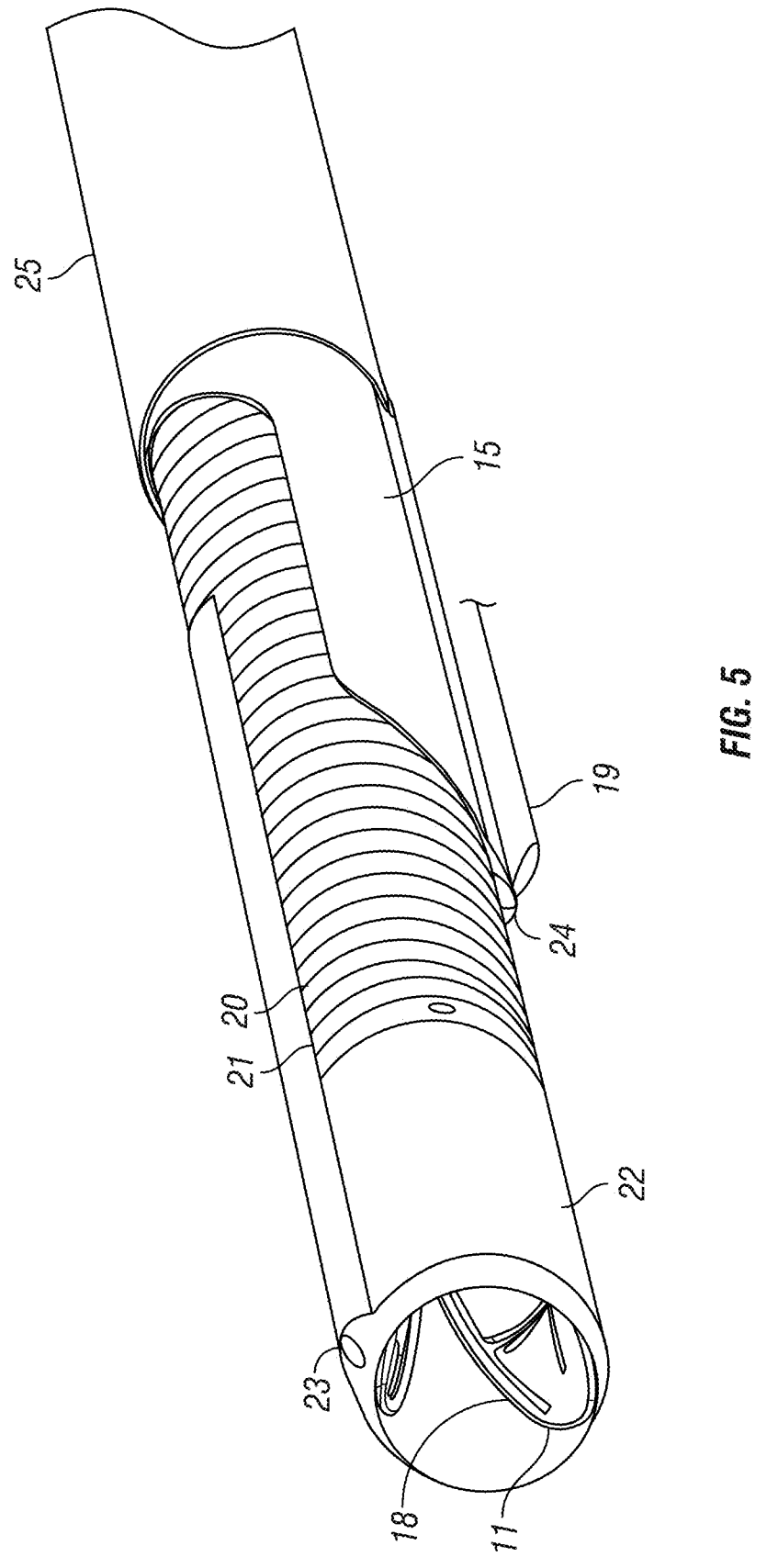
FIG. 5 is a perspective view of an excisional device in an open coring mode, according to one embodiment.

FIG. 5 is a perspective view of an excisional device in an open coring mode, according to one embodiment that is similar to that of FIG. 4 but now depicts a cut-away view of the non- or differentially rotating sheath 22 and its, partially shown in cutaway, collapsible tubular access element 23 for clarity and to reveal inner actuator elements 20 and 21, all of which may be flexible. Also highlighted by the clearances (cutaways) is the extremely thin wall nature of non- or differentially rotating element 22 including its access tubular lumen element 23, which may be partially or entirely made of a transparent material such as polyimide or other materials including a variety of transparent polymers. Note that non- or differentially rotating sheath 22 may continue all the way back proximally within over-tube element 25 or it may terminate at any point therein. Likewise, tubular access element 23 may also extend all the way proximal within over-tube element 25 or it may terminate at a different point within over-tube element 25. Note also that element 24 may also be a collapsible tubular lumen. Revealed as well in FIG. 5 are more of the details of the cutting, opening and closing elements of the work element, including beak edges 11, tendons 18 and various other construction details. Also shown to further clarify the function of scoopula 15 as independently also rotatable and extendable, is a separate over-tube 25, which may cover over tubular element 19 or its wall may lie between element 19 and scoopula 15, in which case tubular element 19 may only be attached to scoopula 15 near the distal tip of scoopula 15, according to embodiments. A thin-walled sheath 22 has been removed to expose the flexible actuator elements 20 and 21, the latter forming a distal parallel race within which race follower 16RF freely rotates as elements 20 and 21 are rotated differentially. It should be noted that race follower element 16RF need not move far within its race boundaries in order to fully close and open beak edges 11 via differential motions of living hinge element 17 and tendons 18, resulting from the axial actions of elements 20 and 21 as outlined in detail previously. Also illustrated is separately extendable, optionally of polymeric and transparent material, scoopula 15, including its access tubular element 19 from within flexible over-tube 25 according to embodiments.

Figure 6:
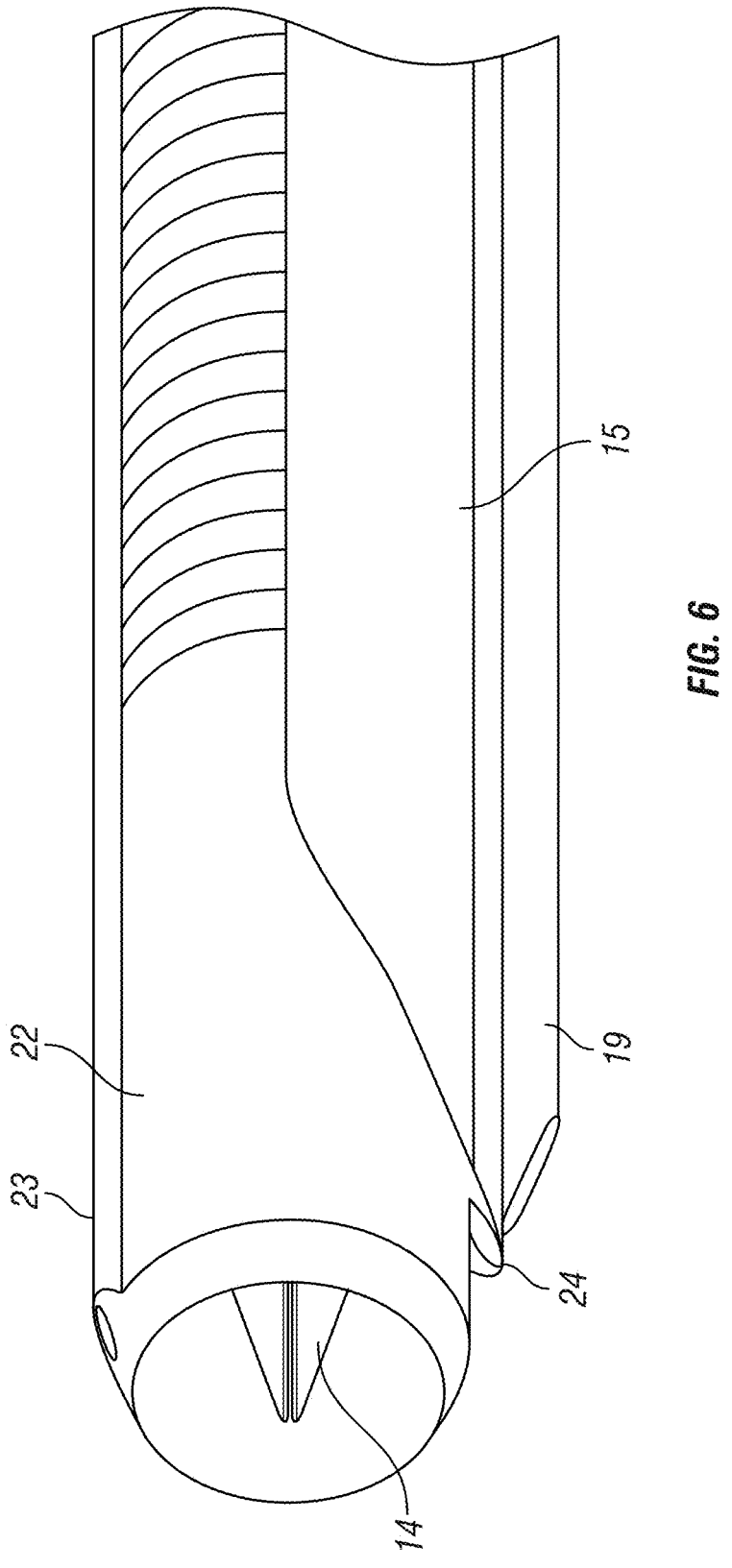
FIG. 6 is a perspective view of an excisional device of FIG. 5 in an additional closed configuration according to one embodiment.

FIG. 6 is a side view of the excisional device of FIG. 5, with work element 13 and its components now in extended, closed, configuration for severing off tissue and for rotational dissection with closed beak elements 14. As shown, the beak edges 11 are opposed to one another, partially or fully hiding their sharp edges for minimally traumatic blunt, rotational dissection of tissues. The non- or differentially rotating sheath 22 is now shown in non-cut-away view with lumen access port 23 partially rotated towards the viewer to demonstrate is positional capabilities for viewing proximity to a vascular wall, area of interest. Also shown is a scoopula 15 with its auxiliary tubular lumens 19 and 24.

Figure 7:
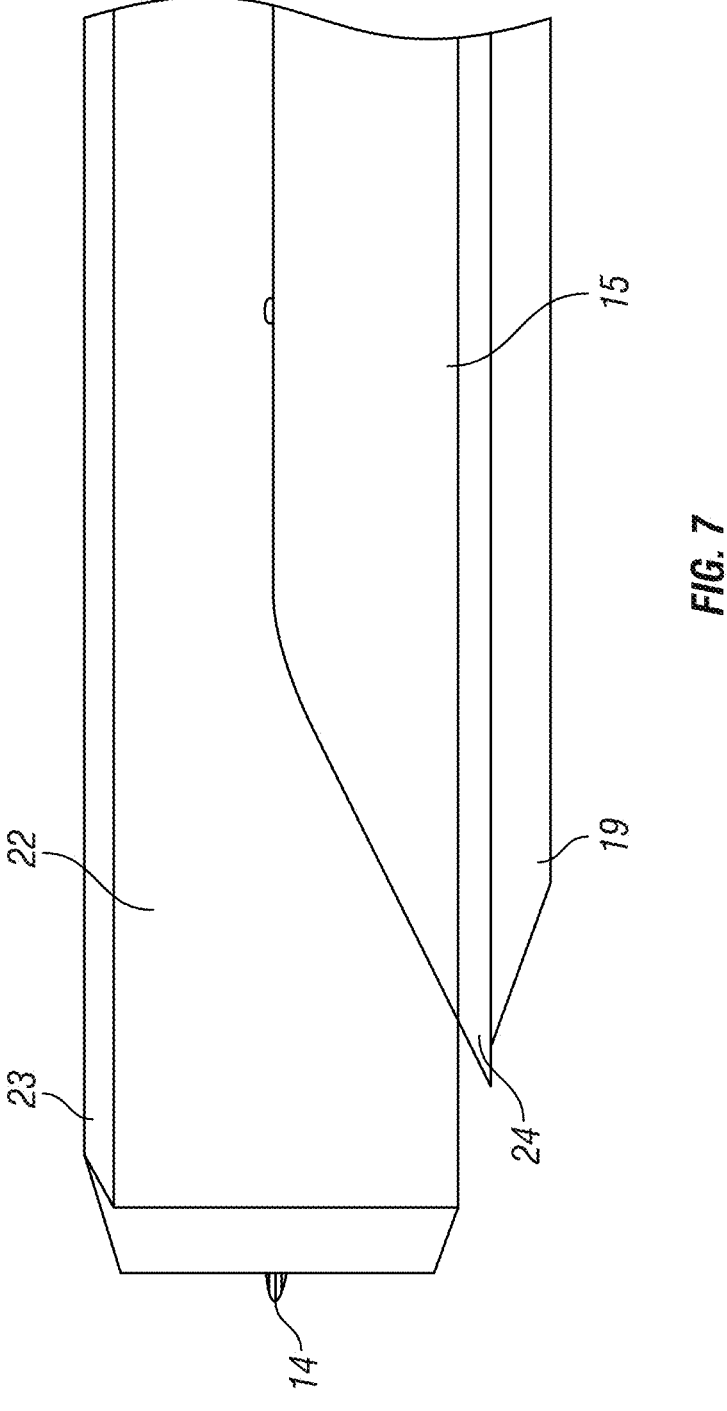
FIG. 7 is a side view of an excisional device of FIG. 6 in extended, closed configuration according to one embodiment.

FIG. 7 is a side view of an excisional imaging device or assembly of FIG. 6 to show that beak elements 14 closure and parting off can occur in a recessed position within a non- or differentially rotating sheath 22 as well as the various positions of the scoopula 15 and access channels 19, 23 and 24 according to embodiments.

Figure 8:
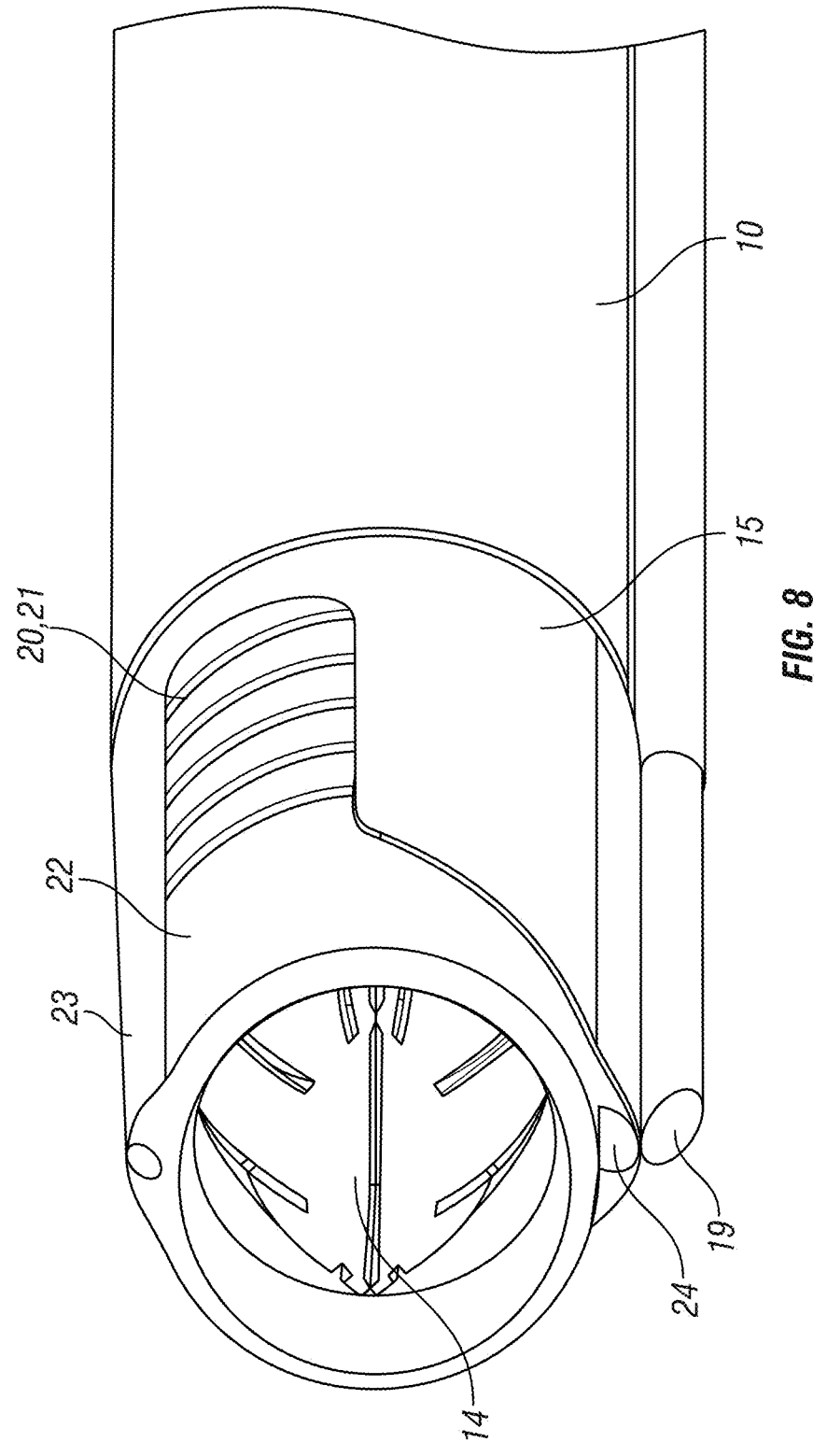
FIG. 8 is a perspective, closer-up view of an excisional device, revealing a working element in closed configuration according to one embodiment.

FIG. 8 is a more head-on view showing the same elements as in FIGS. 6 and 7 and clearly shows the coaxial nature of beak elements 14, with non- or differentially rotating sheath 22, disposed coaxially with scoopula 15 and outer housing 10, according to one embodiment.

Figure 9:
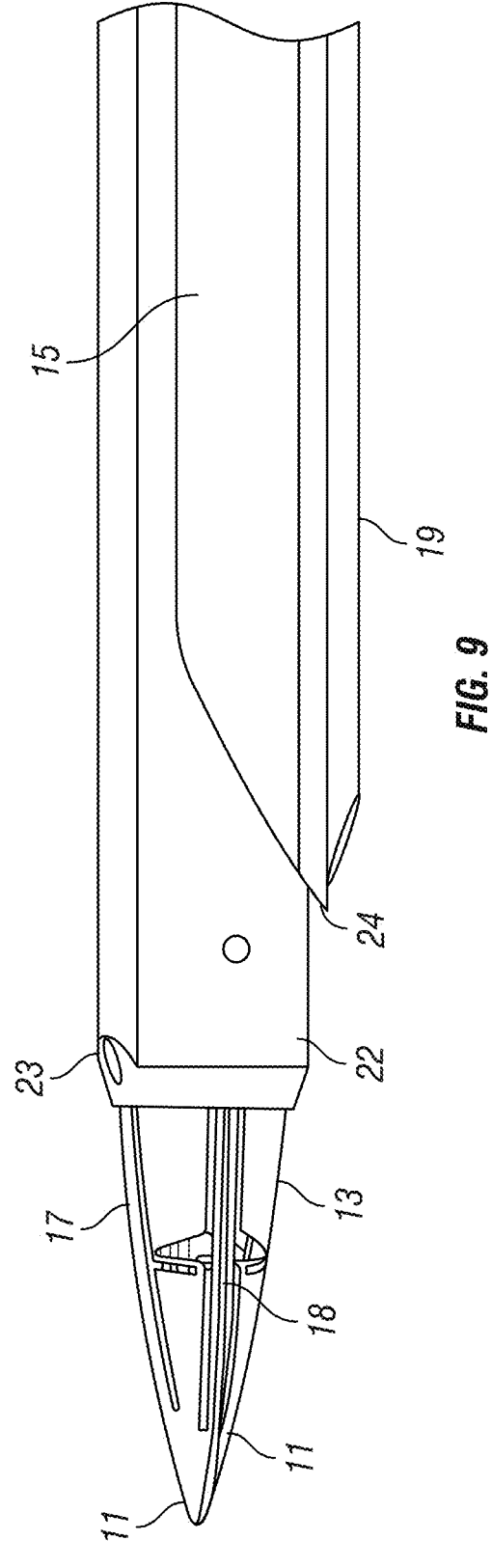
FIG. 9 is a side view of an assembly with a work element and other components of an excisional device, according to one embodiment.

FIG. 9 is a side view of an excisional imaging device or assembly (hereinafter "device" and "assembly" will generally be used interchangeably) in an extended, closed beak elements 14 configuration which allows for streamlined, minimally disruptive advancement, whether through a constricted luminal space, with or without a guiding element such as a guide wire or micro catheter for example and may also be used to penetrate a completely occluded vessel, using rotation to minimally dissect its way through potential spaces it creates or existing spaces it takes advantage of in the case of a small or even non-apparent channel in the tissue and according to embodiments.

Figure 10:
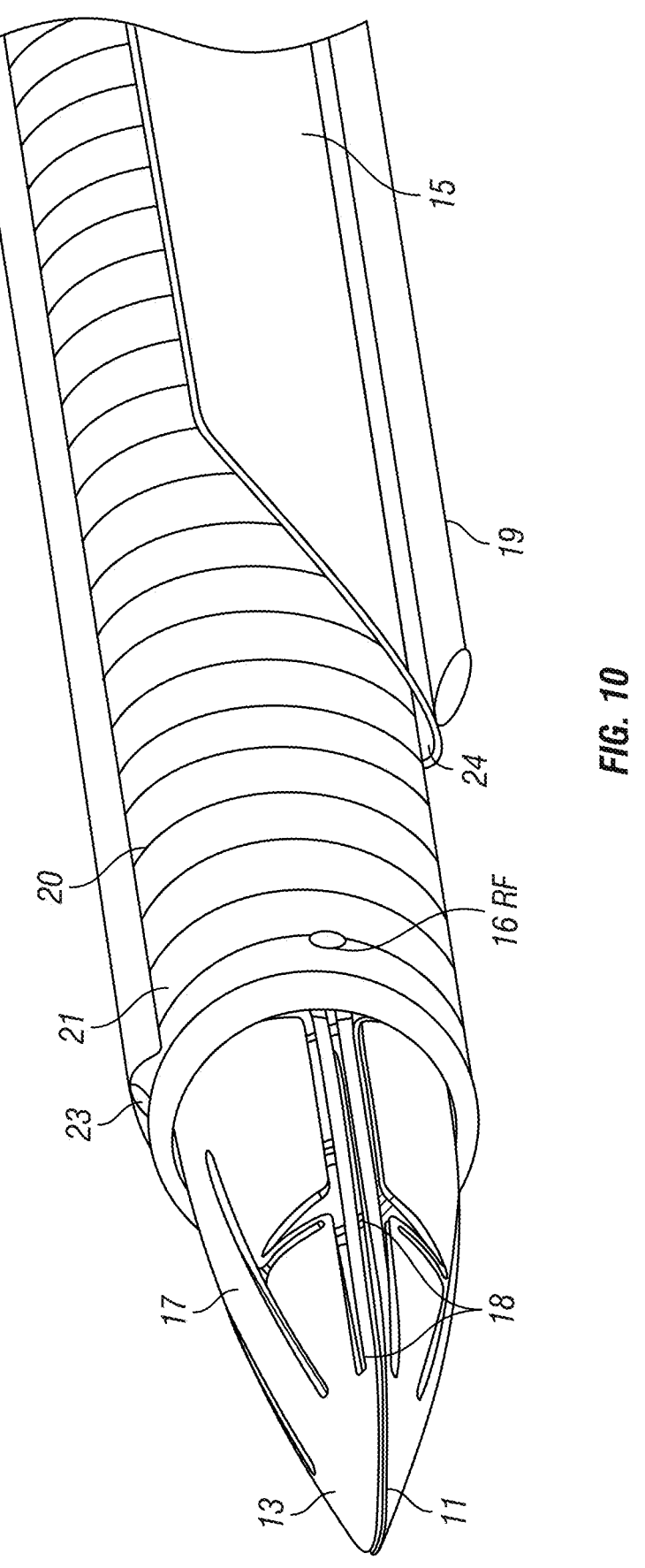
FIG. 10 is a perspective view rotated slightly to reveal forward and sideways rotation functionality of a work element of an excisional device with its working element in extended, closed position, according to one embodiment.

FIG. 10 is a side view rotated to demonstrate independent rotation capabilities of work element 13 for coring, rotational dissection and parting off, non- or differentially rotating sheath 22 with its tubular luminal channel in tandem aimed away from scoopula 15 as if 23 were directed towards and adjacent to a vascular wall to permit imaging elements introduced therein to gain close-up details of vascular wall structures and abnormalities, while other more global interrogations at longer range may be performed via one or more of the tubular access channels such as element 19 for example. Coring can be carried out in both forward and sideways by exposing work element 13 to tissues in front of and along a vascular wall according to embodiments.

Figure 11:
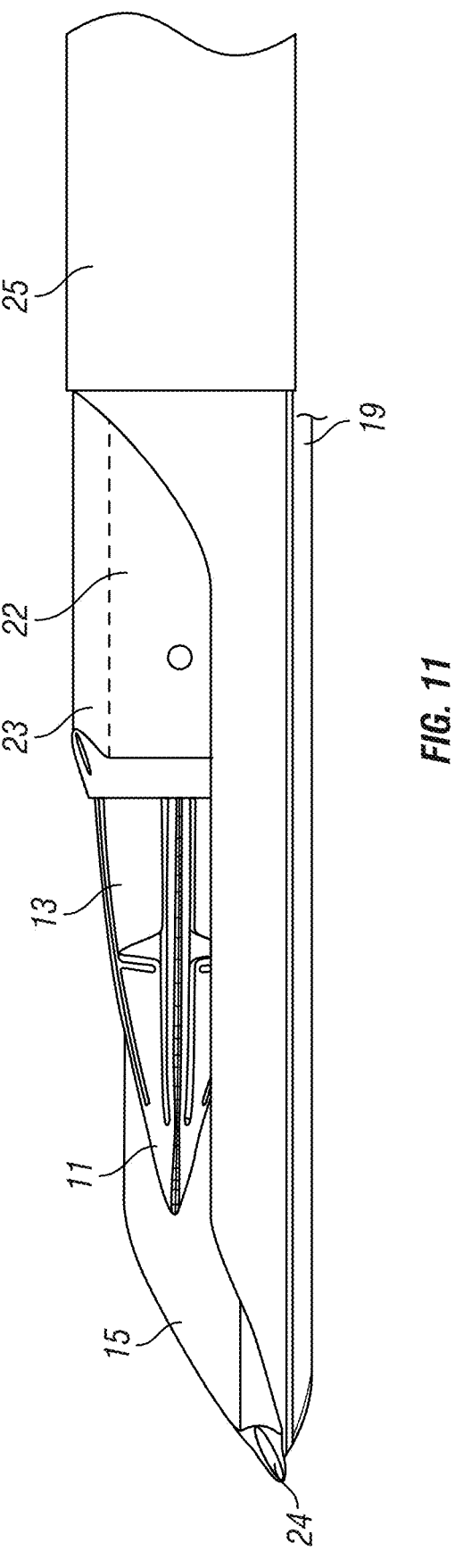
FIG. 11 is a side view of a device of FIG. 10 with its working element in closed configuration but in a different position relative to additional components, according to embodiments.

FIG. 11 shows a slightly tipped side view of an excisional device, revealing the working element in its closed configuration, according to one embodiment. In this illustration, the work element 13 is shown in closed configuration, depicting a clinical situation where the scoopula 15 defines and encompasses an entire area of interest for vascular disease de-bulking, all of which may be mainly guided by incorporated imaging instruments, introduced according to the preference of an operator, via the one or more access channels 19, 23 and 24 as desired. Each or all of these may travel along and slightly ahead of the cutting edges 11 of beaks 14 of working element 13 according to embodiments. Also shown in FIG. 11 is that the scoopula 15 may be extendable. In this case, a small space between the outer wall of scoopula 15 and outer wall of tubular access element 19 may permit outer flexible tube 25 to fit closely around scoopula 15 without the need for covering element 19 with a separate housing. In this case, the only attachment point for tubular access element 19 may be near the tip of scoopula 15 at or near its distal most point, according to one embodiment.

Figure 12:
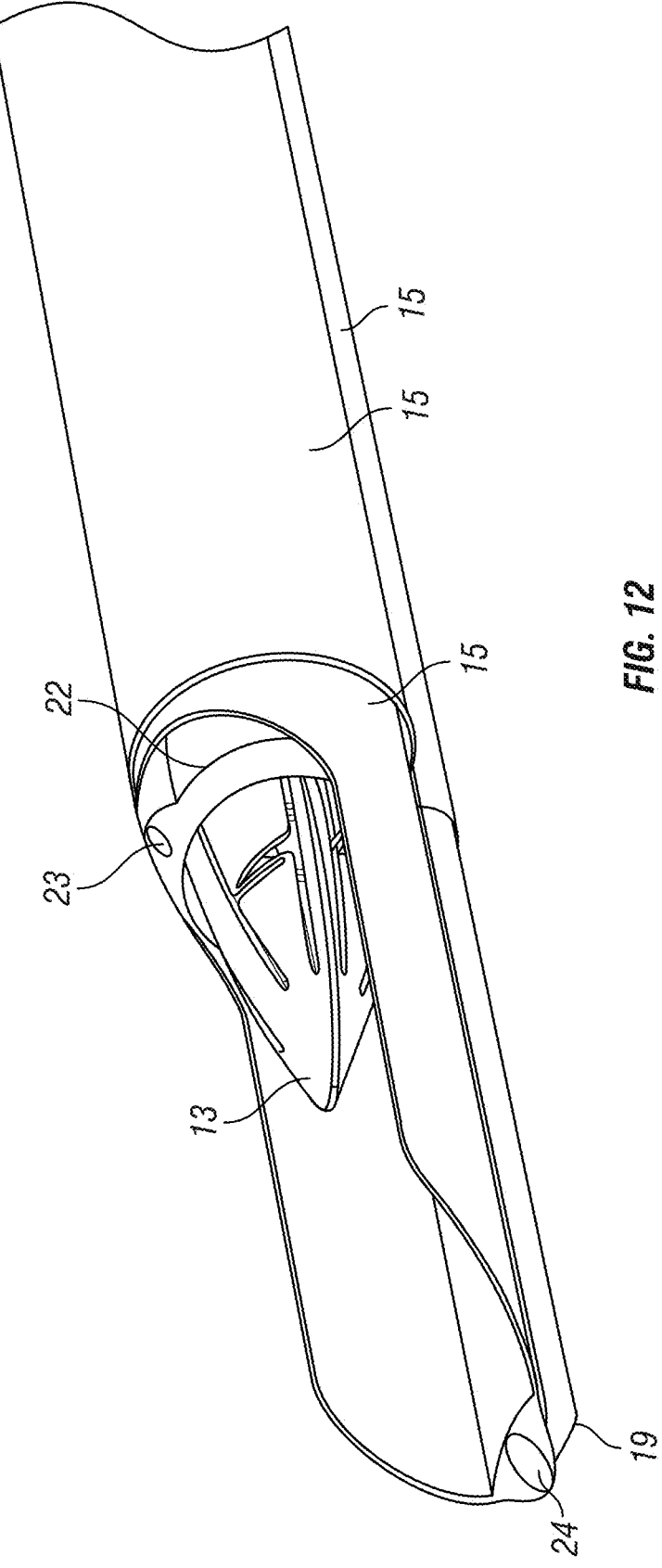
FIG. 12 is perspective view of a device of FIG. 11 of an excisional device, according to embodiments.

FIG. 12 is a perspective view of a work element 13 and other components of an excisional device, according to one embodiment, demonstrating a scoopula 15 constructed with a transparent distal section (forward of its junction with a highly torque-able proximal flexible tubular housing) including its auxiliary tubular access channels 19 and 24 such that non- or differentially rotatable element 22 may, with its own tubular access channel 23 may have full 360 degree viewing capability for full circle vascular wall, according to embodiments.

Figure 13:
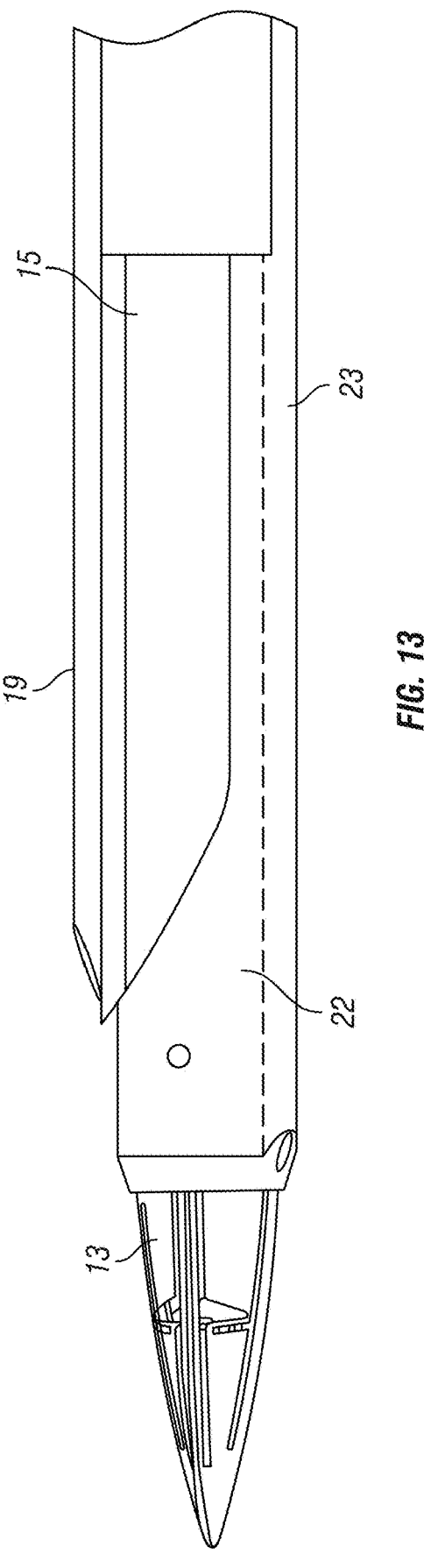
FIG. 13 is a side view of an excisional device of FIG. 10 with one of its components rotated to reveal additional positioning capabilities according to embodiments.

FIG. 13 shows the excisional imaging device of FIG. 1 with its beak elements 13 extended in a streamlined or parting off configuration while in this case scoopula 15 is rotated independently to an upper location where for example a branching vessel may be located and thus protected by the rotated scoopula 15. Similarly, a normal wall of a vessel may also be protected by the shielding effects of the scoopula wall. This location could also be selected to permit closer examination of structures in the wall or in obstructive disease lesions utilizing for example, access lumen or channel 19 through which to introduce imaging devices according to embodiments.

Figure 14:
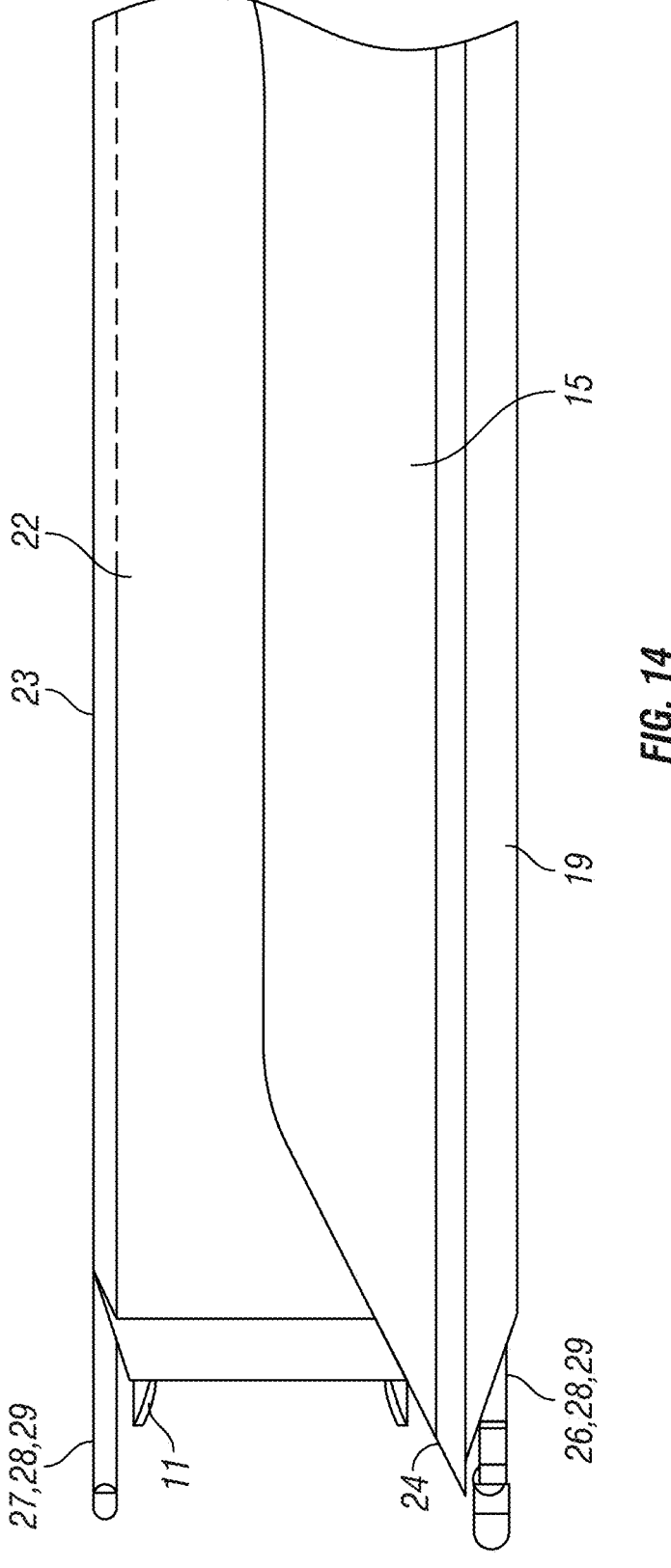
FIG. 14 shows side views of various imaging components of an imaging and excisional device revealing various configurations and positions of these components relative to a working excisional element, according to embodiments.

FIG. 14 shows additional components including various working elements of a device according to embodiments. In this illustration, beaks forward, cutting lips or edges 11 are wide open in an excising or coring position, and covered to a point where minimal exposure of the beak tips by a non- or differentially rotating sheath 22 may enable precise depth control as well as effective coring extending well past scoopula 15 if desired. Also shown are examples of imaging assemblies such as optical coherence tomography 26 as depicted in channel 19, while an intravascular ultrasound imaging catheter or wire is depicted emerging from within access channel 23. Both imaging elements may travel along and just forward of cutting beak tips 11 as shown and according to embodiments. Of note, again channels and imaging components are shown generally to scale according to devices available commercially, as is scoopula 15 and work element beak lip tips 11 and including materials capable of image transmission for such components as scoopula 15. Also, imaging assemblies may be introduced in any of the various available access channels according to the proximity of structures of interest within the body and according to the range and resolution capabilities for imaging catheters. Likewise, flow and pressure sensors 28 or other imaging components and/or associated catheters may be provided and advanced to permit assessment of minimal necessary flow through to sustain tissue viability or reflow after recanalization in cases of totally occluded vessels whether acutely occluded or chronically, as well as for diagnostic purposes in cases of subtotal occlusions and equally, to assess when adequacy of therapeutic interventions has been reached, may be introduced in any of the available channels as may be useful in a diagnostic and therapeutic procedure. Additional components 28 for sensing and ablating aberrant electrical pathways may also be utilized via access channels in the various locations, according to embodiments.

Figure 15:
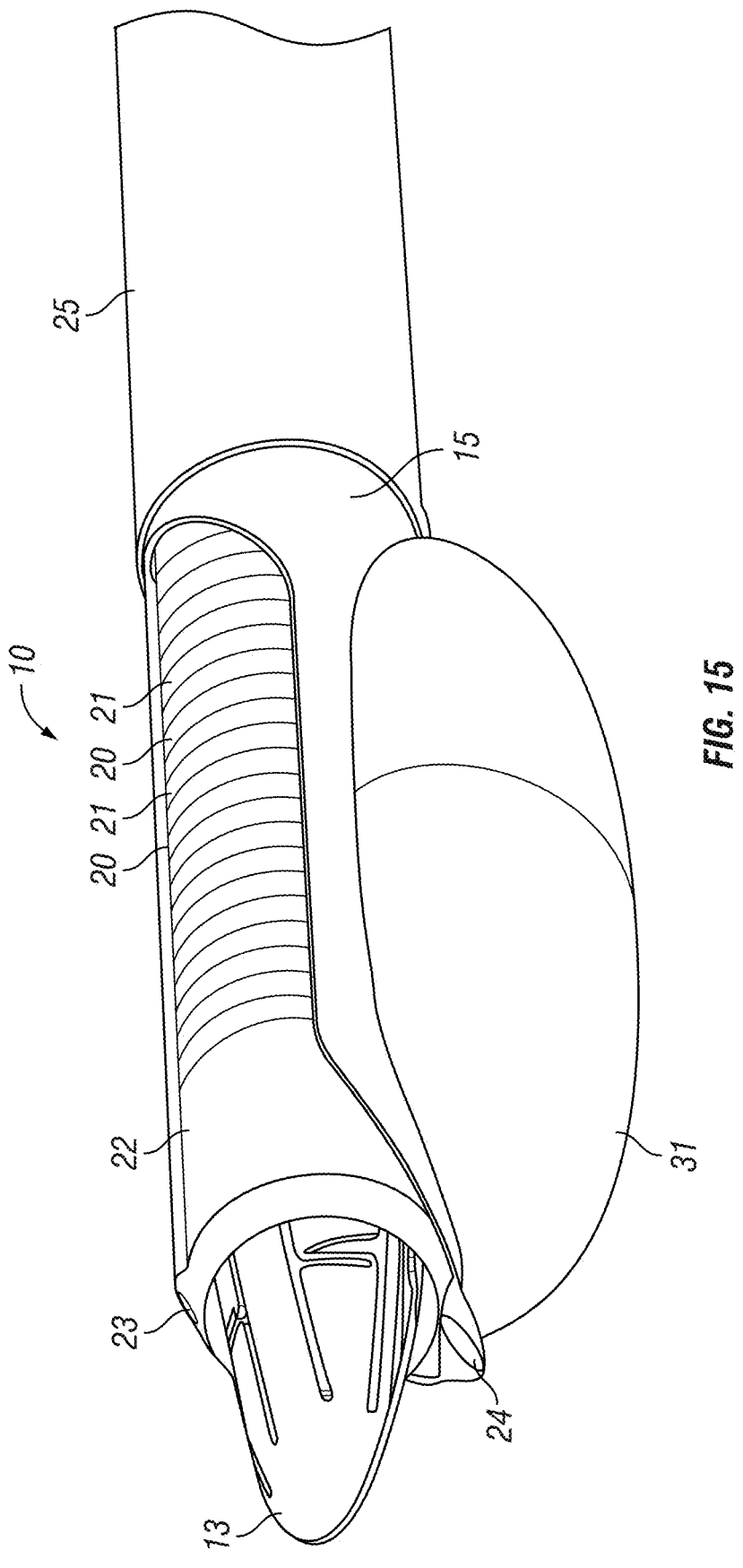
FIG. 15 is a perspective view of an excisional device of FIG. 1 showing an additional expandable element positioned on one side of the device according to embodiments.

FIG. 15 is a perspective view of an excisional device 10 equipped with an expandable element, according to embodiments. In this illustration, the device 10 is equipped with an expandable element 31 such as a balloon along the floor of scoopula 15. Such an expandable element 31 may be operative to urge the scoopula 15 and work element 13 against a diseased vascular wall or to aim work element 13 into an ostium of a branching vessel or both, according to embodiments, while utilizing any of the imaging modalities as may be useful for a specific vascular or other structural tubes or potential spaces, clearing therapeutic and diagnostic assessment, including endpoint determination, procedure. The degree of expansion of such an element 31 may be controllable automatically based on feedback information provided by imaging analysis and safety algorithms, including electrocardiographic information if in coronary vessels, or arterial oxygen saturation if in a pulmonary setting, according to embodiments. Similarly, cycling expansion back down and controlling rotational and degree of extension of, rotatable, extendable scoopula 15 from within and in reference to torque-able outer tube 25 along with rotation for cutting and cycling of work elements 13 during rotation between open and closed beaks, functions to core and part-off tissue for de-bulking and evacuation via a central lumen of the excisional imaging catheter, which may be automated via feedback and control algorithms, for the sake of precision, ease of use and to lessen radiation exposure for interventionists and patients according to embodiments.

Figure 16:
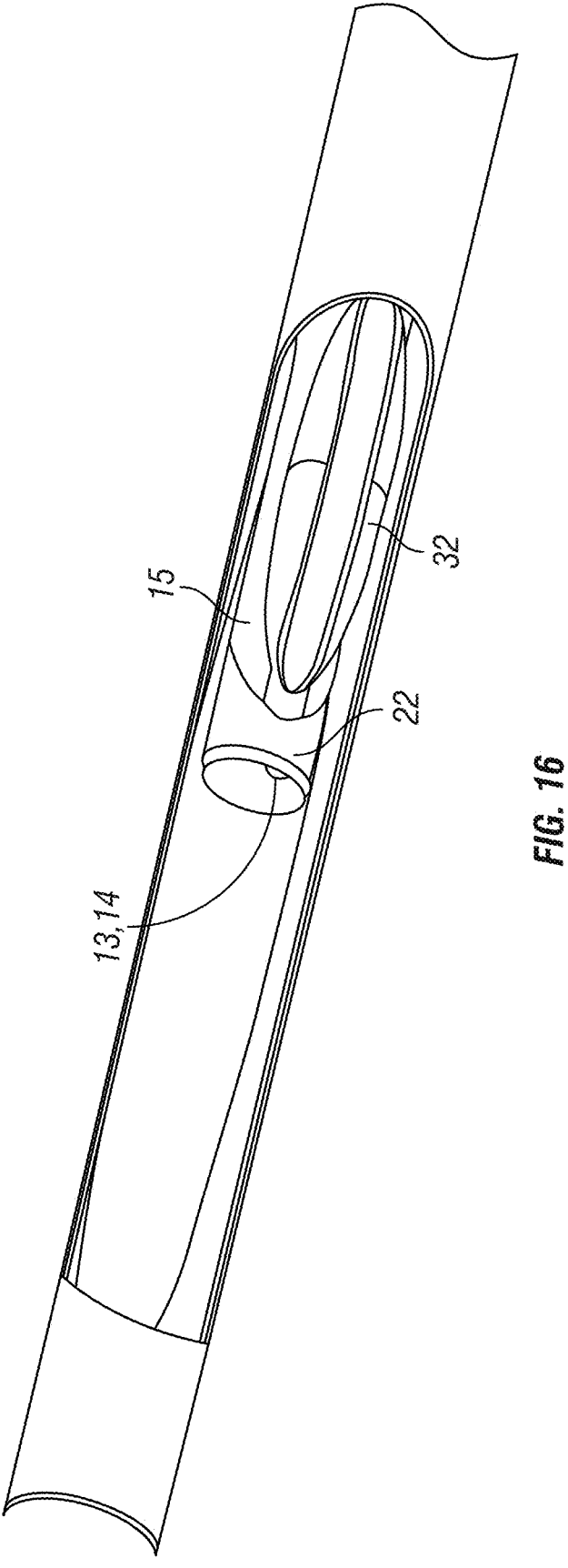
FIG. 16 is a view of a device of FIG. 15 within a cutaway model of a partially obstructed tube such as a blood vessel, further revealing the structure of the expandable element of FIG. 15 according to embodiments.

FIG. 16 shows an excisional imaging device within a cutaway view of a vascular structure with an obstructive partial occlusion being excised by work elements 13 with an additional supporting expandable pontoon shaped structure comprising a central passageway to permit continuous downstream flow during the working phase of obstructive disease removal according to embodiments. Note that each of the expandable elements may be differentially expanded as may be desired and that varying levels of expansion can be used to widen or narrow the flow channel located between the expandable elements for the purposes of optimizing flows according to downstream needs during ongoing perfusion or, in the case of restoring flow, to optimize reperfusion levels of flow according to embodiments.

Figure 17:
FIG. 17 is a side view of an excisional device of FIG. 1 with additional imaging catheters presented emerging from various forward channels ahead of excisional elements as shown and also including an expandable cuff near the proximal portion of the working end of a device according to embodiments.

FIG. 17 shows an excisional imaging assembly comprising an additional expandable cuff 30 located on flexible tube element 25. The expandable cuff 30 may be configured, according to one embodiment, to gently seal off flows distally (proximal to the work element 13 in this view) for a brief period during imaging and or excision procedures. According to one embodiment, the expandable cuff 30 may be expanded up to a point where flows are at a minimum level to prevent ischemia in distal organs while imaging and excisional work is proceeding in the working areas distal to its location. Expandable cuff 30 can be used to vary the downstream flows (by selectively inflating and deflating as needed) such that flushing blood out of the field of certain imaging systems most negatively affected by blood flows such as optimized coherence tomography ("OCT") can easily keep up with the flows permitted by the upstream expandable cuff 30, and furthermore the level of permissible reduction of flows to keep distal tissues well enough supplied, can be balanced according to physiologic monitoring, which may be controlled automatically to minimize operator work load and improve patient safety, according to embodiments.

Figure 18:
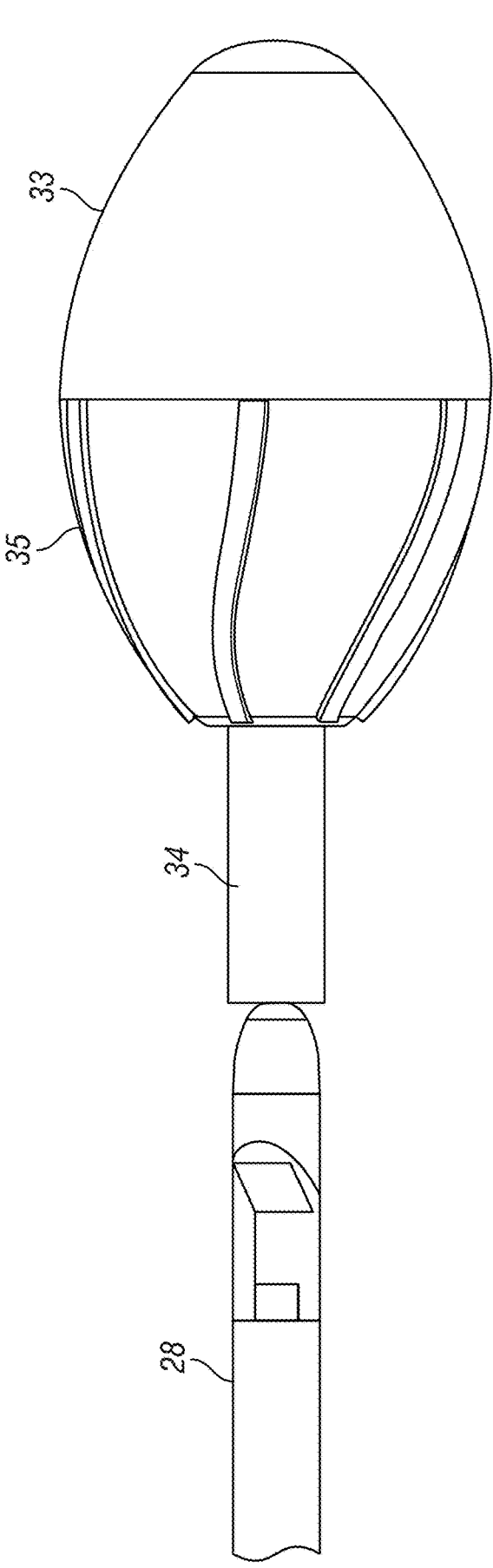
FIG. 18 is a side view of an expandable imaging chamber into which an imaging device may be introduced as shown lined up for entry via an integrated lumen according to embodiments.

FIG. 18 illustrates an expandable, transparent imaging chamber 33 that may be filled with gas or liquids to optimize imaging using, for example, OCT instruments by excluding distorting fluids such as blood, without necessarily limiting downstream flows given that the chamber may remain smaller than the available lumen of the vessel in which it is being deployed, and as is further described in various illustrations herein, may be positioned against an area of interest, leaving nothing between the tissues being studied and the imaging catheter other than the imaging chamber. This view serves to show various components of such a chamber including a central lumen 34 through which various imaging catheters or imaging wires and the like, represented in this case by an OCT catheter 28, may be advanced and deployed as desired. Also shown are blades 35 that may be expanded along with the chamber, which may serve as parting-off structures when used in concert with excisional elements (e.g., beaks) 14 (not shown in this illustration), according to embodiments.

Figure 19:
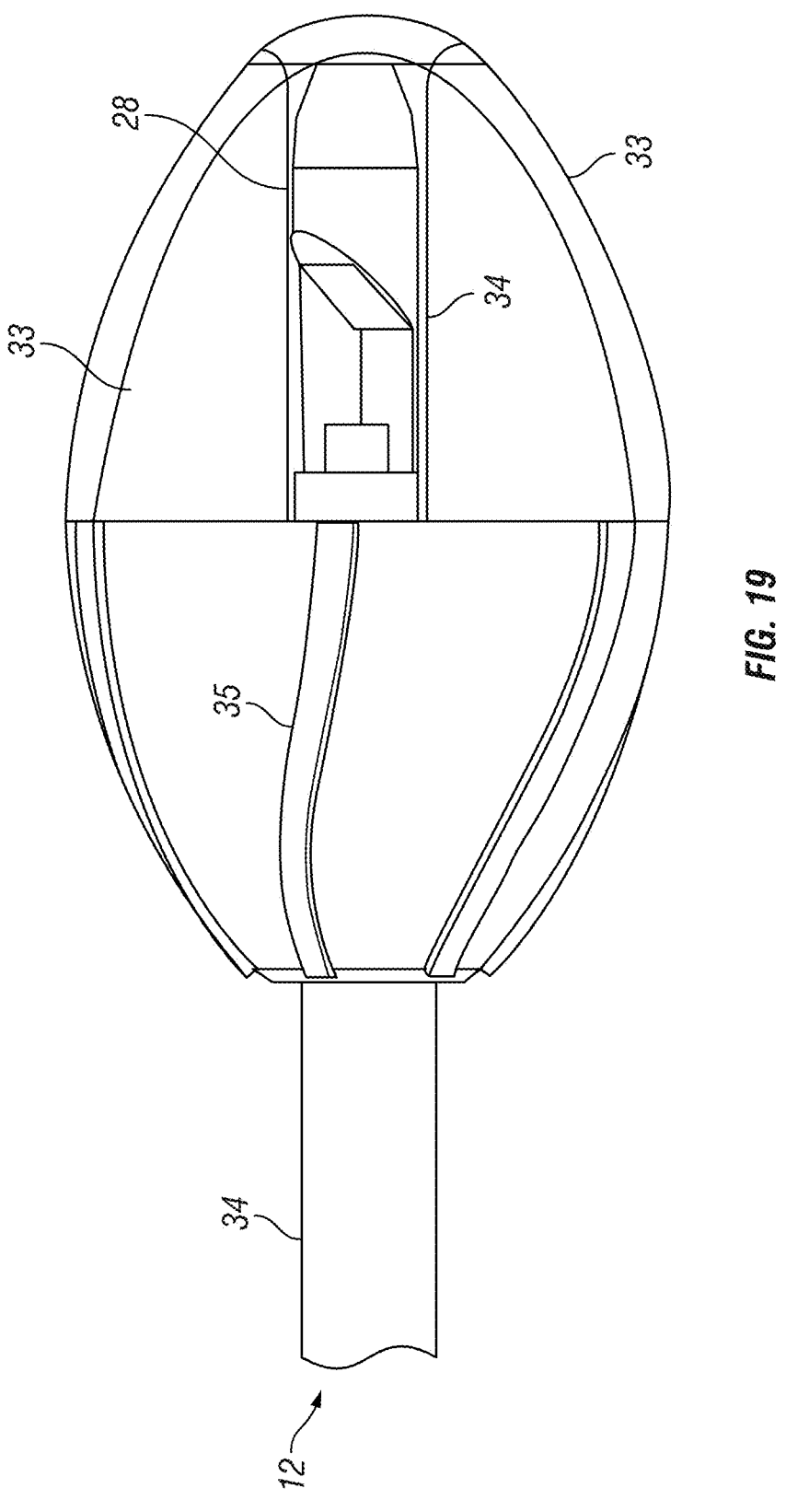
FIG. 19 is a side view of an expanded transparent imaging chamber with a forward portion of the chamber cut away to reveal an imaging element located internal to the chamber within an additional, likewise transparent lumen as shown according to embodiments.

FIG. 19 shows a closer view from the side of the same elements of FIG. 18, with in this case, imaging element 28 already advanced all the way to the forward surface of expandable, imaging/parting off transparent (to the selected imaging modality) chamber 33 with its blades 35 providing a sharp edge against which a spinning work element or elements such as beak cutting element edges 14 may completely sever diseased tissue from its attachments to a vascular wall without needing to bend for parting off, according to embodiments.

Figure 20:
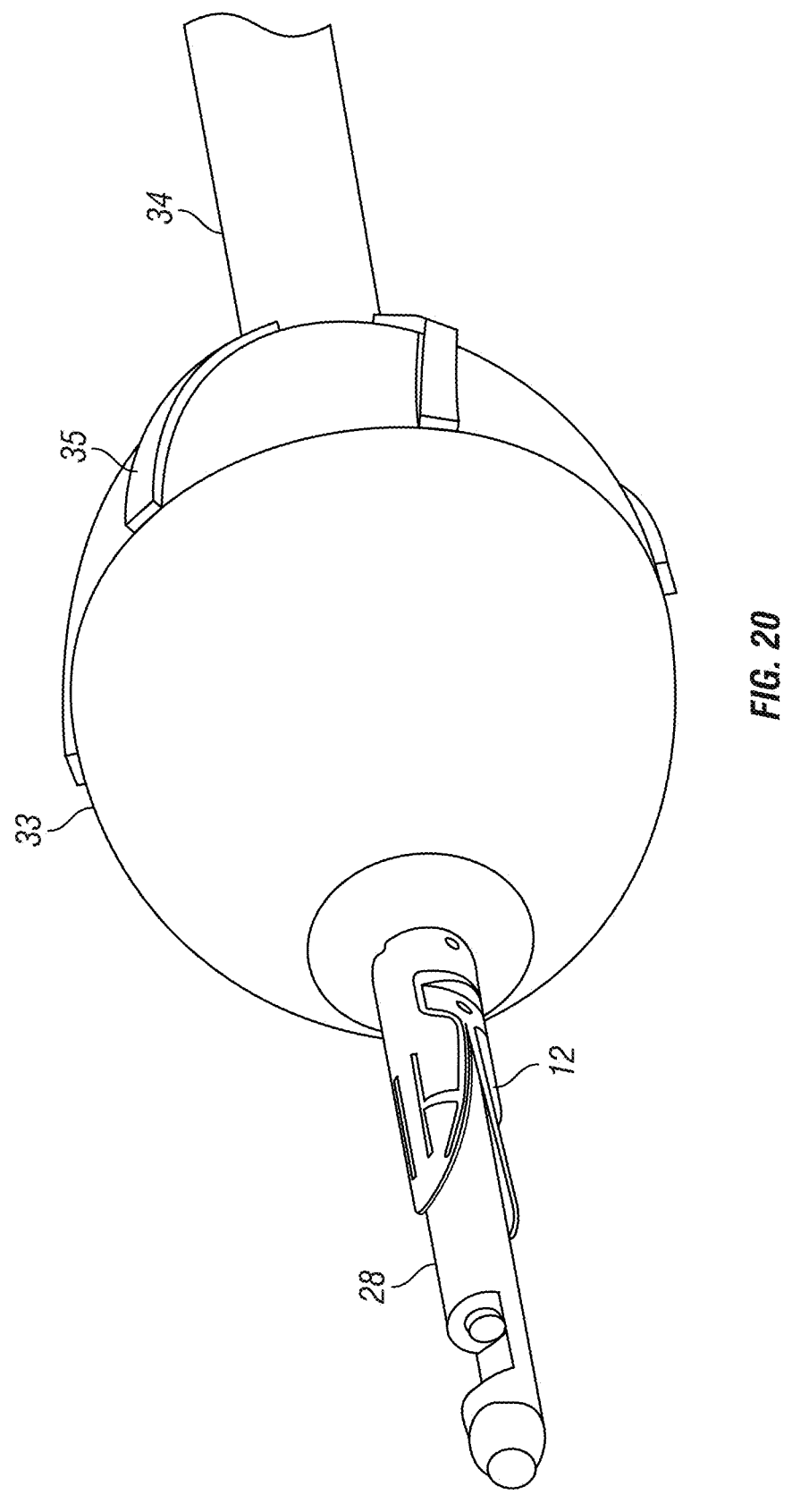
FIG. 20 is a perspective view showing an expandable, imaging, parting off, focusing, transparent lenticular chamber or tandem chambers, emerging through and from within which is an excisional work element of a device, itself within which excisional device an additional example of an imaging device is shown, according to embodiments.

FIG. 20 shows the elements and assemblies of FIGS. 18 and 19, configured with imaging, focusing, isolating, centering (in this case) chamber 33 with an imaging catheter 28 extended forward distally ahead of a smaller excisional working element, similar in structure and function to work element 13 discussed previously, but now in a larger gauge size (smaller diameter) and delineated as work element 12 for purposes of distinguishing it from a relatively larger work element 13, as may be the case when imaging a total occlusion within a vascular structure, utilizing expandable cutting and imaging chamber 33 for its stabilizing platform effects, along with imaging capabilities to enable smaller excisional dissecting work element 12 to advance through the center cap or soft thrombus occluding a vascular structure, while avoiding going off track and causing unwanted vascular wall injury in the process, according to embodiments. Such a smaller work element 12 may be seen extending through the central lumen of a larger work element 13 in FIGS. 31, 32, 38 and 39. The advantages of being able to precede a larger coring work element with a smaller coring work element 12 include the ability to provide a pilot hole as a means of creating an initial pathway through an occlusion (for introduction, for example, of guidewires or imaging catheters); centering or anchoring the larger work element 13 for subsequent coring of a larger diameter core; the creation of a small blood flow pathway through an occlusion; and the ability to efficiently core a very hard occlusion cap, which may be highly calcified, It should be noted that the distinguishing nature of work element 12 is that it is smaller than work element 13, and work element 12 may be of any size relative to work element 13 as long as it is able to be introduced to a target work site within the central lumen of work element 13. In such a manner, an occlusion may be initially cored with a very small work element 12 (which may be left in place through the cored occlusion), followed by a second pass with a larger work element 12 over the smaller work element 12 but still being placed within the central lumen of work element 13, and so on, up to the point of a final coring pass through the occlusion using work element 13, as may be desired. It should be noted that this method of crossing an occlusion or thrombus results in a safe and effective procedure for removal of stenotic tissue with a corresponding reduction in potential embolic material being released into the bloodstream, since work elements 12 and 13 represent the distal tip(s) of both coring and transport mechanisms as described herein, and according to embodiments. It should also be noted that work element 12 may indeed be the distal work element of an independent coring device introduced through the central lumen of an excisional device 10 and may be referred to herein as work element 12 or excisional device 12.

Figure 21:
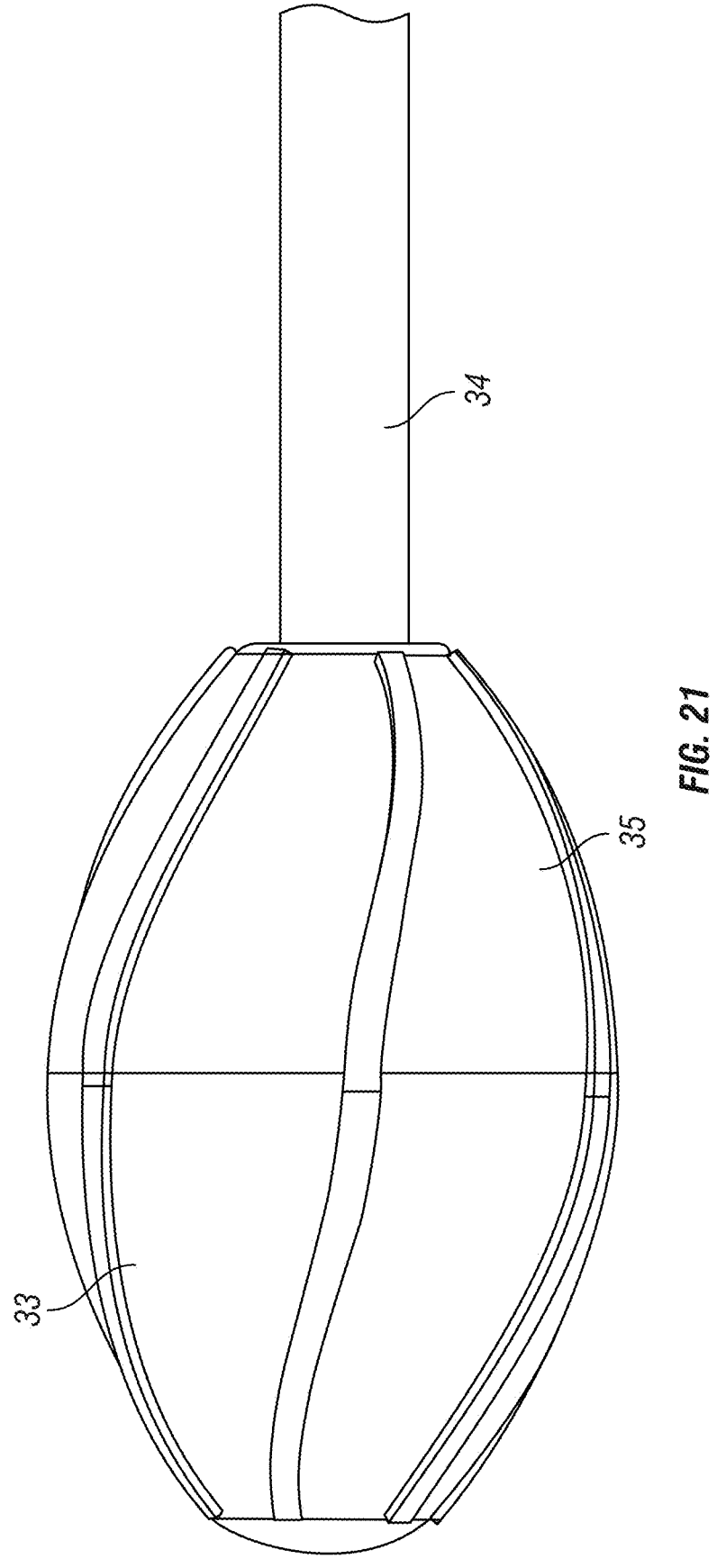
FIG. 21 is a side view of an expandable chamber of FIG. 20 with additional cutting elements located along the forward hemisphere according to embodiments.

FIG. 21 illustrates an expandable transparent imaging, parting off cutting and excisional element 33 equipped with blades 35 on the forward area as well as the rearward area thereof. Such a device may be used in concert with a variety of assemblies illustrated in several figures such as FIGS. 11, 12, 16 and others, in a variety of positions relative to obstructive lesions in a vessel. The device may be used for forward excisions or rearward excisions as desired and may also utilize its included cutting blades 35 for parting off purposes in conjunction with a coring work element 13 through which it may be inserted, (i.e., the coring beaks of work element 13 could core up against the proximal side of an inflated element 33's blades 35 to part off cored tissue without the need to close work element 13's beaks for parting off cored tissue, as shown if FIG. 27) as well as for trapping and transporting abnormal and excised tissues according to embodiments, while also including imaging instruments within its transparent chamber, according to embodiments. Additionally, element 33 may be introduced to the far side of a lesion through a path bored or cored through the lesion (occlusion or thrombus) by a work element 12 or larger work element 13, as an example, and thus element 33 may be used to additionally ablate specific regions of a cored path through the lesion on a backward or forward path through a portion of the cored lesion.

Figure 22:
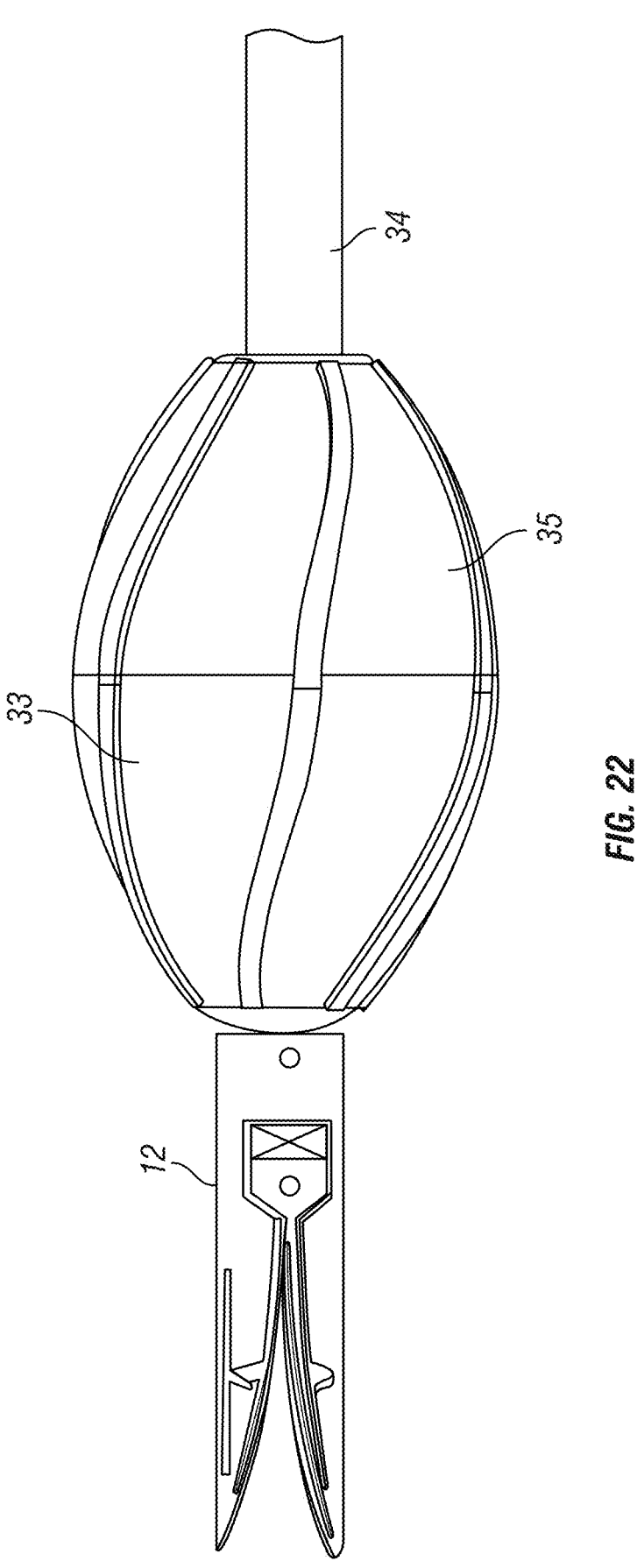
FIG. 22 is a side view of a device of FIG. 21 with an additional excisional device at the forward end of a more proximal expandable device according to embodiments.

FIG. 22 shows the same components and work elements of FIG. 21, shown here with the introduction of smaller excisional element 12 via central lumen 34 which, though not shown here, may be separate from an inflation/deflation tube that may be attached to the transparent, expandable imaging, cutting chamber 33 with its cutting blades 35, according to embodiments.

Figure 23:
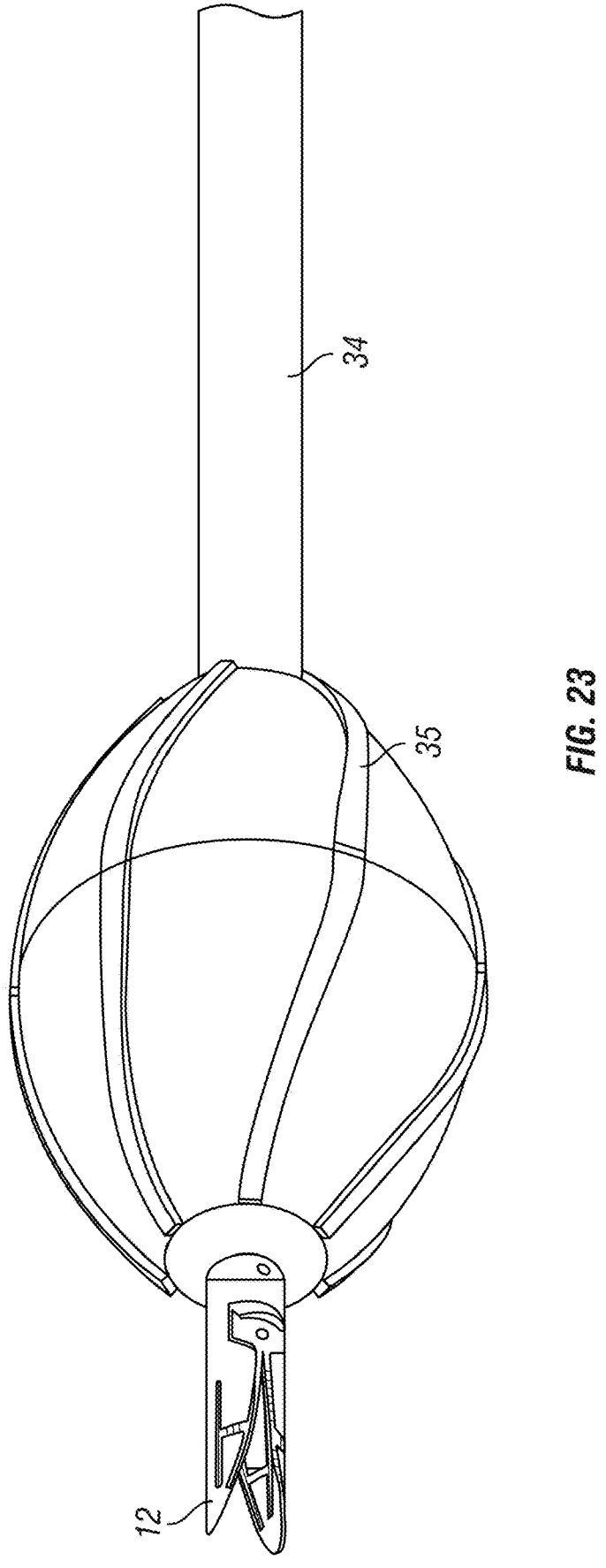
FIG. 23 is a perspective view of an expandable chamber of FIG. 22 with an excisional device at the forward end according to embodiments.

FIG. 23 shows, in perspective view, the elements previously illustrated in FIG. 22 and others, in detail, and again demonstrating parting off elements or blades 35 of expandable imaging chamber 33, according to embodiments.

Figure 24:
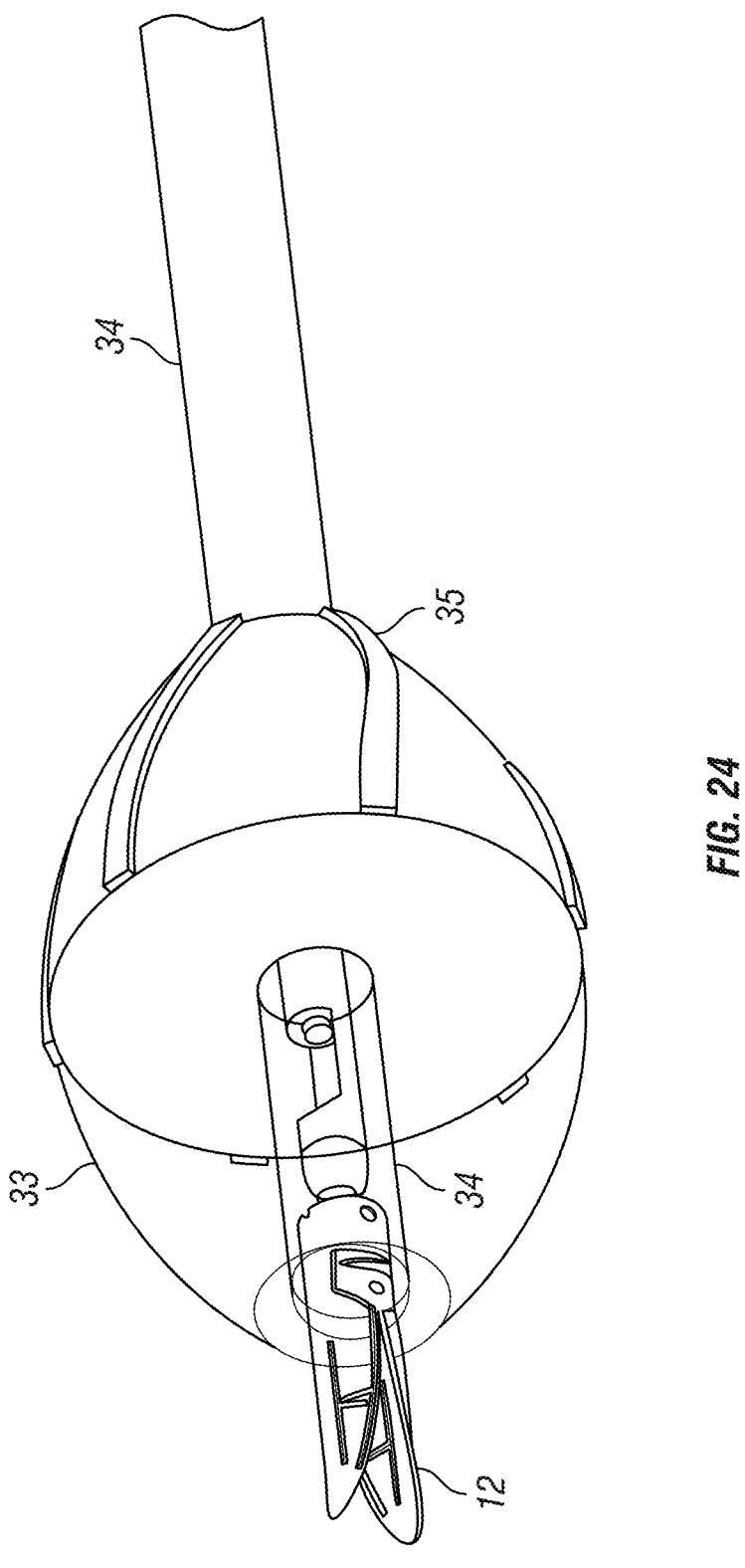
FIG. 24 is a perspective view of an assembly of FIGS. 20 and 21 with the forward portion of a transparent chamber shown as a transparency revealing an imaging element not yet advanced fully through the excisional work element of FIG. 20, all of which may be utilized in an excisional device of FIG. 1 according to embodiments.

FIG. 24 shows in perspective view, further details of transparent imaging, expandable, cutting and chamber 33, provided with a distally-disposed small excisional element 12. Close behind the small excisional element 12, is an imaging element showing that the two may be used sequentially or in concert initially and at various stages of a procedure such as to penetrate a hard cap of a chronic totally occluding plaque for example in an arterial structure, according to embodiments.

Figure 25:
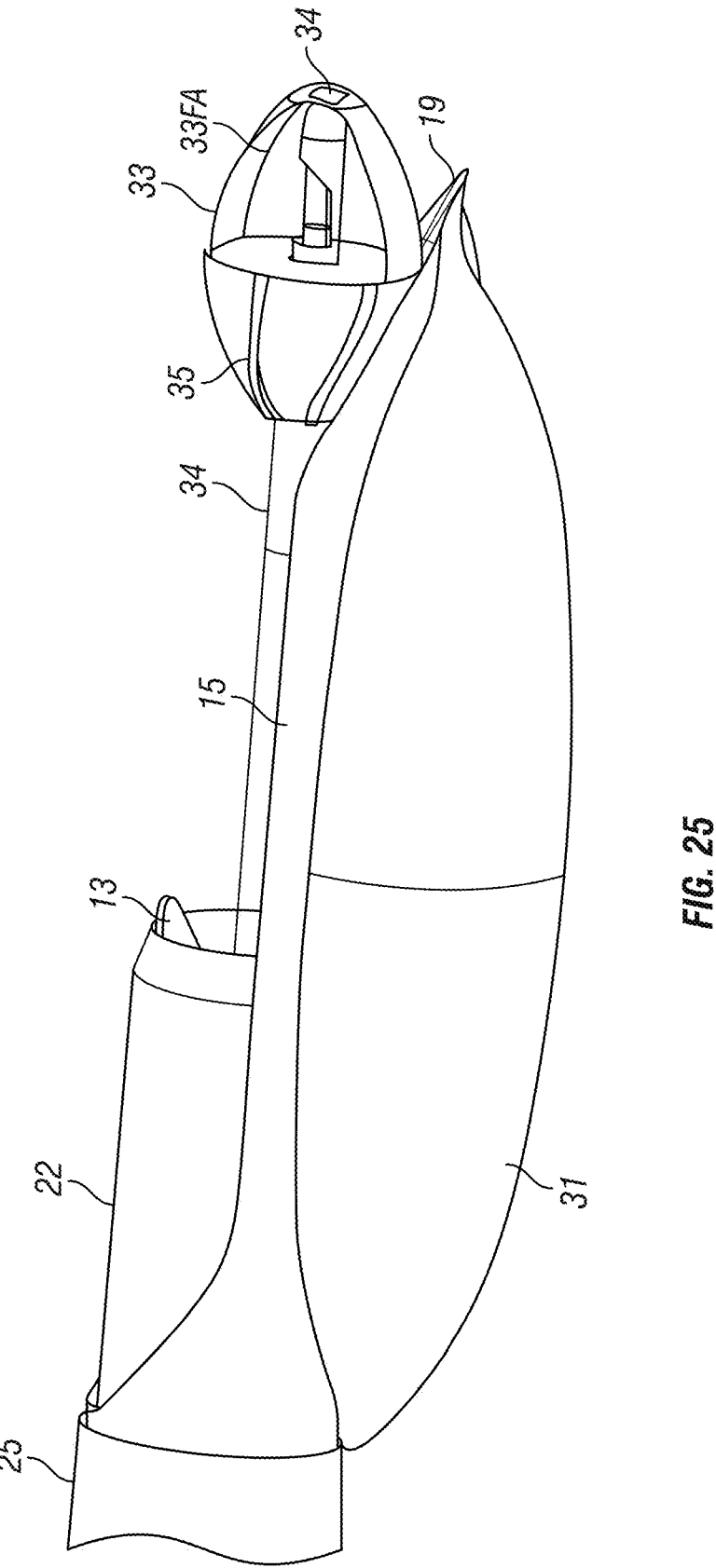
FIG. 25 is a perspective view of an assembly including an excisional device of FIG. 15 and an imaging chamber of FIG. 24 in position according to embodiments where these are used together as shown according to embodiments.

FIG. 25 is an illustration of elements of a combined imaging, excisional and disease evacuating device 10 according to an embodiment. Shown therein are a working dissecting and excisional work element 13, a non- or differentially rotating flexible sheath 22, an extendable, rotatable scoopula 15, with one example of a variety of access channels 19, an expandable imaging chamber 33 with its controlling central lumen 34, a side supporting expandable single lobe balloon element 31, a flexible proximal outer tube 25, according to one embodiment.

Figure 26:
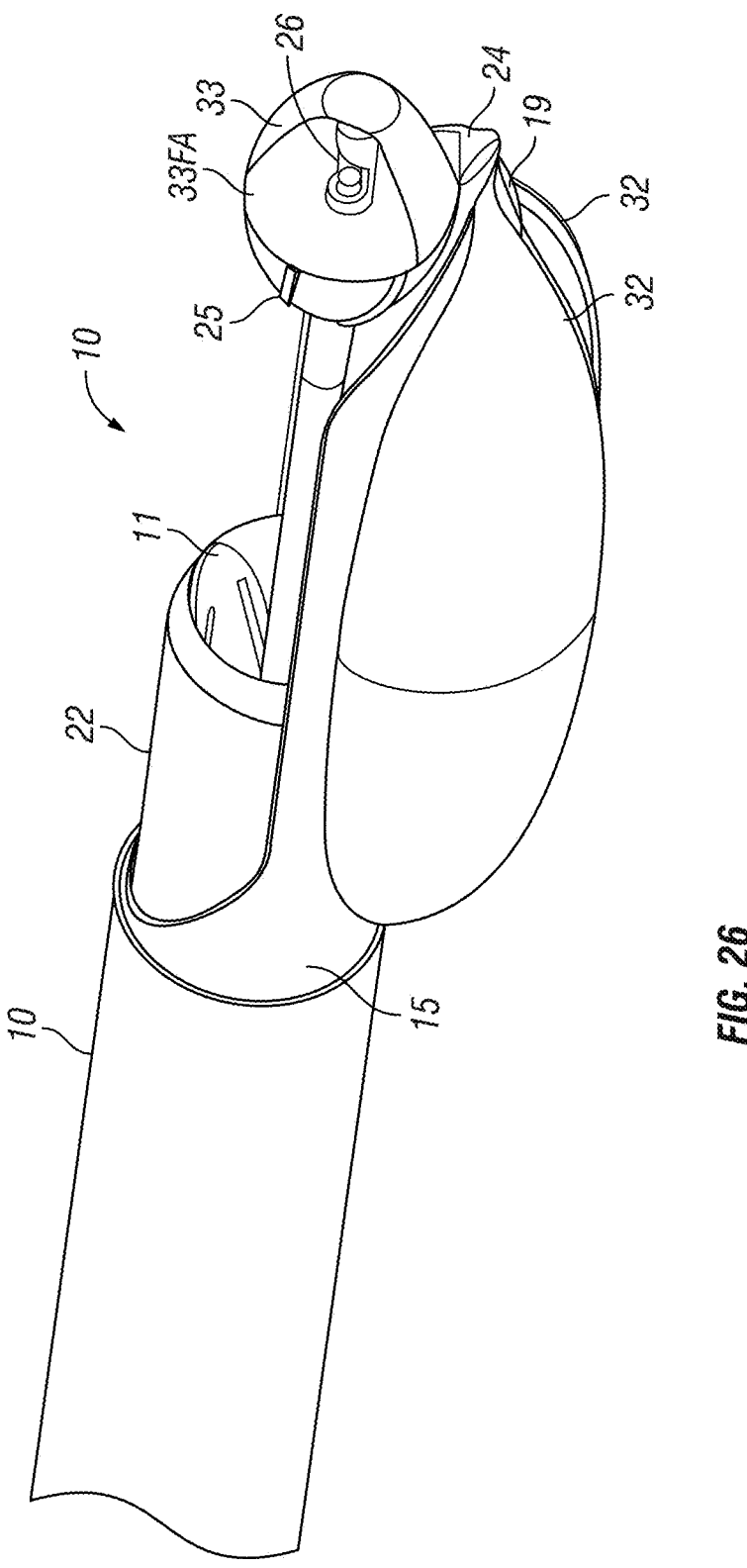
FIG. 26 is a perspective view of an assembly of FIG. 25 again showing an excisional element in partial forward excursion with beaks open in coring mode, according to embodiments.

FIG. 26 is a view of an excisional imaging assembly 10 with scoopula 15 supported by a double, flow-permitting expandable pressing structure 32, various access channels and lumens such as 19 and 24 as well as a beak lip or cutting edge 11 seen protruding slightly from the forward edge of non- or differentially rotating sheath 22. Also deployed is an expandable, transparent imaging, chamber 33 with its forward focusing area 33 FA indicated with an internally placed OCT imaging device in the distal portion of imaging chamber 33, which is itself located distally in the forward portion of scoopula 15. In this case, parting off could be carried out by the blade edge(s) against parting off blades 35 as may be desired according to embodiments. Also, although in-situ imaging capabilities are emphasized throughout for precision control of depth and positioning of excision passes, as shown in this illustration, the simple act of expanding element 33 in the trough of scoopula 15, enables automatic depth limitation of excisional elements 14 between NRS 22 and imaging chamber 33, according to embodiments. A simplifying mechanism of depth control is enabled by balancing forces of expansion between expandable structure 32 and expandable imaging chamber 33, while referencing imaging landmarks. For example, when the desire is to core only diseased tissues while leaving deeper vascular wall layers intact, without removal, invasion or any other type of damage, then a virtual on-screen line could illustrate the imaging chamber's nominal expansion circumference, regardless of its current state of expansion. When the imaging chamber 33 and opposing pressing structure(s) 32 are expanded to set the virtual nominal line on the desired depth of tissue removal, the blades 11 could then automatically core to that depth and no further, because the tissue that is blocking or partially occluding a vessel generally projects into the vessel lumen and the endpoint is most favorably reached, when the obstructing tissue is removed, while leaving deeper vessel wall layers unharmed by overly aggressive tissue removal. If the chosen in-situ imaging modality happens to be OCT (optical coherence tomography), then viewing chamber 33, with its transparent medium, also automatically provides a downstream vessel, non-flow limiting, yet OCT transmissible, pathway to the vascular wall disease areas of interest. The aperture angle for imaging (given blood obscures OCT imaging), can also be controlled by the degree of chamber 33 flattening against the diseased vascular wall. The other components needed for this type of exercise include the control and imaging structures in FIG. 26 along with imaging displays (not shown in this figure) that enable reference designations to match up with physical depths of tissue removal, including the margin of standoff provided by the opposing balance of forces between elements 32 and 33, which in turn are enabled by the nature of the specific construction of the open ended, yet side coring and thus depth controllable, elements shown in this and subsequent figures, which as opposed to side-only cutting or forward-only cutting, have the inherent ability to directionally core beyond the diameter of the proximal housing (the limitation of side-cutting only devices whose forward end is not open, i.e. does not incorporate an open ended scoopula), yet remain capable of depth limitation and directionality not afforded to forward-only coring devices according to embodiments. As written in other areas, this capability is highly adaptable to automatic depth and directional control according to machine learning algorithms that can speedily cycle through a sequence of cuts that could clear a vessel of obstructive disease that may be (almost always is) asymmetrically distributed along vessel walls, always referencing deeper layers (may be readily identified and automatically referenced with machine learning algorithms) to avoid cutting, according to embodiments. This concept appears again in FIG. 54 where in-stent regrowth of obstructing tissue may be systematically, safely (referencing the metallic struts to avoid damaging in this case) and efficiently removed according to further embodiments.

Figure 27:
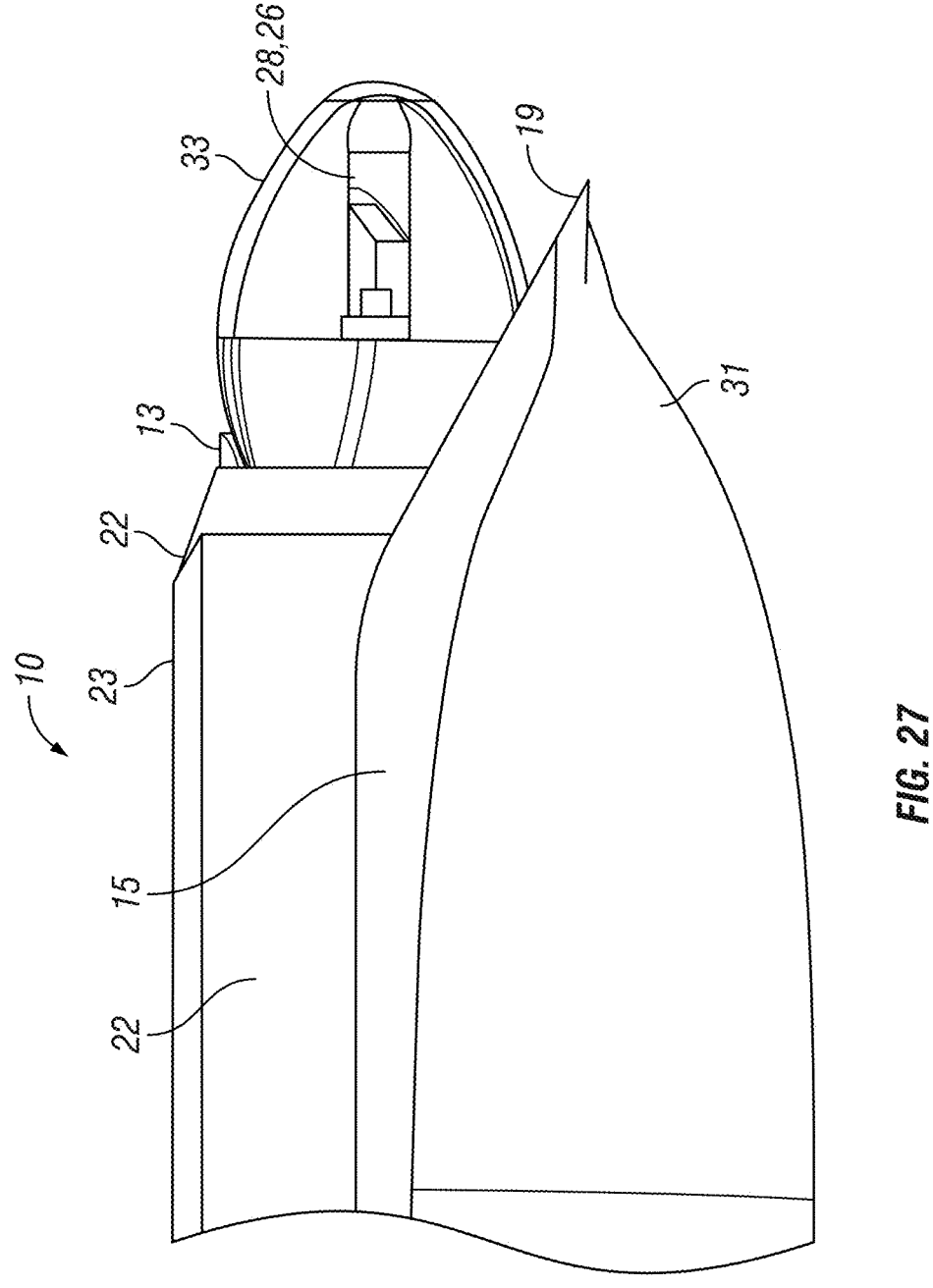
FIG. 27 is a side view of an assembly of FIG. 26 with the excisional element in full forward excursion as limited by imaging parting off chamber of FIG. 24 according to embodiments.

FIG. 27 is a side view of the excisional imaging assembly 10, showing the cutting elements of work element 13 fully open pressed and rotating against the rear edge of an expandable, transparent, imaging chamber 33 in order to part off cored tissue without having to close the beaks of work element 13. Chamber 33 is also shown with an inner OCT device inside its central lumen, the entire apparatus being supported by expandable element 31, according to embodiments.

Figure 28:
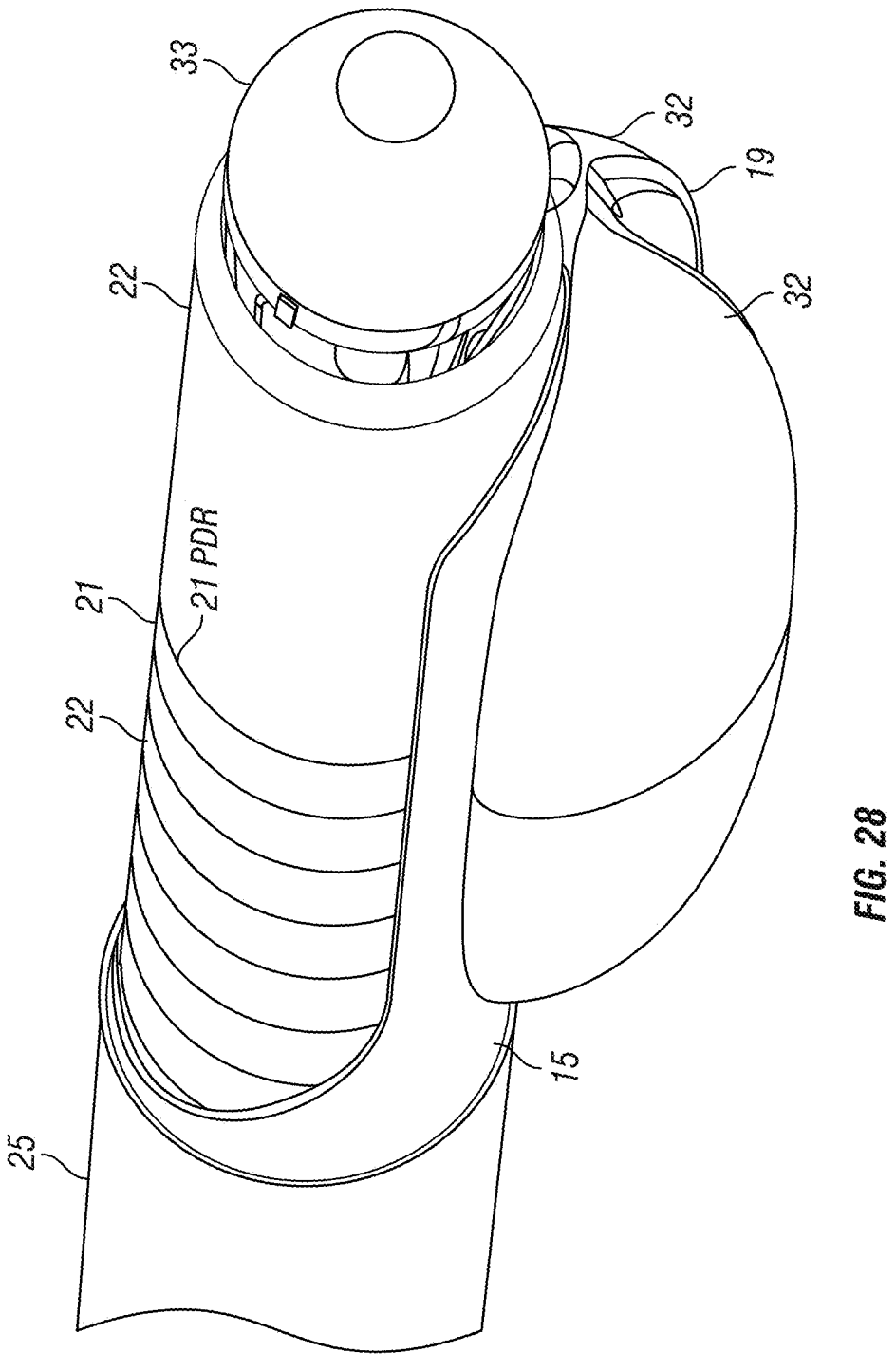
FIG. 28 is a perspective view of a device of FIG. 27 according to embodiments.

FIG. 28 is a head-on view of an excisional imaging, collecting and transporting device 10, each element which may be introduced and rotated into proper position within a vessel with a highly torque-capable outer flexible tube element 25, in this view, showing a position of cutting elements from an excisional assembly for example, as previously described and illustrated, against the rear portion of an expandable imaging, transparent chamber 33 according to embodiments. In this view, a variably open channel between the double, expandable supporting element 32 is also visible and according to embodiments, when this space is completely closed off, tubular access channel 19 may also be utilized to provide downstream flow.

Figure 29:
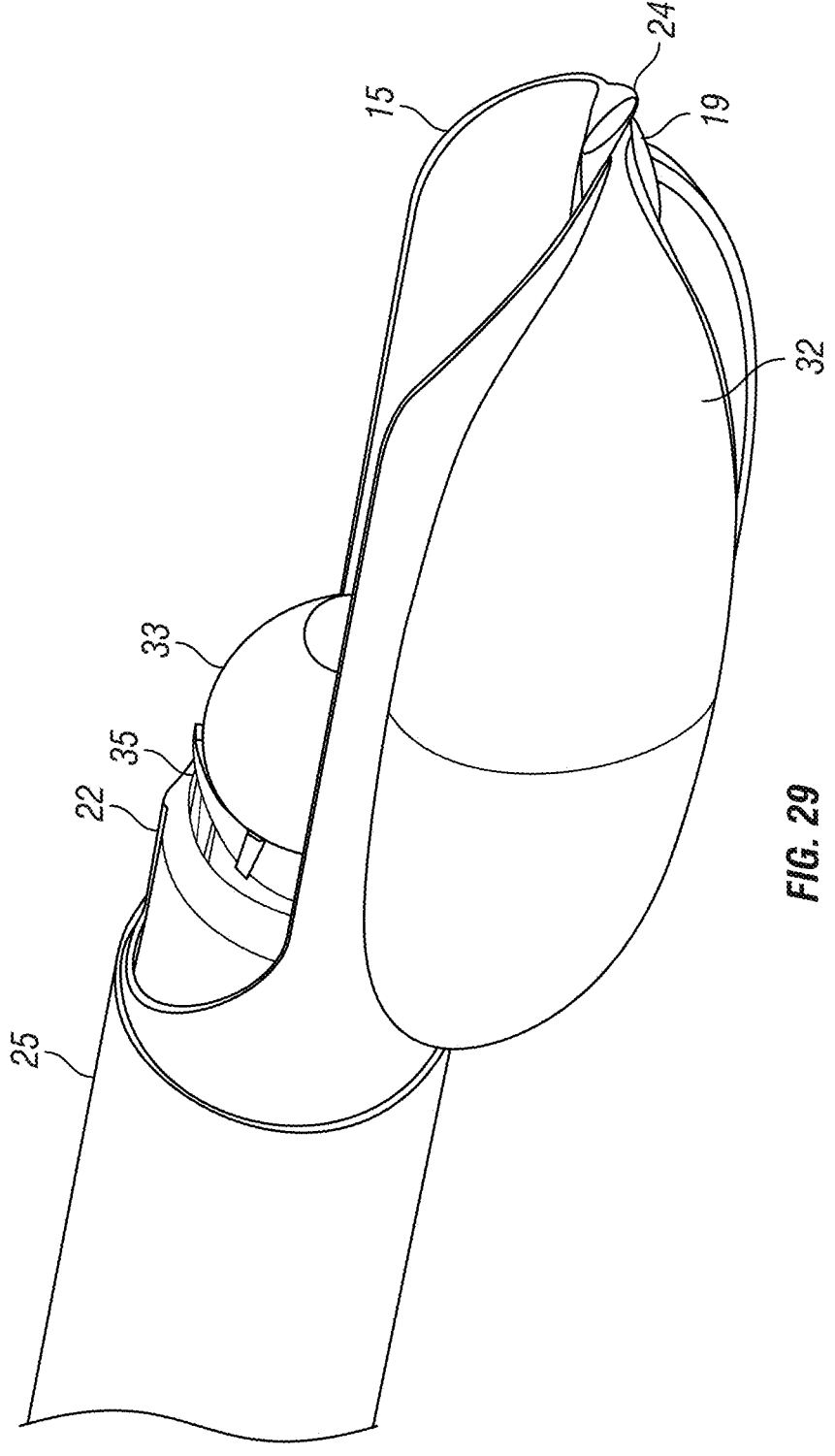
FIG. 29 is a perspective view of an assembly of FIG. 25 now illustrating retraction of imaging or parting off chamber of FIG. 24 in concert with excisional element of FIG. 15 to a proximal position that may be retracted further according to embodiments.

FIG. 29 shows the same elements in an imaging and excisional device 10, however in this case expandable, element 33, which may also function as an imaging chamber, is shown retracted back along scoopula 15 together with excisional elements that would have excised and parted off abnormal obstructing tissues using the rear side of element 33 with its cutting blades (not shown in this view). In this rearward position, tissue parted off and closed off from escape would then be in position for rearward storage within outer tube catheter element 25 or drawn fully rearward (proximally-directed) to transport obstructing tissues out of the entire assembly through the central lumen of the supporting flexible outer catheter 25, according to methods and embodiments.

Figure 30:
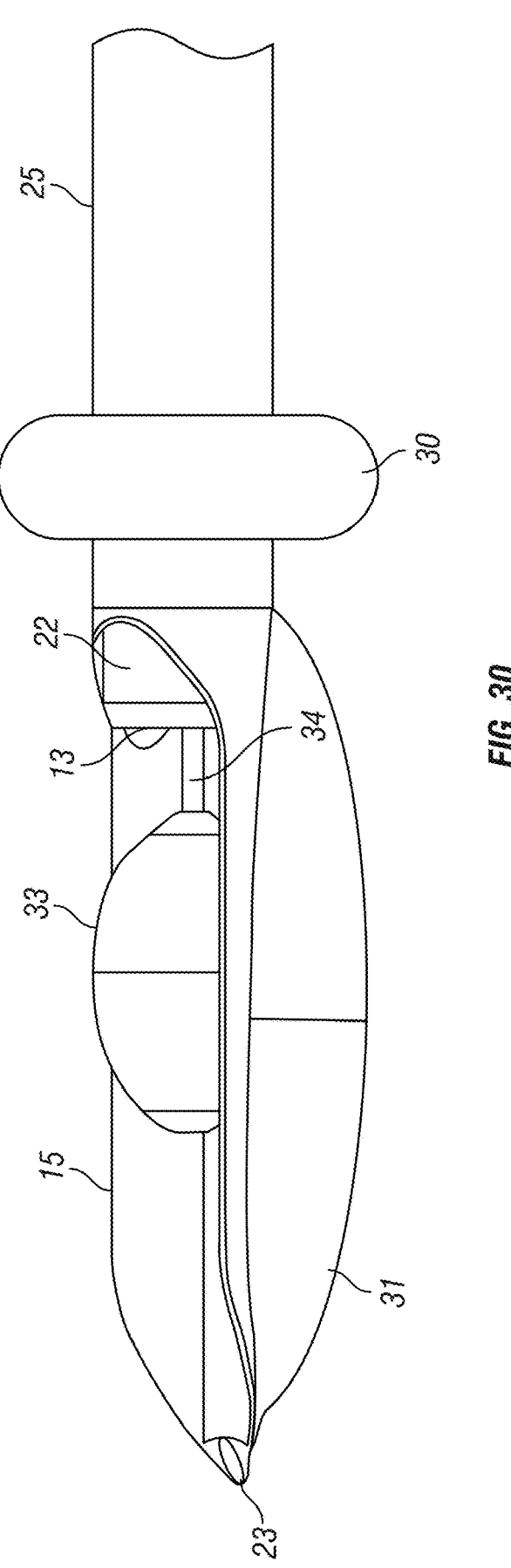
FIG. 30 is a perspective view of an excisional assembly of FIG. 29 with an additional expandable cuff element mounted proximal to the excisional area on a device of FIG. 1 according to embodiments.

FIG. 30 shows an embodiment in which an expandable transparent imaging chamber 33 is shown disposed halfway along scoopula 15, supported by its central lumen 34 and clear of main excisional blades of work element 13 In this illustration, excisional elements 14 are shown with a variant of sharp edges with a tip shape that enables parting off of excised tissue even when a tube such as tube 34 is in place where the edges of excisional blades and tips 11 would meet as well as being of a shape that is efficient for excision. As in FIG. 17, on outer tube element 25 is a proximal expandable cuff 30 that may be selectively inflated and deflated to modulate flow beyond its borders, optionally automatically and based on physiologic safety information sources including in a coronary example, electrocardiographic evidence of ischemia, for a variety of purposes already previously described herein including that it may be used as a torque input locker for the outer tube element 25. Moreover, when expanded, the expandable cuff 30 may provide backup support, in its position so close to distal working element(s) 13, such that distal elements may be advanced against any resistance they may encounter, relying at least partially on expandable cuff 30 for backup support and stability. Another use of expandable element 30 may be to limit reflow shock tissue damage by gradually allowing blood to re-enter tissues that may have been subjected to deeper levels of ischemia, again, referencing physiologic indicators manually or automatically, such as electrocardiographic or other, indicators according to embodiments. Also shown is independently movable non- or differentially rotating sheath 22.

Figure 31:
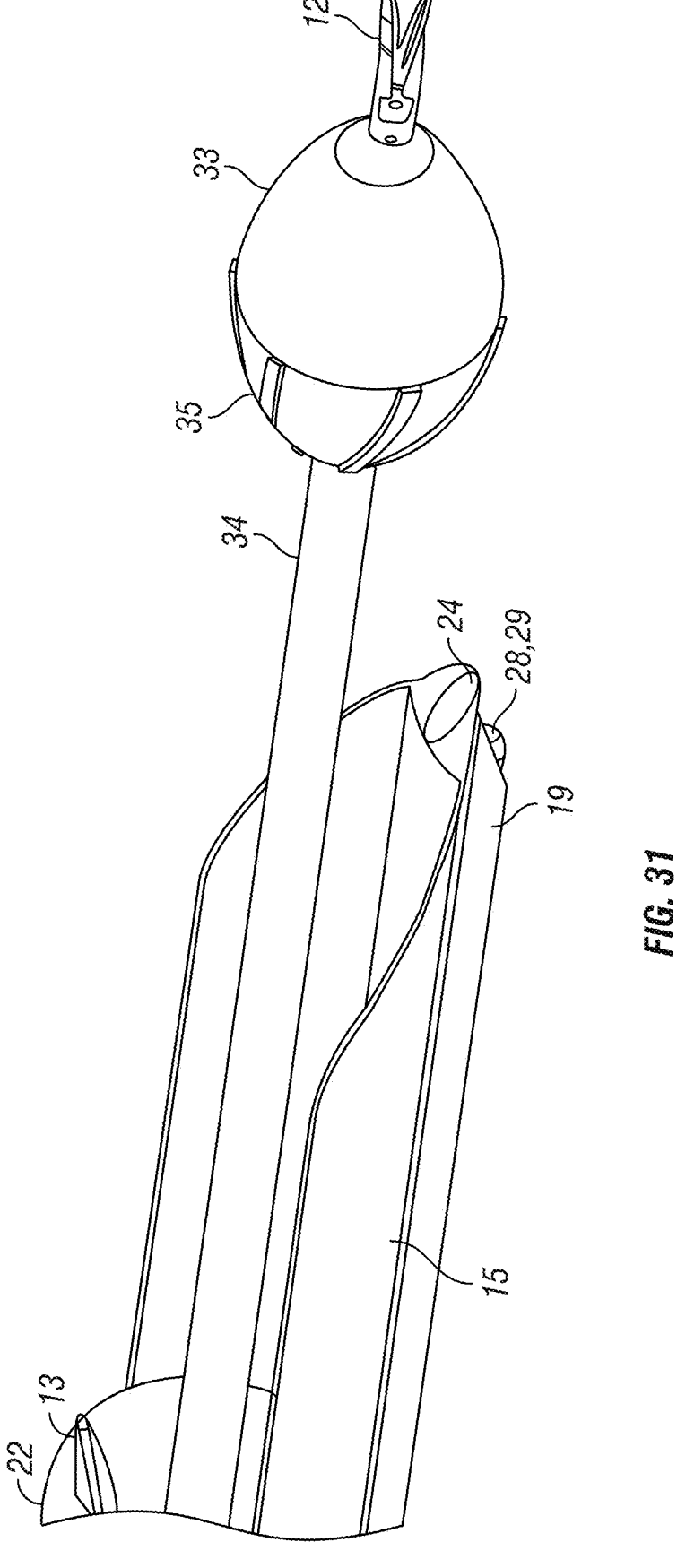
FIG. 31 is a perspective view of an excisional, expandable imaging device of FIG. 29 with one of its excisional elements along with its expandable chamber in an extended position according to embodiments.

FIG. 31 shows that the expandable, transparent imaging, parting off and supporting chamber 33 may be advanced far forward (distally) of scoopula 15 utilizing its controlling hollow shaft 34 through which it was been introduced. A smaller excisional device 12 may be guided in such a distal-most position by its platform 33 from which it emerged if, as in this illustration and according to an embodiment, the smaller excisional device is independently movable. Alternatively, the smaller excisional device 12 may be a fixed component (with respect to axial movement) of chamber 33, notwithstanding (an) actuation connection(s) according to embodiments that allow the smaller excisional device 12 to selectively assume an open, coring configuration or a closed, streamlined, dissection and parting-off configuration. Additionally, in this illustration, beak tips are shown in parting off position around a tube such as element 34. When the beaks are closed in this position, they may also function as a type of carrier bearing that may help provide support and stabilization for shaft 34 and its imaging chamber, which are far forward beyond support from an underlying scoopula. In this case beak tips may compensate for the loss of support that would have been provided by a scoopula 15, when an imaging chamber is advanced beyond its forward edge. Also, tube 34 is capable of rotating as it powers imaging chamber 33. Whether tube 34 is rotating or stationary, surface features such as slots or vanes may be utilized to augment transport of excised materials back through the catheter of FIG. 1's interior. If stationary, the differential rotation of cutting elements 14's inner tube compared with rotation or non-rotation of a tube or shaft 34, given helical element shapes on opposing surfaces of either or both of tube 34 (outer surface) and helical excisional elements rotational tube (inner surface), when rotated in a direction to exert a backwards force on excised tissues, would cause or help cause, backwards transport of excised tissues all the way out the back end of the excisional device of FIG. 1 according to embodiments.

Figure 32:
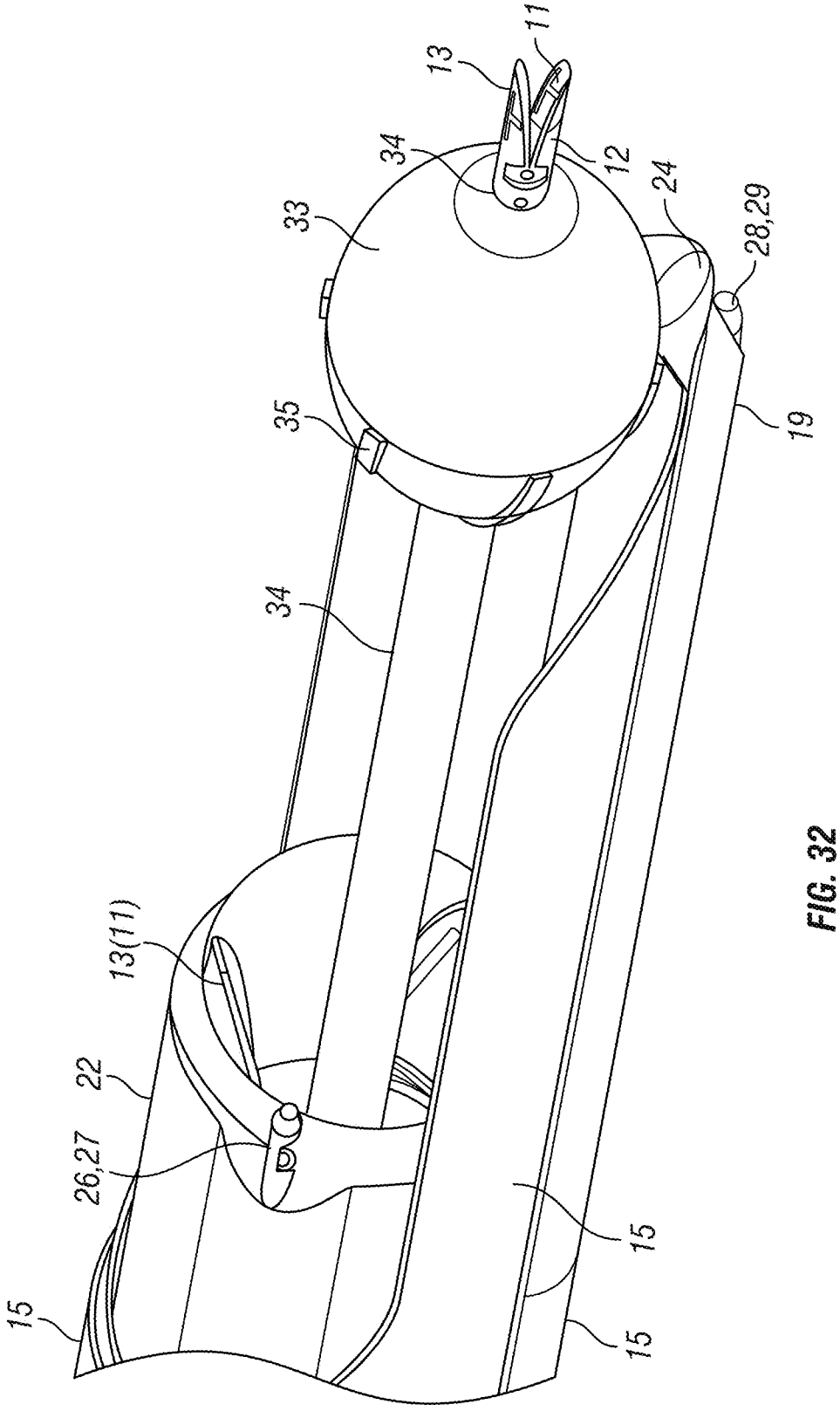
FIG. 32 is a perspective view of an excisional imaging assembly as in FIG. 29 revealing an additional imaging element in approximate alignment with its major excisional element and its expandable parting off chamber with an additional excisional element as well as showing an additional imaging element in an access channel in an approximate plane with its additional excisional element according to embodiments.

FIG. 32 shows the same elements as in 30 and 31, with beaks open and although imaging chamber 33 now has parting off ribbons mounted on its back surface, given the tip shapes 11 of FIGS. 30 and 31, enabling parting off either in the conventional beaks closed manner or against parting off ribbons, an operator has the choice of leaving imaging chamber 33 in any position desired, without needing to move it into a position for parting off excised tissues according to embodiments. Also, FIG. 31 includes, with the addition of examples of a variety of imaging elements 26, 27, 28, 29 and optionally imaging elements inside imaging chamber 33, noting that the positioning of such elements would optimally take advantage of their specific inherent capabilities and physical requirements. Note in this illustration, optional supporting expandable element 32 (not shown in FIG. 32 but present in FIG. 33) may be in non-expanded configuration or, optionally, may not be included in this version of an excisional imaging assembly according to embodiments.

Figure 33:
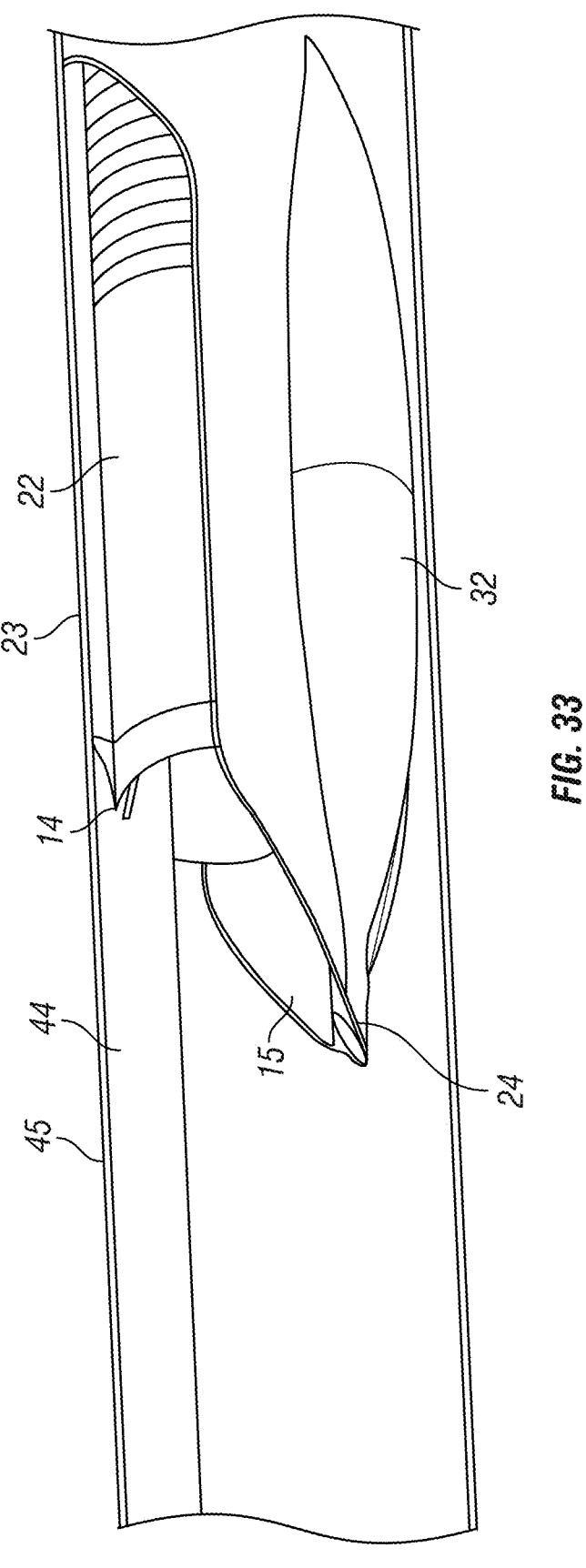
FIG. 33 is a perspective view of an excisional device of FIG. 1 within a vascular structure in the process of excising materials from the wall of a vascular structure according to embodiments.

FIG. 33 and several of the following illustrations show elements of an excisional imaging assembly in action phases within a diseased vessel such as an artery partially obstructed and in some cases totally occluded by obstructing materials 44 that are often located asymmetrically about the internal walls and in most cases form a part of an internal layer of an affected vessel 45. In this illustration, an excisional procedure according to one embodiment involves supporting element 32 of device 10 elevating its scoopula 15 such that excisional elements 13 of working element 14 are able to engage and excise obstructing materials 44 from the vessel 45. Lumen 24 may be utilized with imaging elements to guide the process with a modality such as ultrasound while another imaging modality such as OCT may be utilized at closer range via channel 23 in a non- or differentially rotating sheath (NRS) 22. Note also that NRS 22 may be utilized as a depth limiter depending upon exposure levels of work element 13's articulated beak elements 14s (longitudinal positioning of an NRS near the beak tips 11 or fully back to allow complete exposure of beak elements with the resultant intimate contact between cutting edges and tissues, with no other structure in between) as well as independent rotation of NRS 22 when in position near the cutting edge tips 11 of beak elements 14, such that thicker or thinner areas of an NRS 22 are to a lesser or greater level, between cutting edges and tissues being excised, according to embodiments. Note that both NRS 22 and scoopula 15 may be fully transparent or may have transparent areas according to embodiments.

Figure 34:
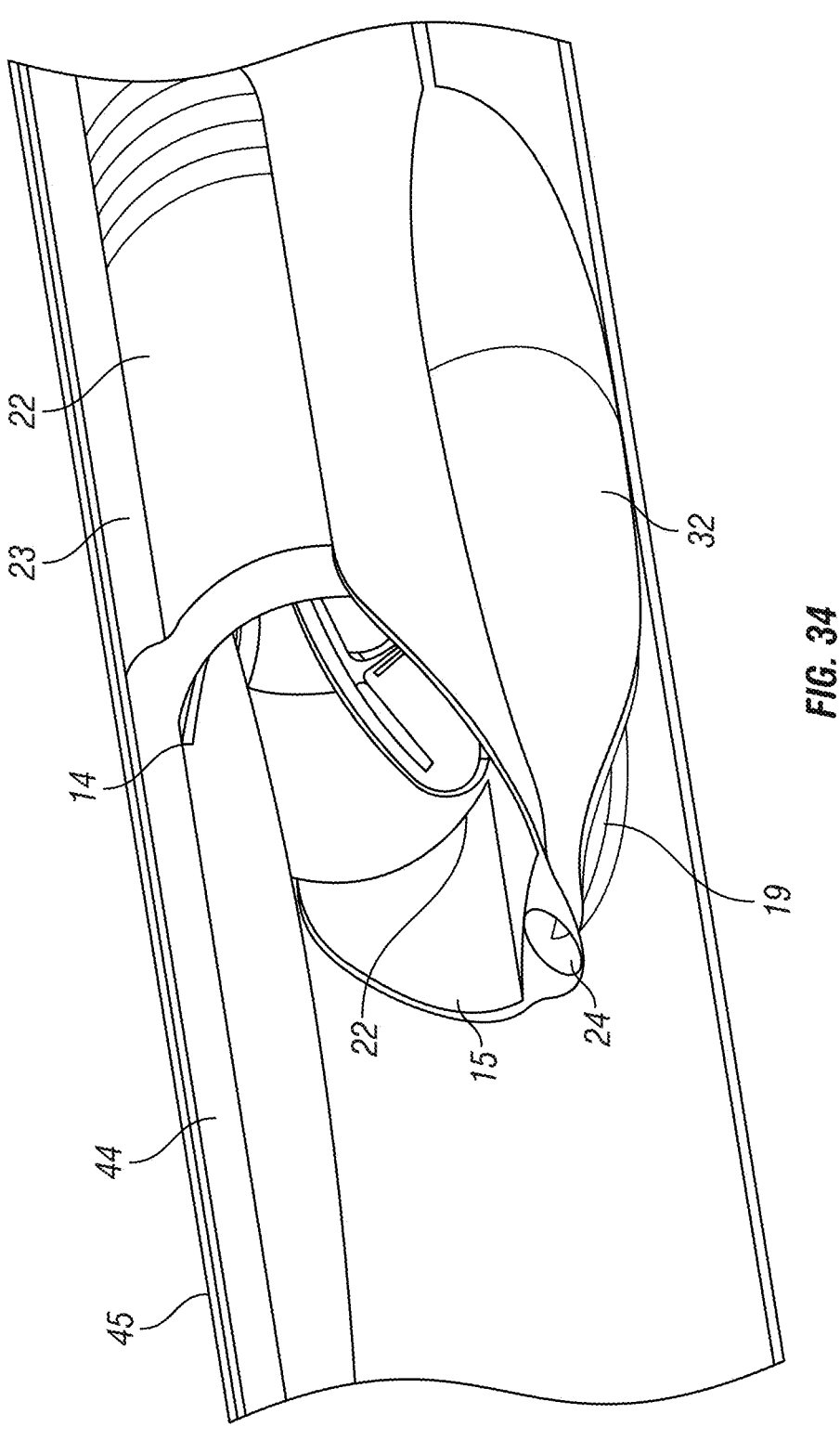
FIG. 34 is a more frontal perspective view of an excisional imaging device of FIG. 33 shown within a vascular space excising obstructive materials and also revealing a double expandable element with a variably opening, longitudinal channel between the individual halves, each half optionally expandable to a different degree one versus the other, located on the underside of a device according to embodiments.

FIG. 34 shows the present device 10, using the same elements as in FIG. 33, is shown from the front to more clearly show elements as the central channel and access or flow lumens 19 and 24 along with lumen 23 as well as the ability to utilize their positions for introducing imaging elements according to each imaging modality's capabilities and limitations. These channels are collapsible, representing potential spaces, or they may be rigid according to embodiments and are considered interchangeable, even within a single procedure and may be utilized by a single modality such as ultrasound, or in combination with physiologic measurers of flow restriction, fractional reserve and fractional flow gain following luminal improvements for such purposes as endpoint analysis, or in combination with other imaging modalities such as OCT. Also shown are the beak elements 14 involved in clearing disease material 44 from a vessel 45, according to embodiments.

Figure 35:
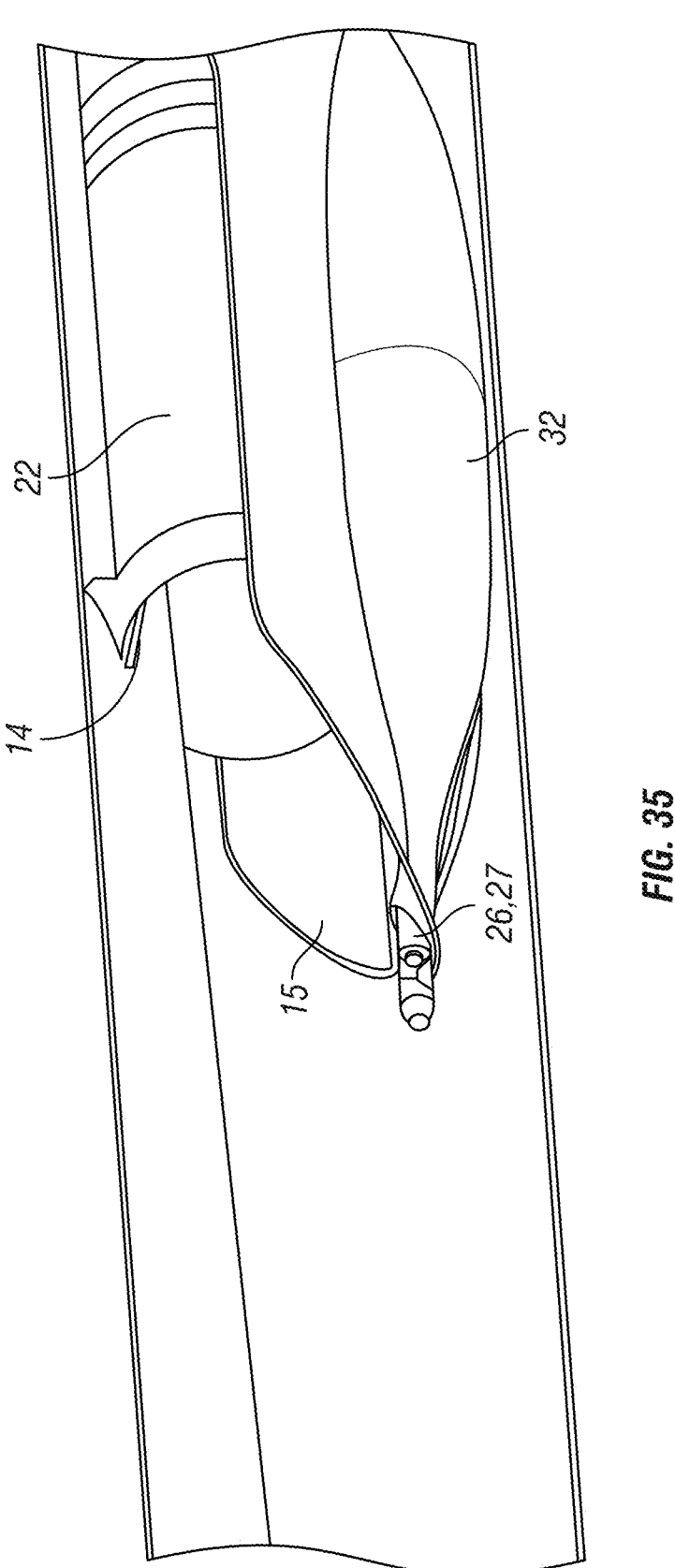
FIG. 35 is a perspective view of a device of FIG. 34 shown in a vascular space revealing one of the placements of an imaging element ahead of the element shown excising obstructive materials according to embodiments.

FIG. 35 is another perspective view of a working imaging, excisional, capture and transporting assembly 10 of FIG. 1, showing slight rotation of scoopula 15 supported by expandable element 32. In later illustrations, independent rotation of scoopula 15 from expandable supporting structure 32 will be shown such that automated disease material removal may be accomplished automatically and remotely, according to embodiments. Such automated disease material removal may include, according to embodiments, all needed motions such as expansion of element 32, control of rotation of scoopula 15, longitudinal positioning of and advancement of excisional elements 14 along with the same positioning choices for NRS 22 taking advantage of its thinner and thicker sections in contact with tissues creating a lesser or greater standoff between cutting blade(s) 14 and edges 11 and tissues being excised. This positioning of NRS 22 may also, according to embodiments, incorporate feedback and guidance from imaging elements such as ultrasound or OCT 27 (emanating from scoopula 15) to show overall and longitudinal extent of obstructive materials and ultrasound or OCT 27 (shown more distally in FIG. 35 and emanating from an additional, more inferior tandem lumen) for nearer-to-cutter, depth of removal guidance.

Figure 36:
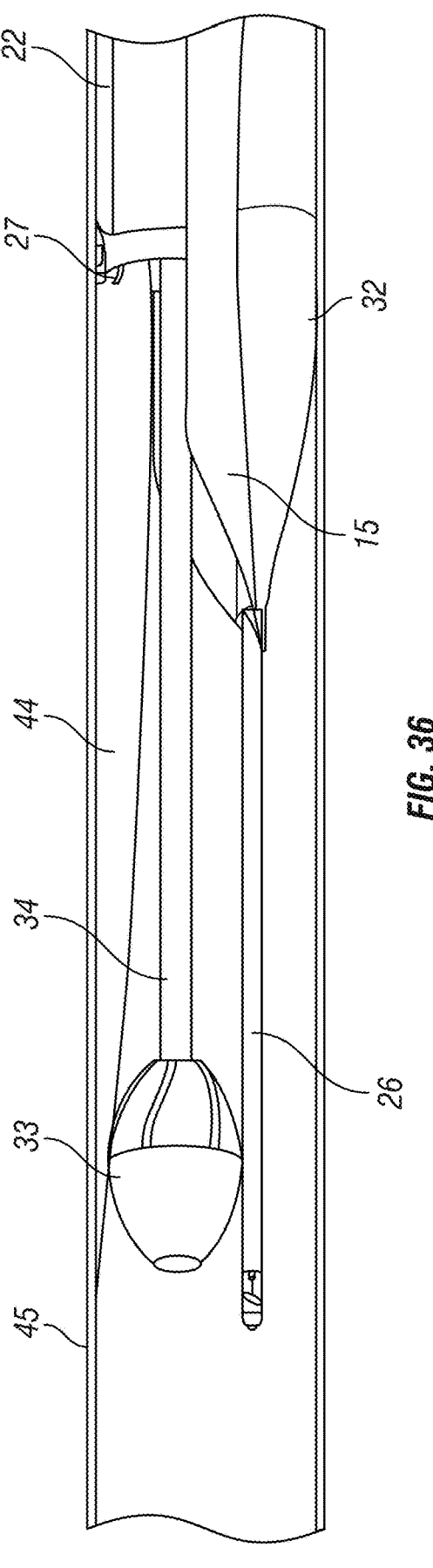
FIG. 36 is a perspective view of an excisional and imaging assembly shown in the process of excising obstructive materials from a vascular structure, with an expandable imaging parting off element extended to the distal edge of an asymmetric obstruction, as well as an additional imaging element extended out ahead of the expandable imaging parting off element according to embodiments.

FIG. 36 and subsequent figures re-introduce elements from previous illustrations, shown in several available positions within a diseased vessel 45. In this case, imaging modality ultrasound 26 with its longer range but lower resolution, is shown in a position in the bloodstream (blood does not block its imaging capabilities) to guide the longitudinal extent of disease material 44 while higher resolution OCT 27 (lower range but higher resolution) is positioned within imaging chamber 33 and up against a wall. In such a position, an OCT imager element can be in close proximity to both plaque (if this is the obstructing element) and excising elements shown farther back in this figure, and kept slightly ahead of NRS 22, such that OCT 27 may guide depth of excision in real time, in close coordination with the advancement of the cutting elements, for example. Given OCT 27's position inside transparent chamber 33, blood that is illustrated as still flowing due to the open channel provided in double balloon 32, does not interfere with the local OCT imaging through the blood-excluding transparent imaging chamber 33 and into the tissues to which imaging chamber 33 is in close proximity. Regulation of expansion pressure in element 32 both regulates flow and also by acting against supporting scoopula 15, regulates depth. Depth control may be a combination of several elements such as exposure levels of excisional elements controlled by NRS 22, to provide maximum precision of excision according to embodiments.

Figure 37:
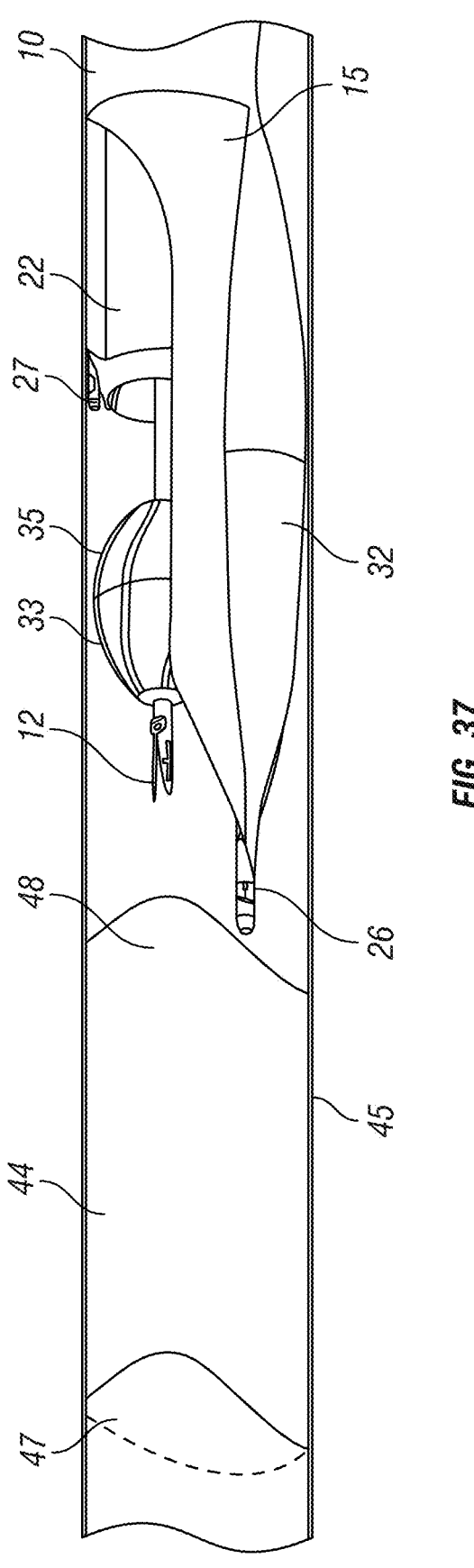
FIG. 37 is a perspective view of an excisional and imaging assembly of FIG. 32 shown approaching a totally occluded tubular structure such as a blood vessel, with one of the assembly's imaging elements poised at the near end of the total occlusion, while an inflatable supporting element is shown elevating the assembly to a point where a smaller additional excisional element is shown aimed at the nearest surface of the totally occluding material, as well as the larger excisional element slightly advanced within a scoopula portion of the assembly, while an expandable imaging, cutting and parting off element is shown supporting the smaller excisional element that is located at the forward edge of the expandable imaging, cutting and parting off element according to embodiments.

FIG. 37 provides an example of a totally occluded vessel 45 by mixed materials 44, which may include a hard, calcified proximal cap 48 and an often softer distal cap 47, as well as thrombus, plaque and calcium deposits in various areas throughout the obstructing material. This situation helps illustrate some of the capabilities of various elements of the present device 10 according to embodiments, such as the elevation positioning contribution of expandable pressure-applying element 32, directional and rotational positioning and stabilizing capabilities contributed by supporting scoopula 15, centering-capable, expandable, transparent imaging and cutting or ablating element 33 with its cutting blades 35 (which may function as a part off mechanism in conjunction with work element 13 beaks, as previously described for FIG. 21 above) on both its forward and aft surfaces and smaller excisional element 12 poised to engage a proximal cap 48 of, for instance, a chronic total occlusion lesion. When an imaging ultrasound element 26 is inserted there through, it may also supply lay of the land geographic and composition information while OCT imaging element 27 may subsequently replace an ultrasound imaging element 26 in this location and be utilized later in the intervention for final, depth-controlled clearing of any remaining disease material 44 that may still be present along a wall of vessel 45. Given the overlapping nature of OCT and IVUS (intravascular ultrasound), it becomes apparent that interchanging these modalities can be useful and also enabled by the capabilities of placing them in different locations by rotation of elements such as an NRS, by itself or in combination with expandable elements, can dial in the correct focal lengths of the various modalities, while deciding whether or not to occlude blood flow, with for example cuff 30, may also inform the decision as to which modality is best suited for a particular imaging task.

Figure 38:
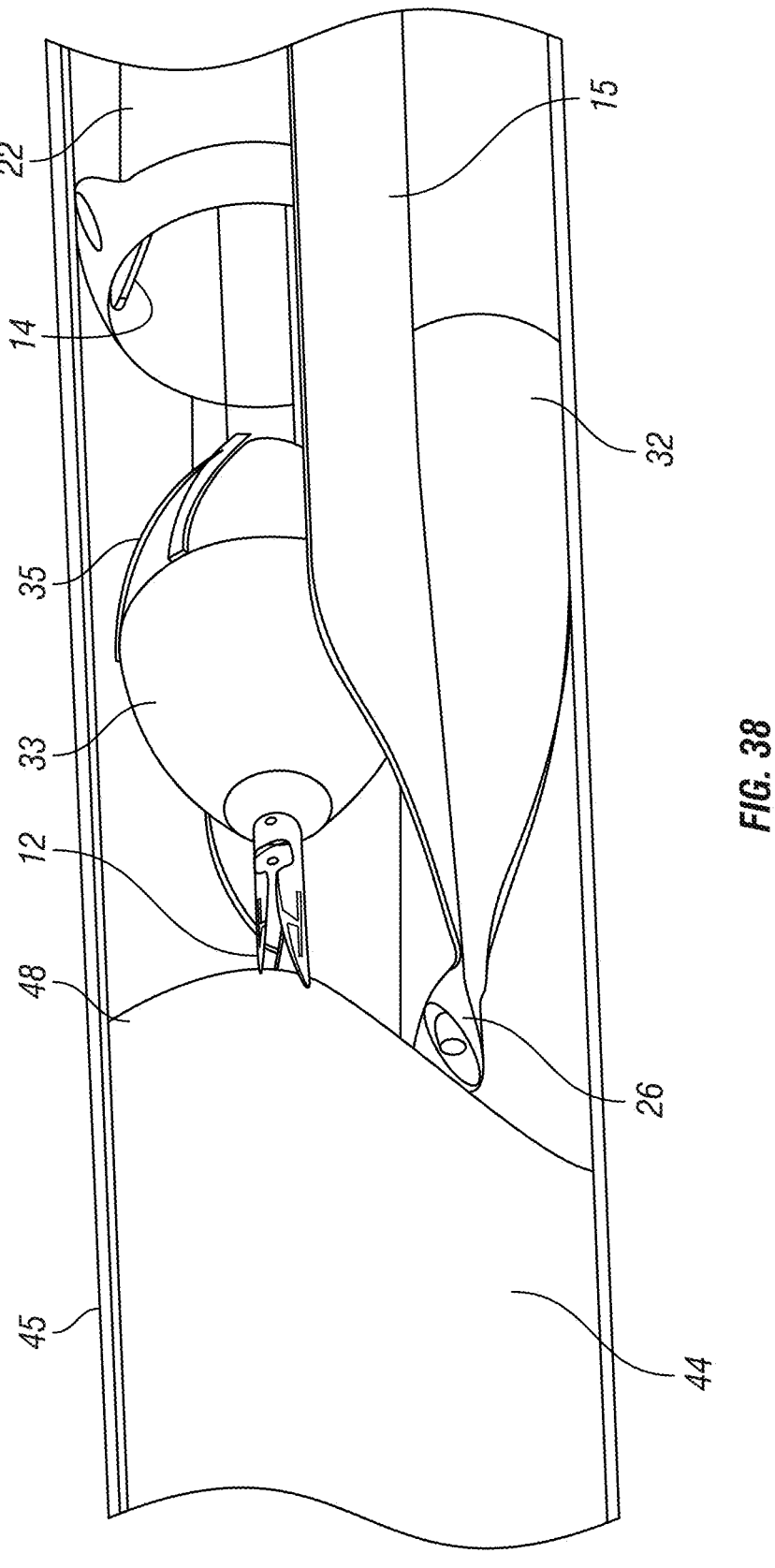
FIG. 38 is a closer up perspective view of an assembly described in FIG. 37, now shown with the smaller excisional element engaging the nearest portion of the totally obstructing material, in this case the expandable imaging parting off structure does not include the forward edge cutting blades, according to embodiments.

FIG. 38 provides a closer up view of the illustration described in FIG. 37, showing engagement by smaller excisional element 12 of the proximal cap 48 while scoopula 15 has been advanced up forward and elevated to provide, together with expandable imaging, supporting and centering chamber 33 and expanding supporting element 32, a maximally stable platform from which to operate excisional element 12 according to embodiments to selectively core through and part-off material from the proximal cap 48, the distal cap 47 and the intervening diseased obstructing material there between.

Figure 39:
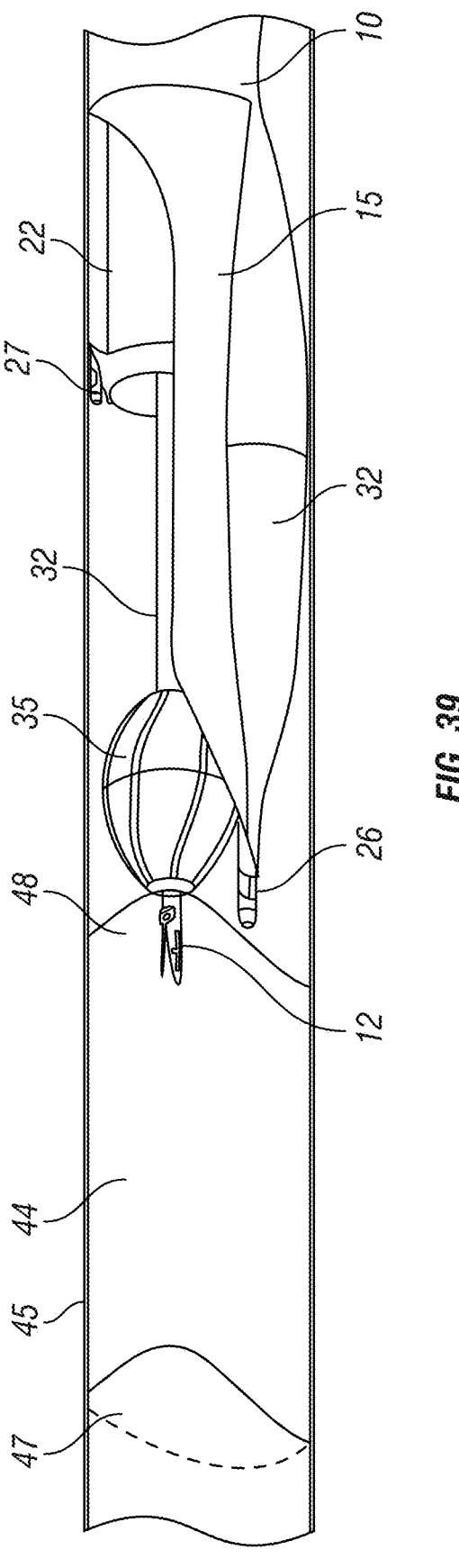
FIG. 39 is a perspective view of a tubular structure that is totally occluded as in FIGS. 37 and 38 with the exception that the expandable imaging, cutting and parting off structure now is shown with the included forward cutting blades according to embodiments.

FIG. 39 illustrates the capabilities of the elements of an imaging, excisional assembly 10 and the various components arranged to support and control the smaller excisional element 12 as it bores through the hard proximal cap 48 of the totally occluding obstructive disease material 44 along with imaging guidance and maximal support as described above along with precise placement at the very proximal most edge of the proximal cap 48, while an OCT imaging element may be introduced within smaller excisional element 12 once any tissue still in the lumen proximal to it, has been removed, according to embodiments. It is to be noted here that the OCT imaging element and/or other imaging of treatment devices may be introduced within and past the smaller excisional element 12 as such is constructed from a tube of material from which material has been removed to define the functional structures that enable the smaller excisional element 12 to selectively open and close. A consequence of forming the small excisional device 12 out of a hollow tube of material (as may be the work element 13) is that there are no structures protruding within the central lumen of the smaller excisional element 12 that are closer to the rotational axis thereof than the inside wall surface of the hypo tube from which the small excisional element was formed.

Figure 40:
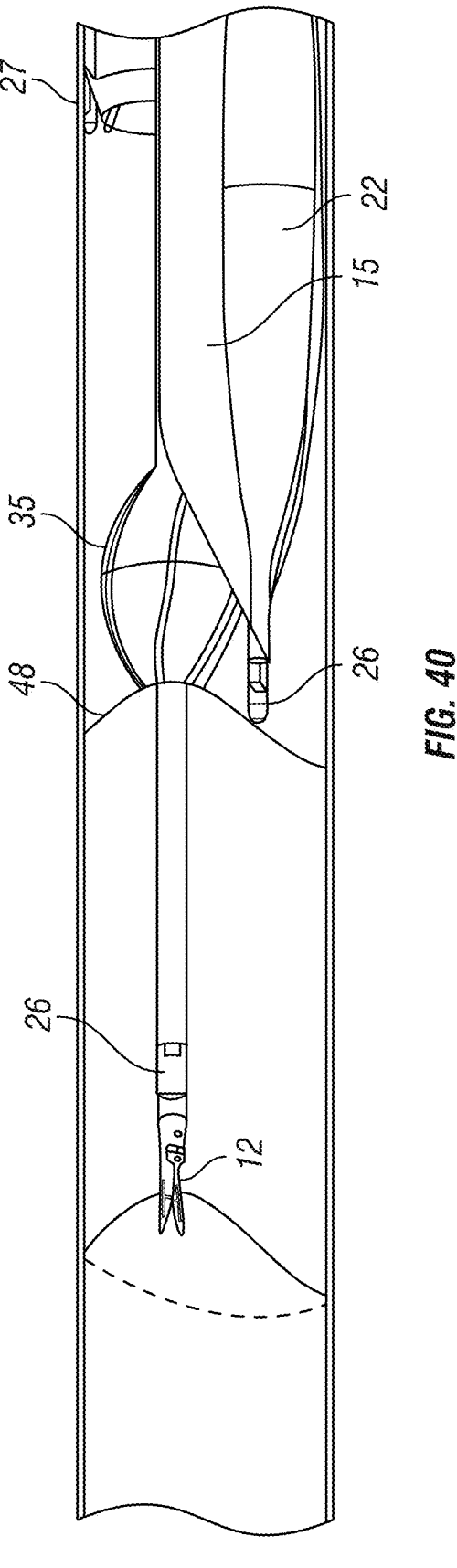
FIG. 40 is a perspective view of an excisional imaging assembly of FIG. 39 showing the smaller excisional element having cored all the way to the far end of the occluding obstruction as well as revealing an additional imaging element now advanced within the hollow tubular portion of the shaft of the smaller excisional element according to embodiments.

FIG. 40 illustrates further aspects of a device 10 in action, whereby after penetrating the proximal cap 48 and excising, parting off and transporting back obstructing materials, an imaging element such as OCT or other such guiding modality may be introduced within the central lumen of the smaller excisional element 12 to confirm proper placement and any extent of further penetration needed for complete progress through a total occlusion, particularly given that fluoroscopic guidance imaging may be of little use, due to the total occlusion nature of the vessel not permitting contrast agents to be injected beyond or even to the distal cap area (depending on collateral circulation availability). Even if collateral circulation were available, it may not reach the distal cap 48, in which case, guidance extension via the central open channel may be of desirable use, whether by OCT or ultrasound, or with microinjections of contrast through imaging element 33's (and also through the smaller excisional element 12's) central open lumen, as illustrated here and according to embodiments.

Figure 41:
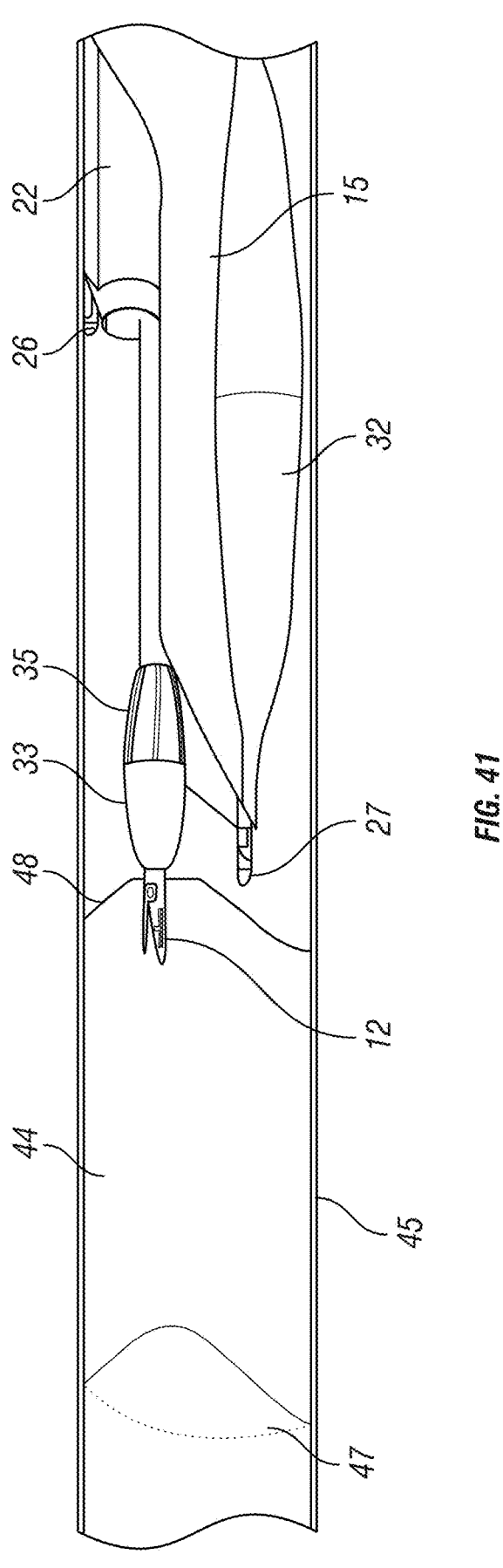
FIG. 41 is a perspective view of an excisional imaging assembly of FIG. 38 with the expandable imaging, parting off chamber in a mostly non-expanded state in a position just in front of an occluding obstruction according to embodiments.

FIG. 41 shows a potential next phase of an intervention in a case involving a complete occlusion of a vessel, whereby expandable, transparent, imaging chamber 33 is shown in a less expanded state to follow the smaller excisional element 12 more closely, as it penetrates deeper into and beyond a potentially hard proximal cap 48 of totally occlusive obstructing disease materials, after which advancement in the wake of smaller excisional element 12, expandable, transparent imaging chamber may be used for guidance as well as for further widening of a channel thus bored by the smaller excisional element 12, according to embodiments.

Figure 42:
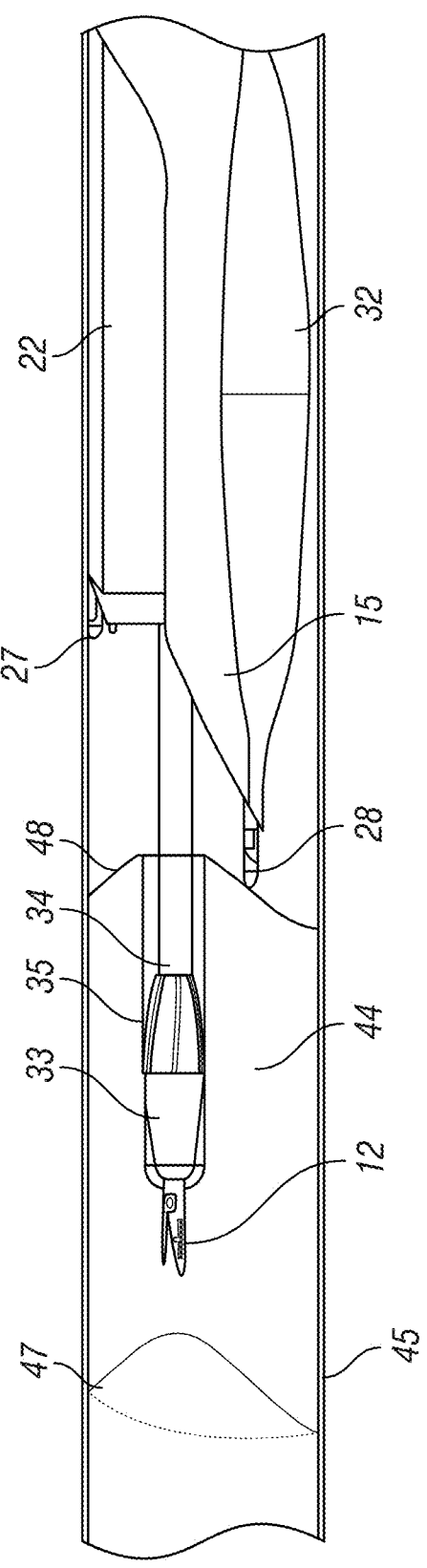
FIG. 42 is a side view of the excisional imaging assembly of FIG. 41 showing the expandable imaging, parting off chamber following the smaller excisional element partially through the occluding obstruction according to embodiments.

FIG. 42 shows that the progression described above as smaller excisional element 12 tunnels through obstructing material 44, it may be aided in its progress by backup support from partially expanded element 33, which element can also provide up close, even in-situ microscopic information about the nature of the occlusive materials along the way, according to embodiments.

Figure 43:
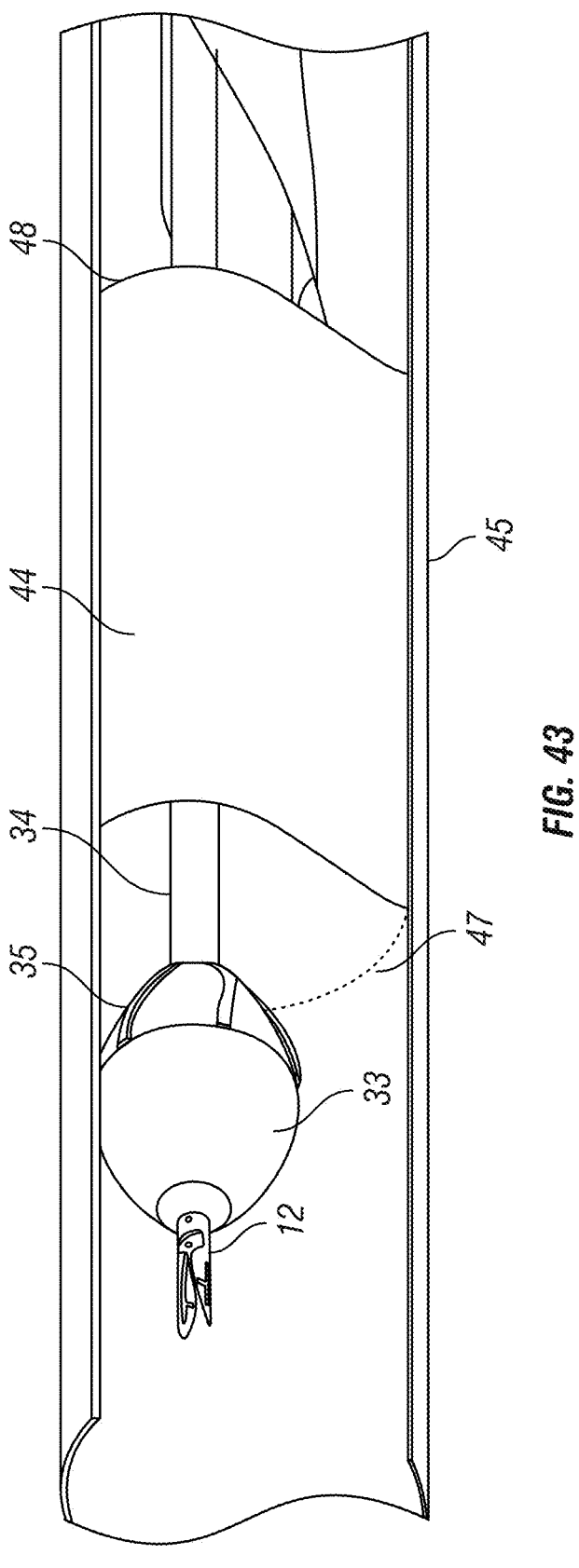
FIG. 43 is a perspective view of an imaging excisional assembly of FIG. 42 now showing the expandable imaging, parting off supporting chamber in expanded state at the far end of the occluding obstruction according to embodiments.

FIG. 43 shows still further progress as both smaller excisional element 12 and its supporting, trailing expandable, imaging, cutting and conjunctive parting off chamber 33 has also advanced beyond the distal cap 48 of totally occluding obstructive disease material, and which imaging, parting off chamber 33 is now poised for imaging and several additional options. The imaging chamber element 33 may serve as a rearward cutting instrument, using its cutting blades 35 on its rear surface and ultimately meeting up with an excisional assembly of device 10 with work element 13 located proximal to the proximal cap 48, or the imaging chamber 33 may remain in position to provide tow to help move a proximal excisional assembly forward, given its establishment in an anchoring position beyond the distal cap 47, or it may participate in a combination of the two movements. Another option is to leave a scoopula in position initially, and then as an NRS with its internal excising elements is advanced to excise and to meet up with imaging chamber 33 the material may be excised using this method. Another option is that a scoopula may also advance together with an NRS and including its excising cutters 14, through the remaining disease, excising and transporting materials back in the process while optionally using any of the choices for closely coordinated and closely approximated, precise imaging guidance all along the way according to embodiments.

Figure 44:
FIG. 44 is a perspective view of an excisional imaging assembly of FIG. 40 showing the expandable imaging, parting off, supporting and cutting chamber in expanded state at the far end of a previously totally occluding obstruction according to embodiments.

FIG. 44 illustrates just such a partial relief of a total occlusion with removal of some of the materials of disease material 44, 47 by one of the methods described above. Next steps may involve a combination of some of the described methods or may proceed with next steps as would be the case with a subtotal occlusion, including the use of any of the elements previously described including guidance, as well as others still to be described in the following illustrations and according to embodiments.

Figure 45:
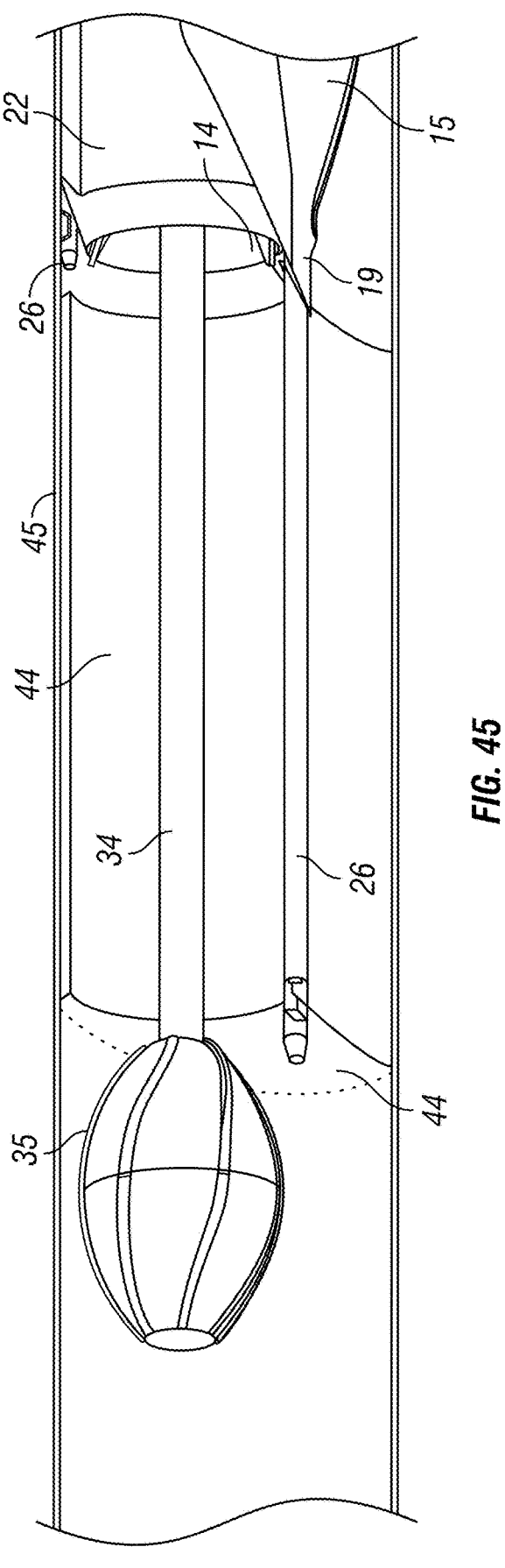
FIG. 45 is a perspective view of an excisional imaging assembly of FIG. 44 in a previously occluded tubular structure, with the expandable imaging, parting off, supporting and cutting chamber, in this case without the smaller excisional element and with an imaging element extended out from a tubular channel in the scoopula, to the far end of the obstructing material according to embodiments.

FIG. 45 illustrates some of the placement options for guidance modalities once the chronic or acute total occlusion has been converted into a subtotal obstruction, here showing in this example, the advancement of an OCT 26 element, which before downstream blood flow is fully restored, or allowed to proceed, may be simpler to use while less affected by blood interference, according to methods and embodiments.

Figure 46:
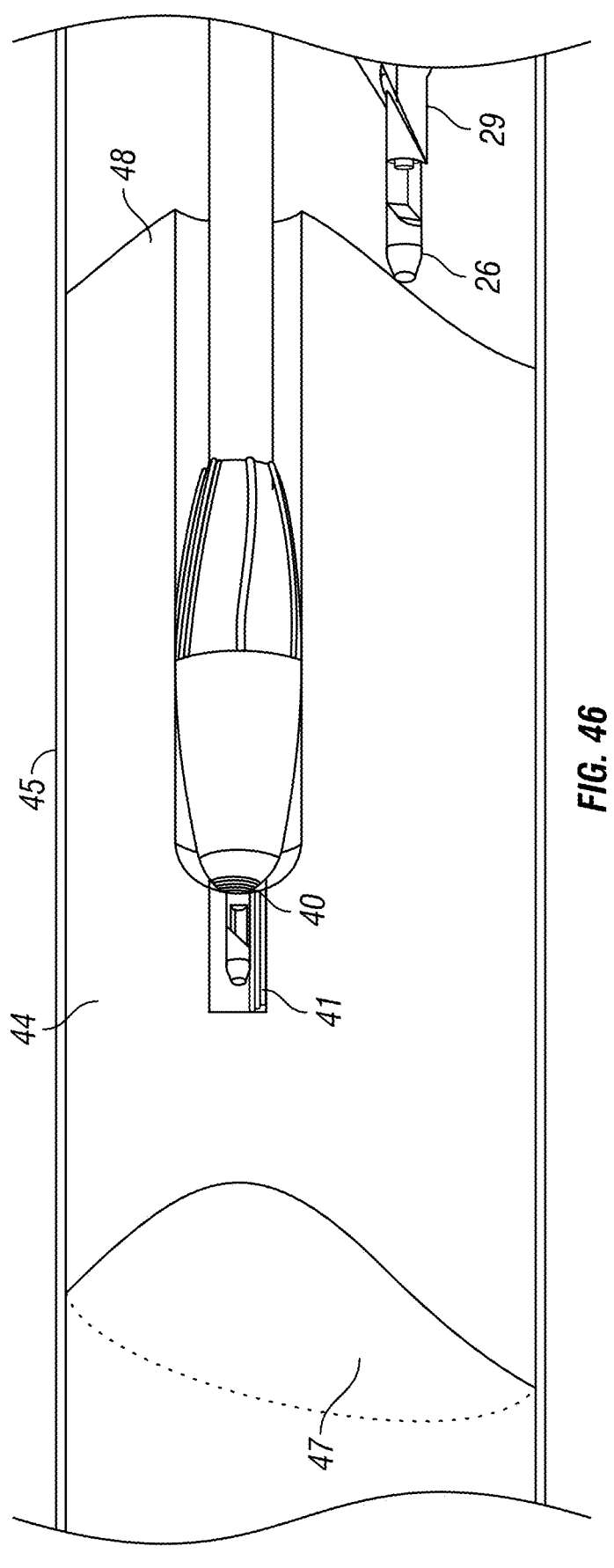
FIG. 46 is a close up perspective view of a smaller, in this case energized excisional element shown in partial cutaway view, to reveal an integrated imaging element in its central lumen followed closely by an expandable supporting chamber of FIG. 42 all within a totally occluding obstruction that exists within a tubular structure such as a blood vessel, as well as revealing a small portion of a supporting scoopula of a device of FIG. 40 and an additional imaging element protruding within there from according to embodiments.

FIG. 46 illustrates in a partial cutaway view, another excisional and ablative element 40, in this case a coaxially located laser energy beam delivery element 40 with multiple laser energy delivery fiber optic tip elements indicated as 41, and also in this case, a coaxially located imaging element, supported by the various elements already described in detail above, including in this illustration, an imaging chamber in partial expansion as in prior examples and according to embodiments.

Figure 47:
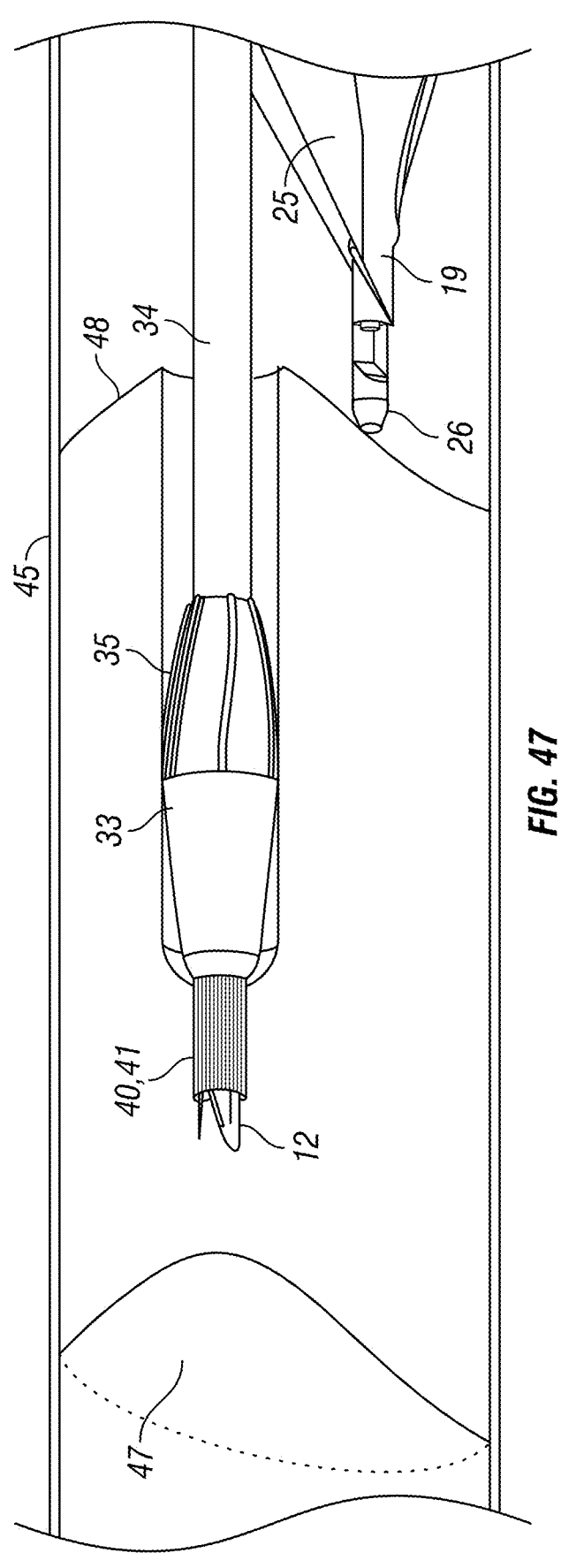
FIG. 47 is a side view of an imaging excisional assembly of FIG. 46 with in this case its smaller, energized excisional element shown in non-cutaway view, along with an additional smaller excisional element of FIG. 44 coaxially located with the energized excisional element and again closely followed by a supporting, expandable, imaging, parting off element shown in partially expanded state according to embodiments.

FIG. 47 introduces the concept of augmented, combined excisional and ablative elements 12, 40, 41 coaxially located relative to each other and extending through an expandable, transparent imaging and cutting chamber element 33 according to embodiments. However it should be noted that, while represented by a laser element in this case, any number of energy sources may be substituted and considered within the scope of the present invention, including high energy, focused ultrasound, inert gas augmented or simple monopolar or bipolar radiofrequency or other shock wave producing modalities, hydro-dissection modalities or any other source of energy transmission that may utilize these methods and devices for placement, access, guidance, support and control according to embodiments. It should also be noted that while illustrated in this figure with laser element 40 with its multiple tip elements 41 wrapped coaxially around work element 12, that laser element 40 may also be coaxially located relative to work element 12 inside the central lumen of work element 12.

Figure 48:
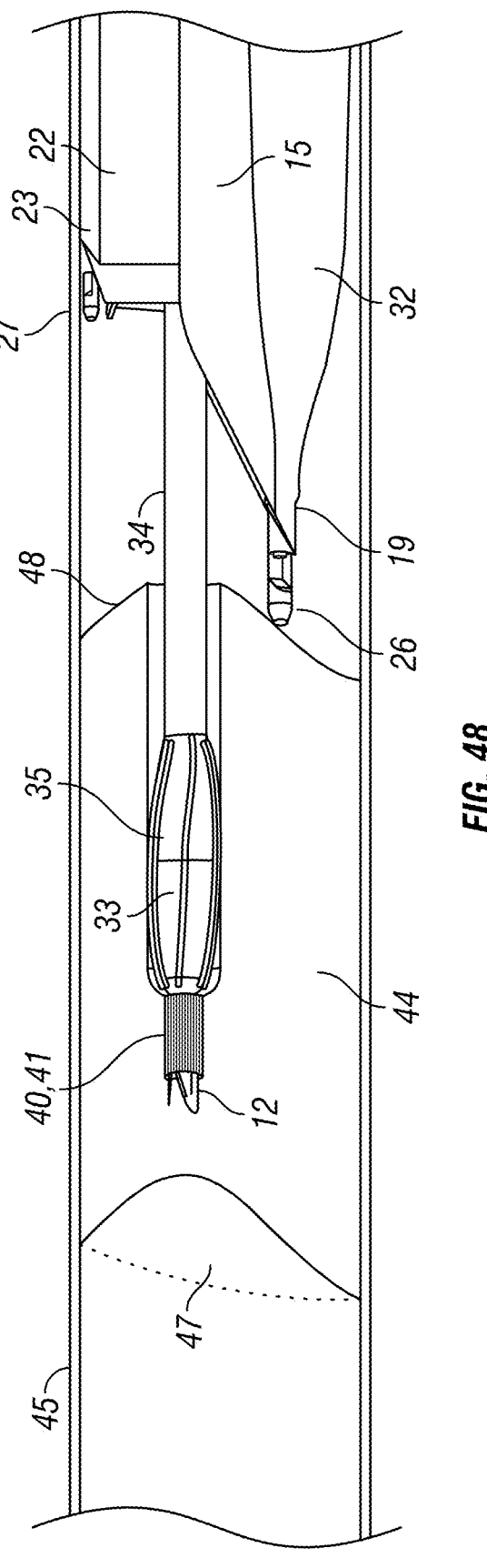
FIG. 48 is a side view of an imaging excisional assembly of FIG. 47 with its smaller energized excisional element and additional coaxial excisional element of FIG. 44, closely followed in this case with the alternative version of an expandable imaging, parting off, supporting and cutting element shown more than half way through a totally occluding obstruction that exists within a tubular structure, such as a blood vessel, all of which working elements are supported in an elevated position by a scoopula and its expandable element attached to its inferior portion, and also visible are two imaging elements each in one of several locations provided according to embodiments. Furthermore, the shape of the imaging chamber, though shown with curved sides in various states of expansion, may equally be shown to have sides, which are constructed to expand in a parallel manner according to embodiments.

FIG. 48 adds further to the disclosure of combined excisional modalities including rotational cutting augmenting channel widening following the pilot bore established by other modalities, using chamber 33 with its cutting blades 35 on both forward and rear areas. Indeed, as shown, the smaller excisional device 12 and its ablative elements 40, 41 may create the pilot bore ahead of the imaging and cutting chamber 33 which, by virtue of its girth and blades fore and aft, cuts through material in its path, following the pilot bore, thereby widening the channel through which it advances through the diseased material. During rotation under the power transmission via shaft 34, for example, a wider channel may be progressively produced with expansion and cutting of the elements of chamber 33 in preparation for complete removal of remaining materials using other elements of an excisional imaging assembly according to embodiments.

Figure 49:
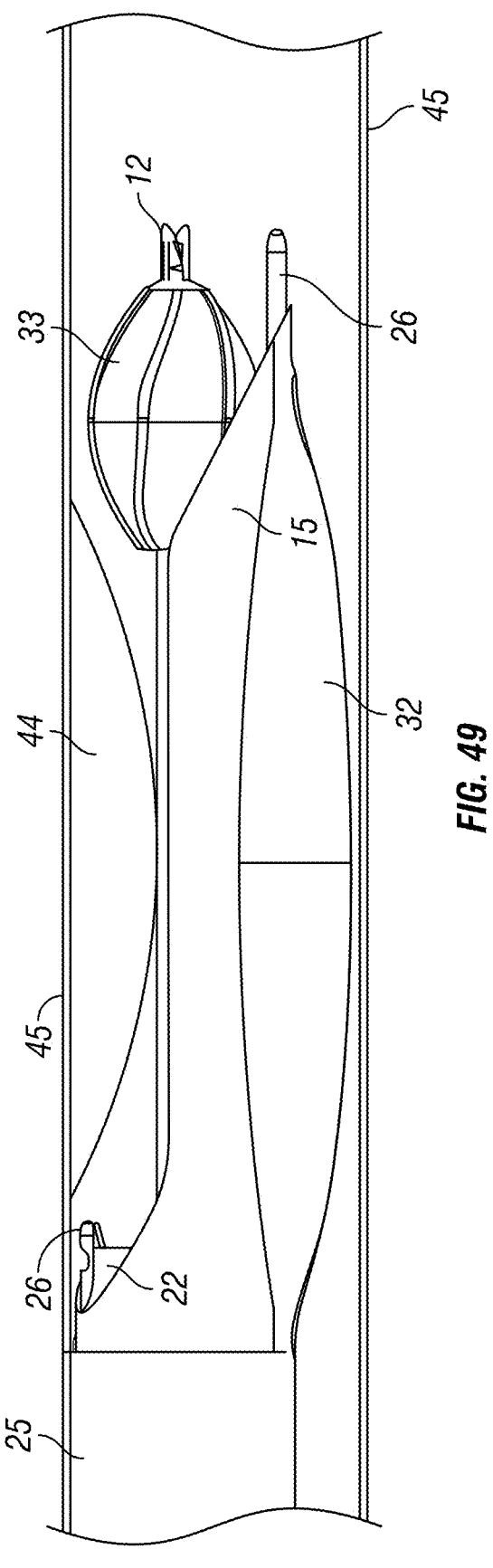
FIG. 49 is a side view of an excisional imaging assembly in this case with various elements of the assembly straddling an obstructive lesion within a tubular structure such as a blood vessel with a larger excisional element and an imaging element near the cutting surfaces on the near side of the obstruction and an imaging, parting off cutting chamber on the far side along with an additional imaging element emerging from a supporting scoopula with its underside expandable elevating element, which is shown supporting elements of the assembly according to embodiments.

FIG. 49 illustrates advantages of a stepwise utilization method of various elements described and illustrated herein, showing a previously total occlusion, now converted into a subtotal lesion 44 of a vessel 45, being addressed with guidance elements such as OCT element 26, shown here below the imaging chamber element 33, along with a combination of depth control using expandable support balloon element 32 to center and/or position imaging chamber 33, with an additional optional guidance element, similar to or equal to OCT element 26, shown in location adjacent to excisional blades of work element 13, and with its imaging tip shown just ahead of the distal end of the non-rotating sheath element 22 according to embodiments.

Figure 50:
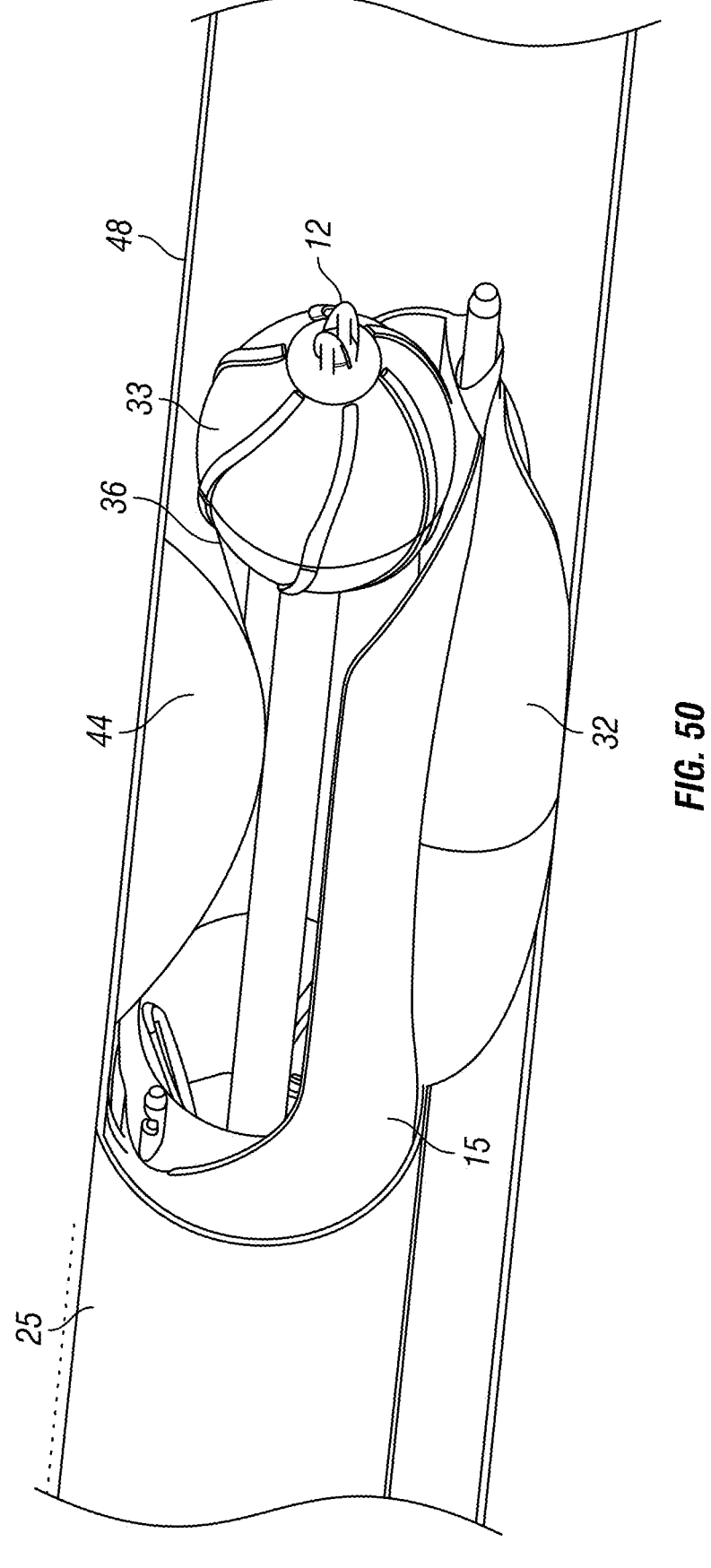
FIG. 50 is a side view of an expandable, transparent, imaging, projecting, focusing and directing chamber showing additional tethering elements attached thereto, with an interventional channel internal to the expandable, transparent, imaging, projecting, focusing and directing chamber and a tandem imaging channel invaginated into or internal to, the expandable transparent chamber in a straight position within an excisional assembly and according to embodiments.

FIG. 50 illustrates another configuration of an expandable, transparent imaging and in this embodiment, angleable, captured chamber 33 with its additional restraining tether(s) 36 (see FIG. 51) showing imaging and cutting chamber 33 in straight line position and over and under tandem lumens of scoopula element 15 to enable imaging elements such as OCT 26 (shown in an invaginated lumen within chamber 33 in the following FIG. 51) to continuously monitor and guide progress without the need to clear tissue from the lumen of an excisional device such as smaller excisional work element 12, again seen here ready to engage and bore through a proximal cap 48 of a totally occluding obstructing disease material 44 in a vessel 45. Also, any element, such as that shown as OCT catheter 26 in the following FIG. 51, can exert forward pressure on chamber 33 to augment bending of such a chamber in a direction opposite to placement of a tandem-placed lumen of scoopula 15 as shown and according to embodiments.

Figure 51:
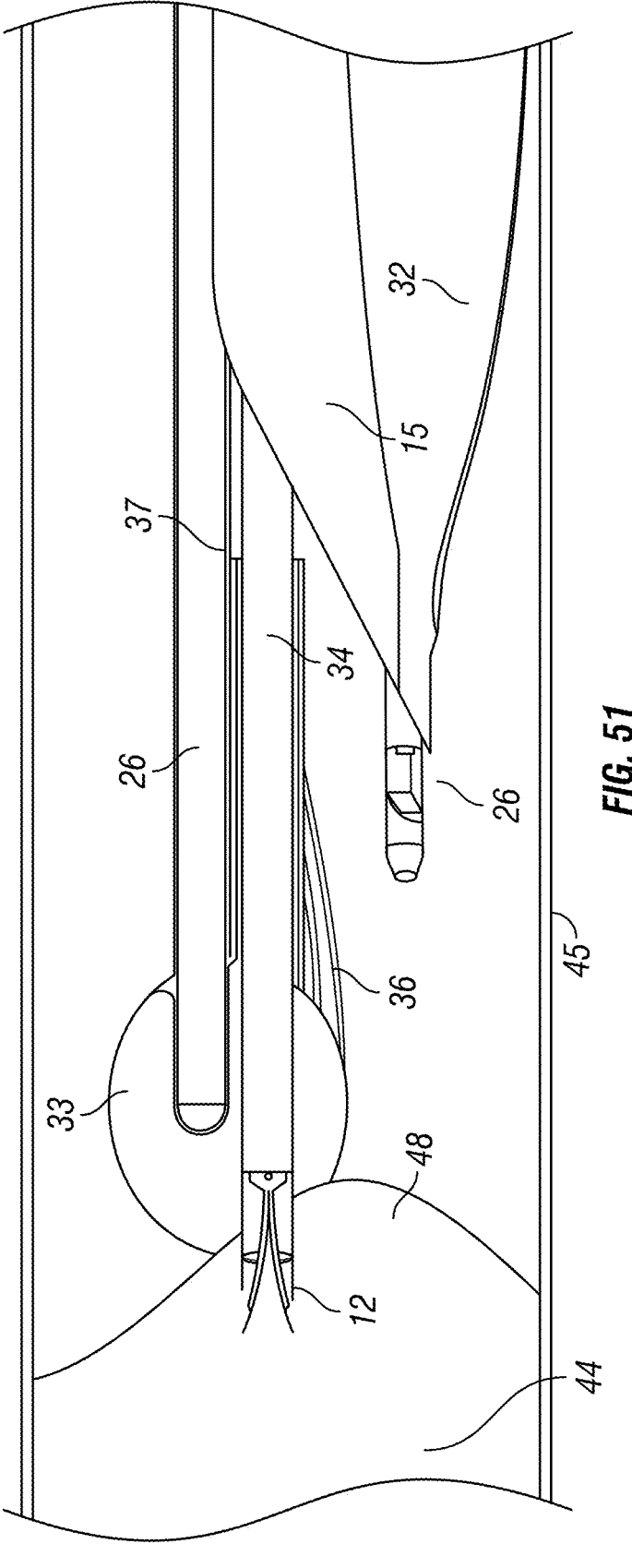
FIG. 51 is a side view of the assembly shown in FIG. 50, in this case in an angled position according to embodiments.

FIG. 51 shows the assembly as in FIG. 50. In this illustration, however, the angling and simultaneous imaging, guidance and boring capabilities are shown in FIG. 50 and as before, utilizing any of the additional ports, such as the dual incorporated over/under lumens of scoopula element 15, for guidance is shown with an additional, optional imaging (such as OCT) element 26 located in a lumen channel of scoopula 15, which element is stably supported by expandable support element 32. In this illustration, elevation and stability as well as guidance is provided to imaging chamber 33 as well as its incorporated imaging element 26 and significantly, stability for the angle of attack provided by tandem, tethered imaging chamber 33, such that smaller excisional element 12 is properly elevated and directed for optimum penetration. Expandable element 33 may be selectively angled as desired. One such method for doing so is simple inflation given the differential placement of tandem lumens where a central directable lumen is affixed to a forward and rear wall of captured (within the scoopula 15 bed) imaging chamber 33, while lumen for imaging element 26 is only affixed to the rear wall. Thus, advancement of imaging element 26 while holding back central lumen 34 would cause angulation of lumen 34 as shown. An additional angling method comprises differentially expanding upper and lower portions of cutting and imaging chamber 33. Yet another method may include advancing the inner lumen relative to the outer wall would, due to the asymmetry of forward restraint provided by tether(s) 36 would result in angulation in the direction of restraint, in this case shown as downwards, which in combination with a highly torque-capable shaft 34/37 would result in angle and rotation control of cutting and imaging chamber 33, in turn and which, in combination with elevation and platform stability provided by scoopula 15, which may itself be articulable, and its supporting expandable elements 32 as guided by imaging elements, provides precise control of excisional direction, position, support and progress, according to embodiments. Likewise, placing interventional elements in an upper space and, for example, an OCT imaging element in the flexing lumen 34, OCT imaging direction could be aimed forwards, backwards or at any combination of angles for more options without needing to change the basic configuration of an OCT element, according to embodiments.

Figure 52:
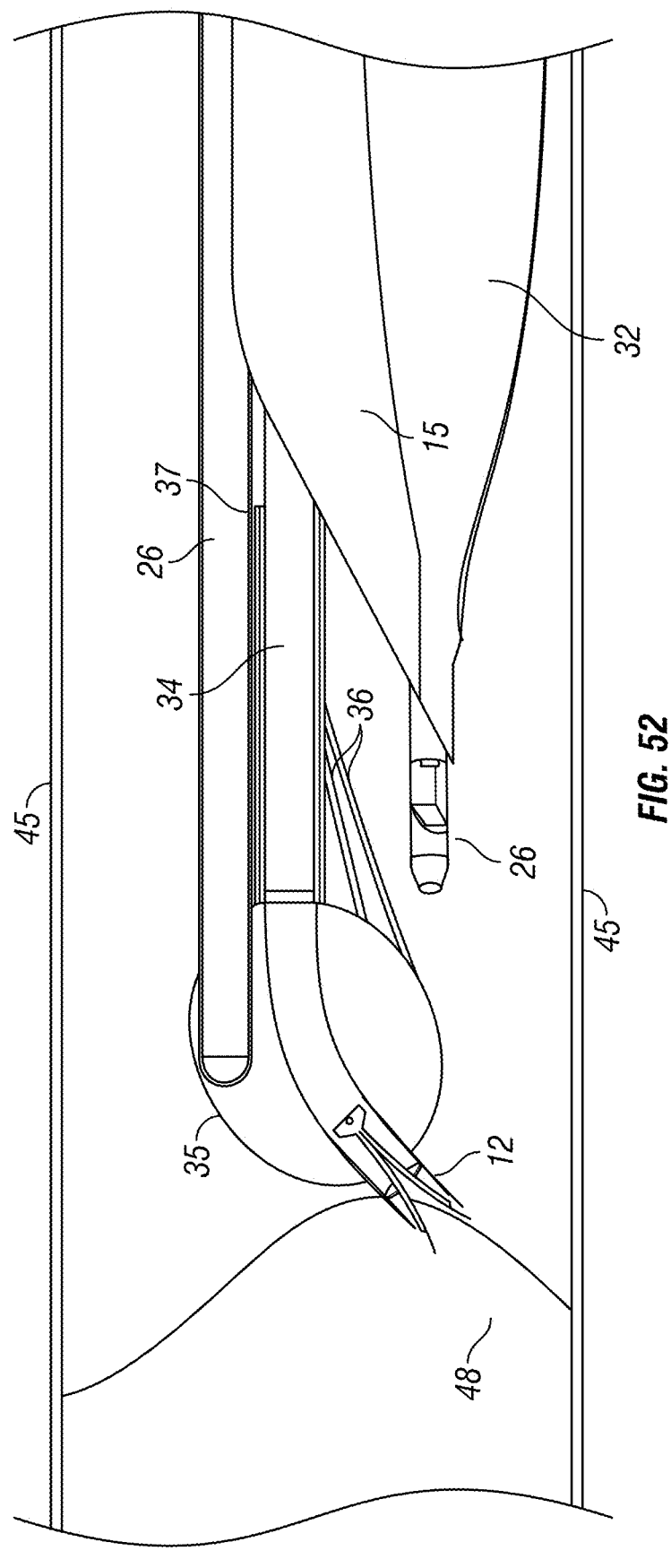
FIG. 52 is another side view of the assembly shown in FIG. 51 in angled position with a different excisional element according to embodiments

FIG. 52 illustrates the utility of the angle-capable imaging chamber 33 of FIGS. 50 and 51, where an energy-based, touchless excisional element may be introduced in the angled segment of imaging chamber 33, using the same capabilities as described in FIG. 51, to direct energy in the proper direction and at the desired intensity. In order to properly place imaging chamber 33, again, the mechanisms of excisional imaging device of FIG. 51 may be utilized for elevation and stabilization control.

Figure 53:
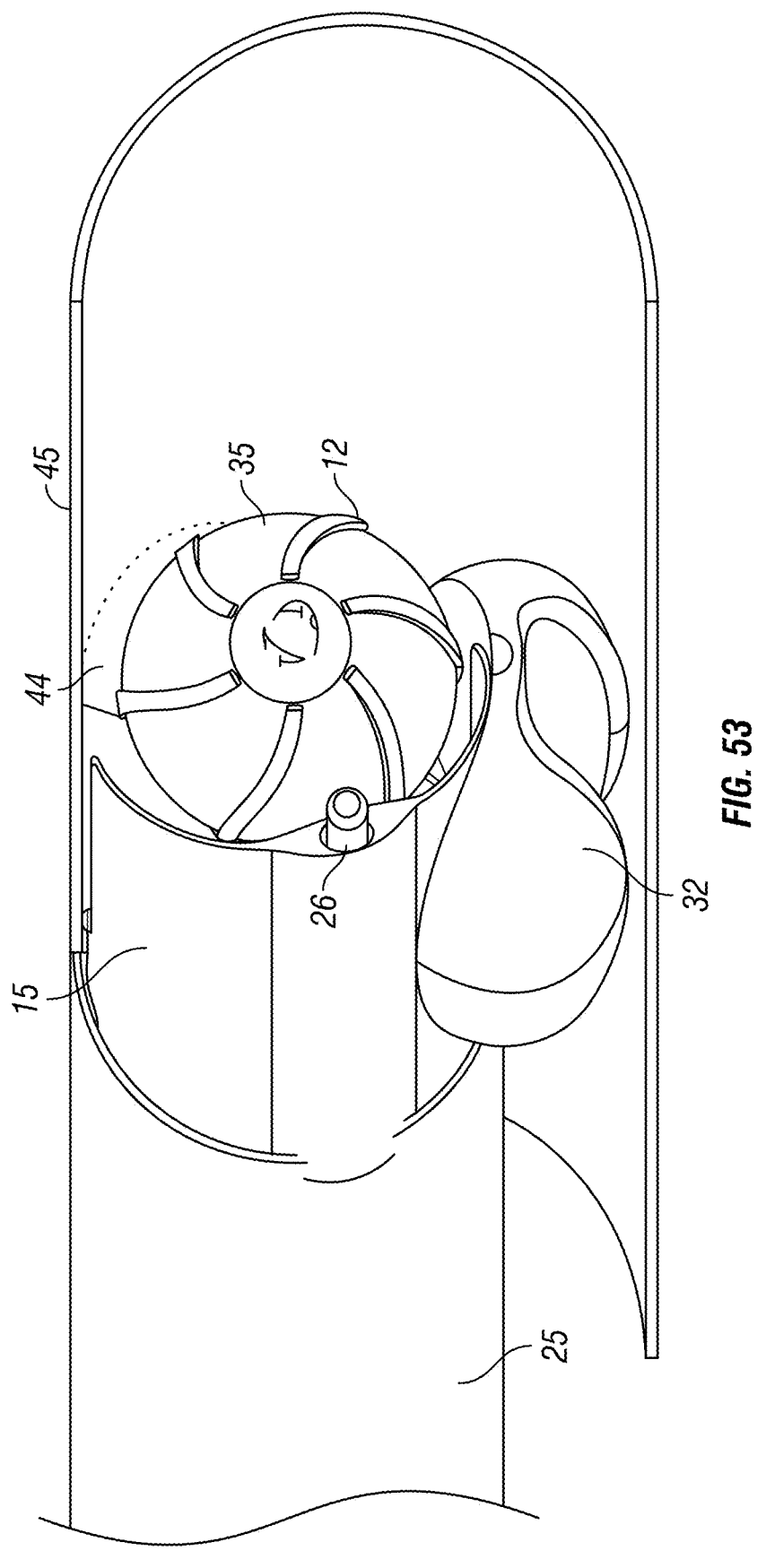
FIG. 53 is a perspective view of an excisional imaging assembly of FIG. 50 in a tubular structure that has a partially occluding obstruction, in this case showing independent, in this case clockwise, rotation of a scoopula component and an expandable supporting element on its underside, shown here as a flow providing double element as illustrated in FIG. 34, which reveals a flow channel space between the double expandable support element according to embodiments.

FIG. 53 shows a device of previous figures where scoopula 15 is rotatable independently of supporting element 32, which such a device may also have beak elements 14 replaced by other excisional or ablative modalities such as excisional laser energy emitters for example. Such an element is shown here with an excisional laser, which may be optionally guided sequentially or simultaneously with other imaging elements disclosed herein. Imaging and energized excision and ablation may likewise be accomplished in rapid sequence over shared light guide tubes or shafts or may be accomplished with coaxial rows ("coliseum seating") of dedicated light guide tubes, or columns among rows, as well as alternating guides within rows or columns according to embodiments, and these may be utilized to provide real-time feedback control and guidance. Similarly, one of the lumens of tandem, expandable, flexing-capable imaging chamber may be equipped with an inner surface that may be used to guide light pulses in the event that an imaging and excisional light source catheter may be too stiff to itself accommodate to a curve desired and achievable by such a lumen within imaging chamber 33, according to embodiments. In this manner, extremely short-wavelength electromagnetic energies may be utilized to limit the depth of excision and ablation, modulating distances and intensity of penetration by positioning within an expandable, flexible, shape changing imaging chamber 33, which may be thought of as a focusing, "shading" device, in addition to its role in providing directionality and positioning, according to embodiments.

Figure 54:
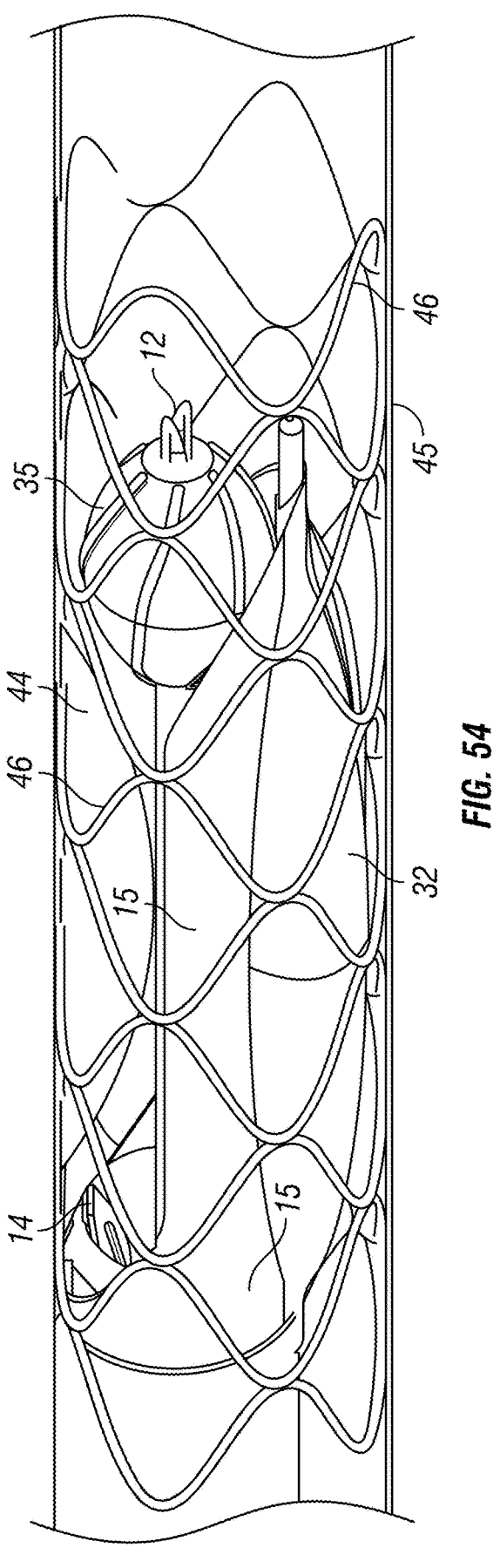
FIG. 54 is a perspective view of an excisional imaging device shown inside a stent that has obstructive material partially occluding a vessel such as a vascular structure, and as in FIG. 53 again showing independent rotation of a scoopula and its expandable flow channel providing supporting element on its underside according to embodiments.

FIG. 54 shows an application of the methods and devices described and shown herein, in the context of restenosis within an implantable device such as a stent 46. When intimal hyperplasia ("scar") occurs in response to a stented segment of a vessel, it is often difficult and potentially tedious to effectively and optimally remove all tissue while minimizing damage to stent struts. However, automated, robotically controlled complete de-bulking with excisional assemblies as shown and described herein could be carried out without the need for excess fluoroscopic guidance, thereby minimizing the health concerns for operators and patients alike. Once strut locations are established by imaging, particularly utilizing expandable, imaging, depth controlling imaging chamber 33, precise and stable positioning can proceed followed by the rapid succession of steps including longitudinal location, initial rotation, supporting elevation and pressure, flushing and aspiration, excision, parting off and transport, excisional element retraction. These steps may be repeated as needed under imaging feedback until all traces of obstruction to flow are removed and full lumen cross section is once again made available for optimal flow, according to embodiments.

Figure 55:
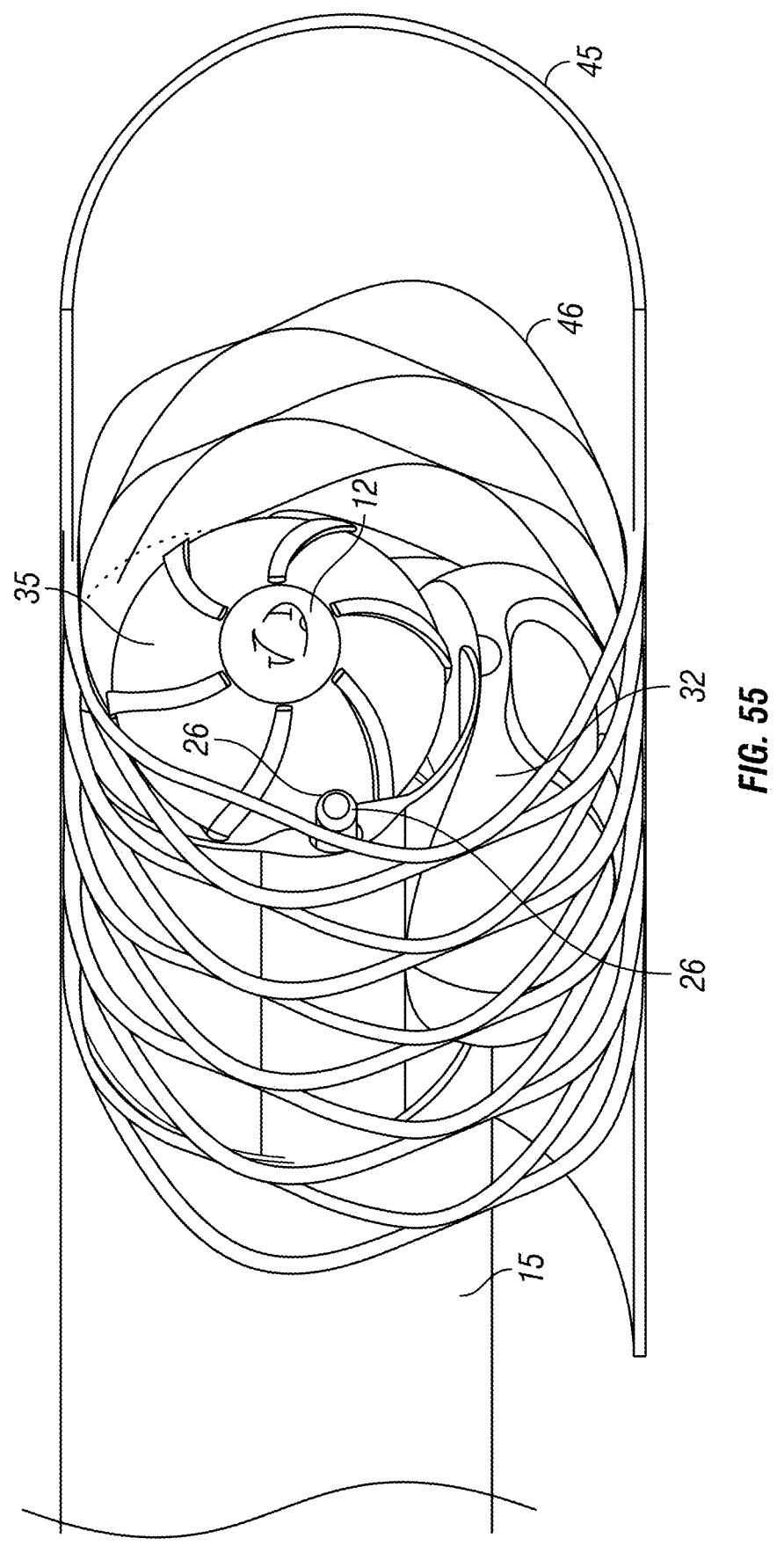
FIG. 55 is a more head-on perspective view of an excisional imaging device of FIG. 56 showing slightly more clockwise, in this case, rotation of a scoopula with respect to its inferiorly placed expandable supporting, flow providing and stabilizing element within a stented segment, again partially filled with obstructive material, of a vascular structure, also again showing an expandable imaging, parting off, cutting chamber with a smaller excisional element located at the imaging chamber's forward end according to embodiments.

FIG. 55 further illustrates the use of longitudinal and rotational positioning, stability and support, guidance and depth control provided by the various elements described and shown herein. In FIG. 55, stability and flow enabling and control provided by expandable element 32 are enhanced by the expandable element 32 being able to remain in place-both axially and rotationally-due to its attachment, including expansion controls, to the outer tube element 25 rather than to the scoopula 15. This attachment and control arrangement enables expandable element 32 to provide a stable platform upon which scoopula 15 may be moved in rotation and axial position, which may be particularly useful during automatic cycling steps. In this manner, certain steps may remain unchanged for several cycles while others can occur quickly and efficiently according to robotic manipulations driven by algorithms, which themselves can be modulated automatically with imaging and physiologic feedback according to embodiments. Manual override may be made available for safety, but automated steps may limit procedure times, radiation exposure and ischemia in the case of this intervention occurring in a vascular structure. Another limiting factor is often simply fatigue among operators and patients alike, which can be reduced with efficiencies provided by automation. A sequence could then be longitudinal placement followed by expansion with flow control and support by expandable element 32, followed by a series of rotational positioning(s) of scoopula 15 with automatic excision steps carried out at each rotational position until either all obstructing materials are cleared. In some instances, depending on the distribution radially of obstructive materials, a relocation of supporting expandable element 32 may be necessary, but generally not as frequently as would be the case were scoopula 15 not independently movable with respect to element 32. Independent relative movements combined with imaging from the surface (such as fluoroscopic), imaging in-situ via ports as illustrated herein, and physiologic parameters feedback (comparative proximal and distal pressures and flows, as measured via the various lumens available as illustrated and described), can all be utilized to maximize patient safety while enabling a maximally efficient procedure, according to embodiments.

Figure 56:
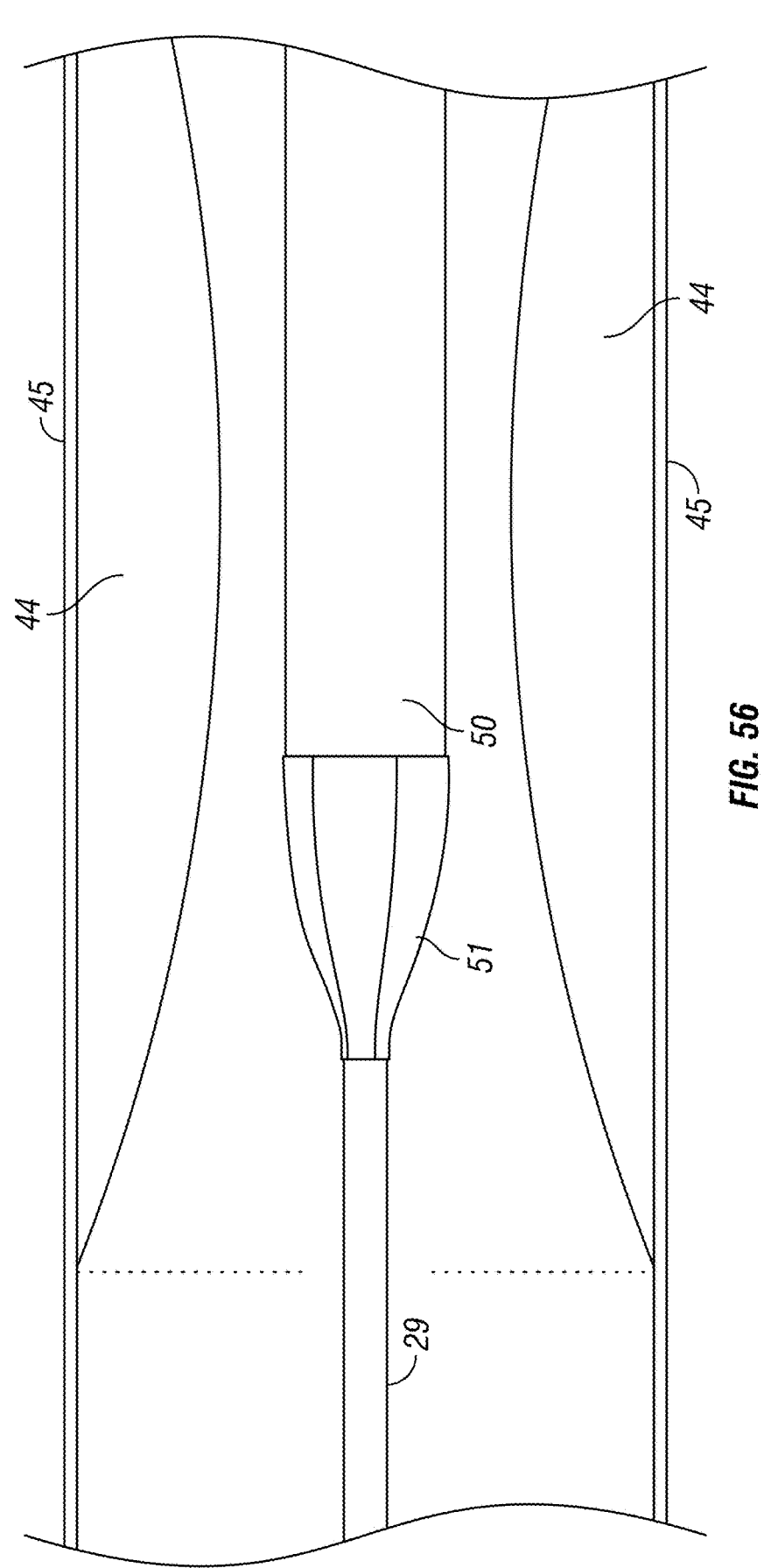
FIG. 56 is a side view of a protection element shown for clarity in isolation and in a streamlined closed configuration, within a partially obstructed tubular vessel such as a vascular structure, according to embodiments.

FIG. 56 introduces another device that may be used in combination with the imaging, excision and ablative elements described herein intended to isolate an area being treated that may (as is common in several clinical presentations including diseased segments that may be chronic, subtotally obstructing disease complicated with acute thromboembolic materials that may worsen or completely obstruct flow) contain a mixture of old and new materials of varying composition. In addition to isolating an area, the elements in this and following descriptions and illustrations may also be used to direct flows of various media emanating from other elements that form an assembly for the purpose of removing debris and loose materials, in particular those that may cause the presentation of paroxysmal symptoms related to intermittent obstruction. In this case, an assembly comprising cannula 50 and flush, aspiration and protection element 51 is shown inside a symmetrically obstructed vessel 45 by obstructing materials 44, which in this instance may be soft plaque or thrombus or a combination thereof. The assembly comprising cannula 50 and flush, aspiration and protection cover 51, which may be constructed of a mesh, fabric, or thin flexible membrane material, for example, is shown having been advanced into position over a guiding wire 29, while in a streamlined, non-expanded configuration according to embodiments. The following figures will illustrate the use of cannula element 50 and cover element 51.

Figure 57:
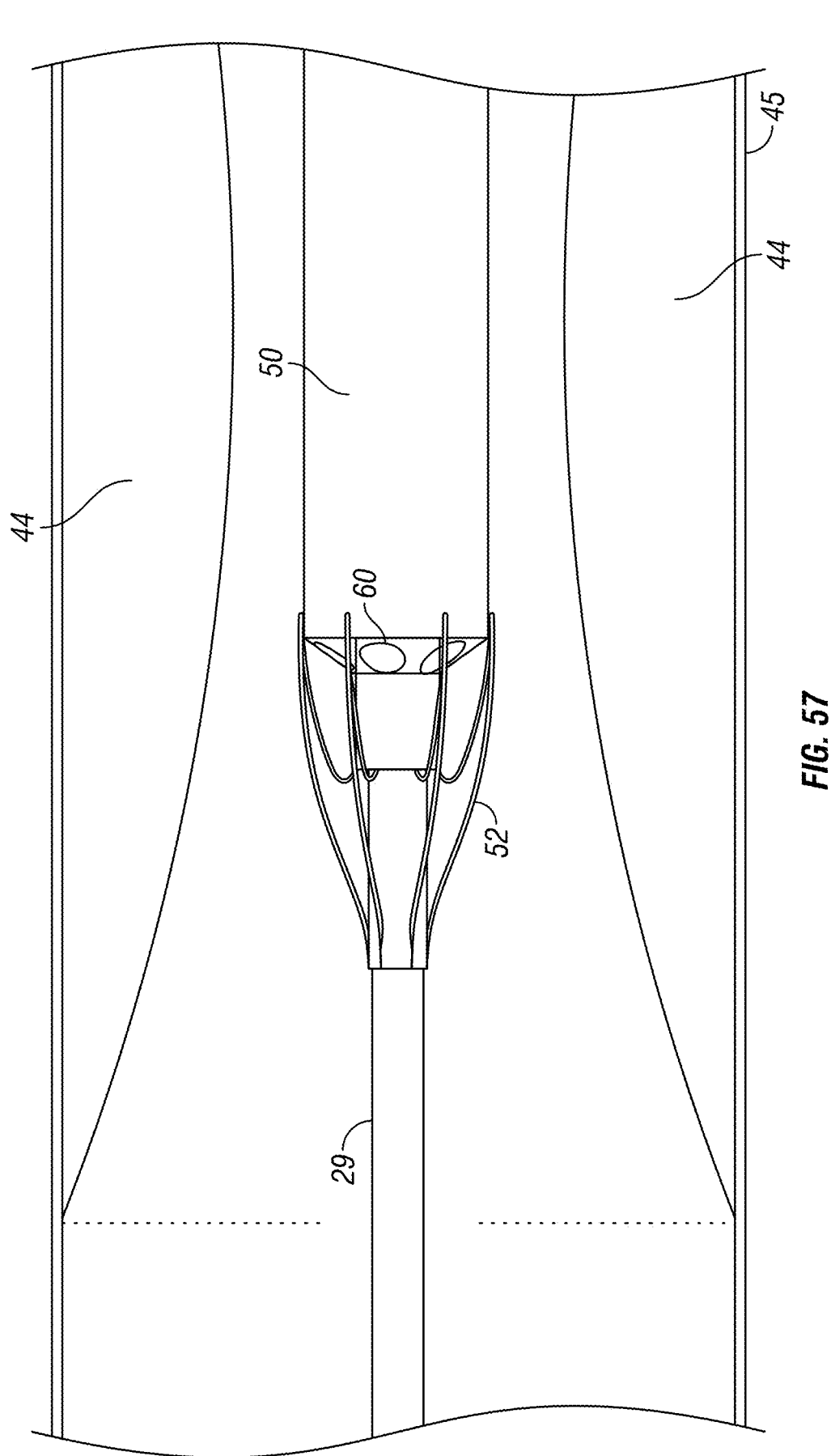
FIG. 57 is a side view of a device of FIG. 56 where an outer covering is transparent, revealing inner supporting and actuating elements in streamlined, collapsed configuration according to embodiments.

FIG. 57 shows a transparent outer covering, revealing additional deployment control elements (e.g., struts) 52 and orifices 60 of cannula element 50 and cover 51 (material between the control elements (e.g., struts 52)), again within a diseased vessel 45. Illustrated here are elements for controlling both placement of cover element 51 and tube with expandable struts elements 52 relative to orifices 60 of cannula 50 as well as degree of opening of flush, aspiration and protection cover element 51. An inner extension of cannula 50 is shown coaxial and surrounding a tubular portion of element 52, such that its axial position relative to axial position of its surrounded tubular element of 52 causes struts to withdraw inwards, closing flush, aspiration and protection cover 51 (transparent in this illustration) also inwards to close off space between flush, aspiration and protection cover 51, which is connected to struts of element 52, and the larger diameter area of cannula 50 near orifices 60 as shown and according to embodiments. It should be noted that struts of element 52 may each be made of two parts, one part of which may be connected to cover element 51 at the surface of cover element 51, with a second part connected to the central shaft 50 and also contain flexible material between the central shaft 50 and the first part of each strut 52, as further illustrated in FIG. 62 below, and in order to create segmented spaces within an expanded cover element 51.

Figure 58:
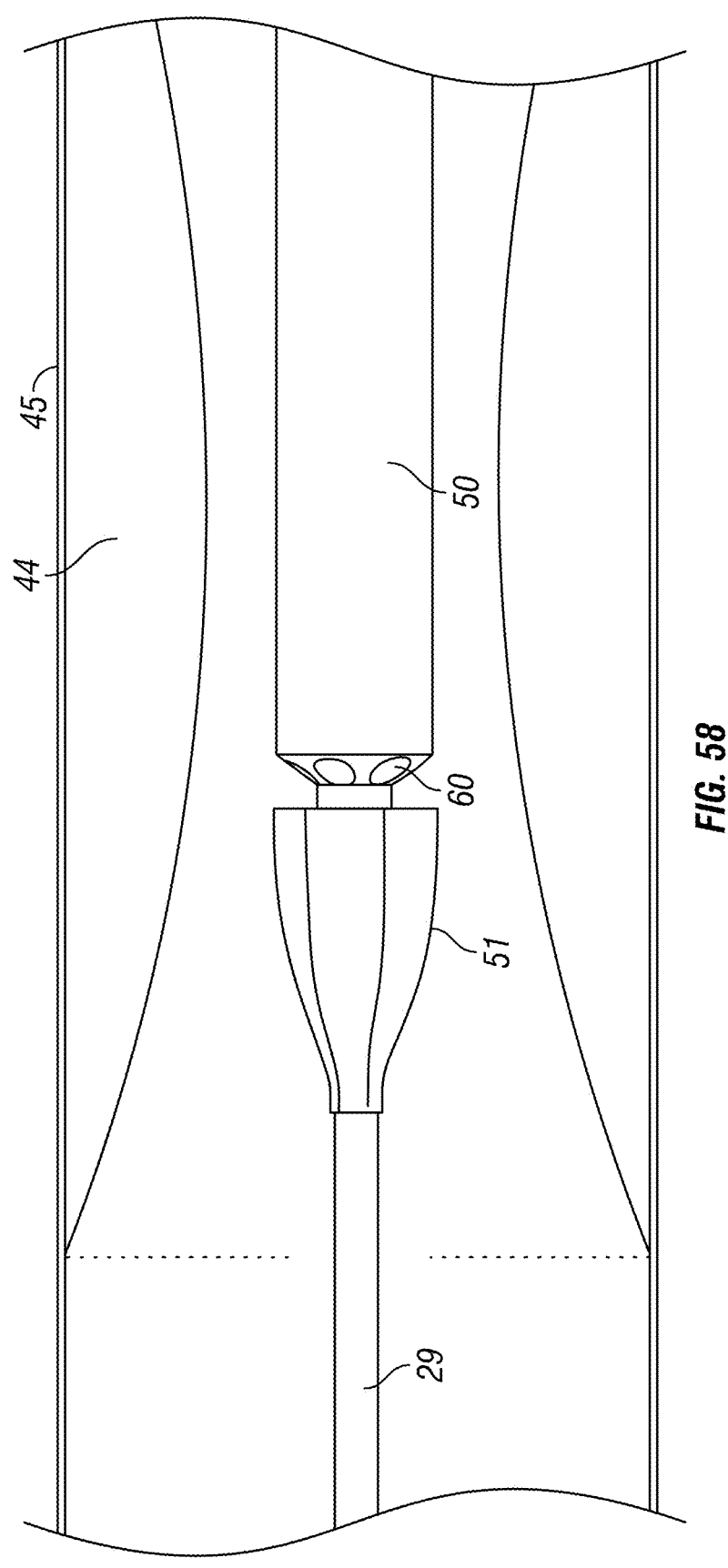
FIG. 58 is a side view of an assembly including elements of FIGS. 56 and 57 which are in a partially extended position further revealing additional elements shown as orifices in a face of a tubular element of the assembly, proximal to a protection element of FIGS. 56 and 57 according to embodiments.

FIG. 58 shows extension away from cannula 50 of flush, aspiration and protection cover 51 revealing orifices 60 to be located farther from the proximal edge of flush, aspiration and protection cover 51 according to embodiments. In this position, flush flows, which may be of relatively powerful forward jet-like in nature, and may also include other media, including simple microbubbles of carbon dioxide gas in solution and also may include other agents such as thrombolytic and antiplatelet medications for example, may be controllable both in direction and intensity by controlling the degree of separation between the two according to embodiments.

Figure 59:
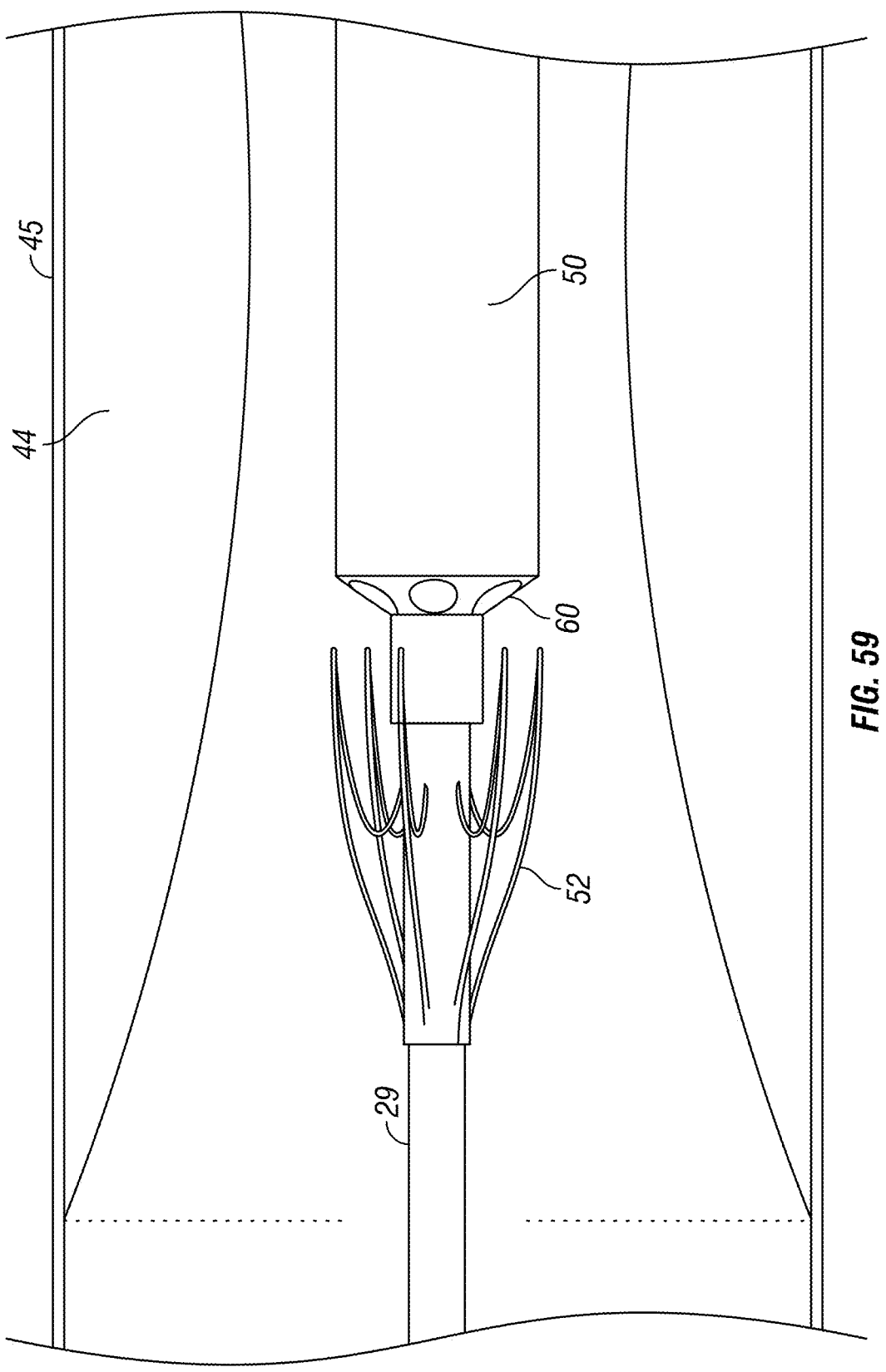
FIG. 59 is a side view of an assembly of FIG. 58 with an outer covering transparent revealing the separation of the protection element from the orifices located more proximally according to embodiments.

FIG. 59 illustrates the relationship further with a transparent outer cover 51 over struts 52, revealing flow directing elements to direct and isolate injected and activated agents that may act physically with high mechanical index impulses for thrombolysis, dissolution and clearing or chemical agents for the same purpose, that using this mechanism may act directly on a local segment of a tubular structure affected by the process, while isolating, trapping and aspirating the resulting materials removing them from the area completely to prevent escape into regions proximal or distal to the isolated area where their effects may be harmful and difficult to reverse once escaped, according to embodiments. Also revealed in this illustration is the control of addition of fluids into the area isolated by elements in this illustration relative to that aspirated, including any debris included as a result of flows of fluids against diseased areas within a vessel 45. Controlling the flow rates, aspiration forces and gap between flush, aspiration and protection cover 51 for example and orifices 60 together modulate relative flow and aspiration rates according to embodiments.

Figure 60:
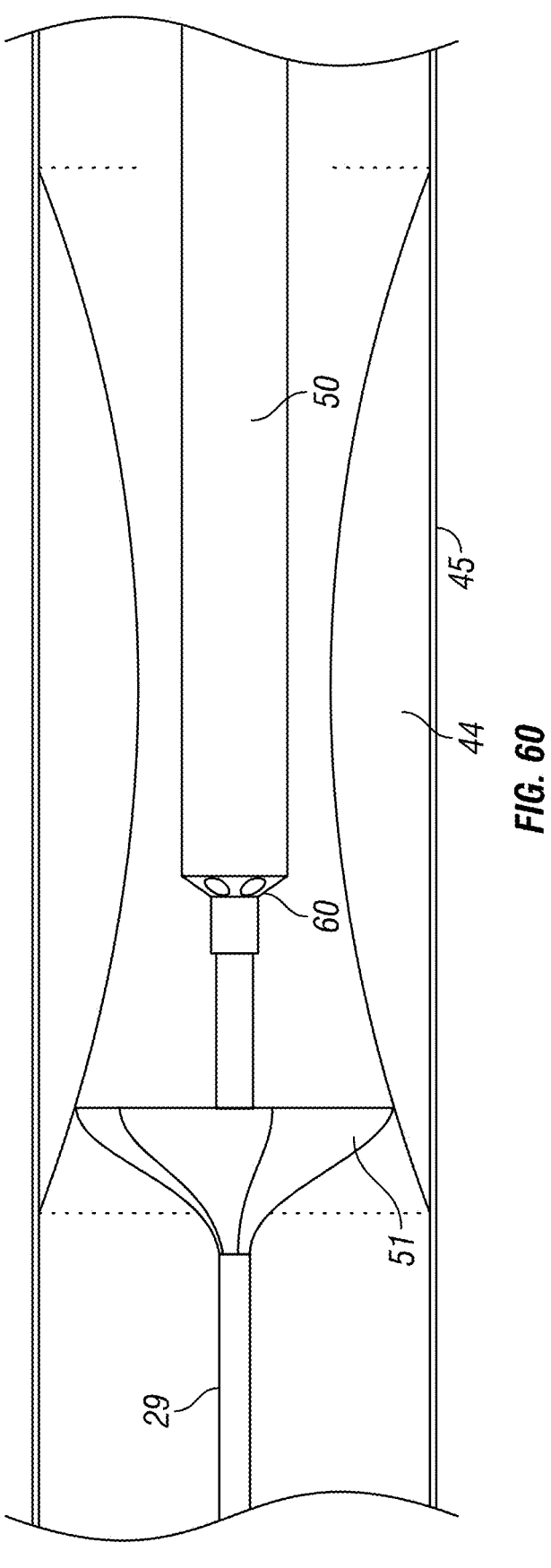
FIG. 60 is a side view of an assembly of FIG. 58 with its covering deployed and extended shown within a partially obstructed tubular structure such as a blood vessel, with its other element and its orifices also visible in an embodiment.

FIG. 60 illustrates the capability to deploy flush, aspiration and protection cover 51 into a shape that promotes a recirculation pattern within the space between the orifices of 60, which as will be shown subsequently. The flush, aspiration and protection cover 51 may also generate aspiration forces, which are controllable by varying the position and degree of deployment of flush, aspiration and protection cover 51, which flows are further manipulated and controlled with deployment control strut elements 52. In the case of thrombus or other loosely attached debris, it is desirable to clear any such materials by flushing and aspirating with powerful streams of fluids, while protecting downstream, smaller caliber vessels from being plugged up with such debris, and according to embodiments.

Figure 61:
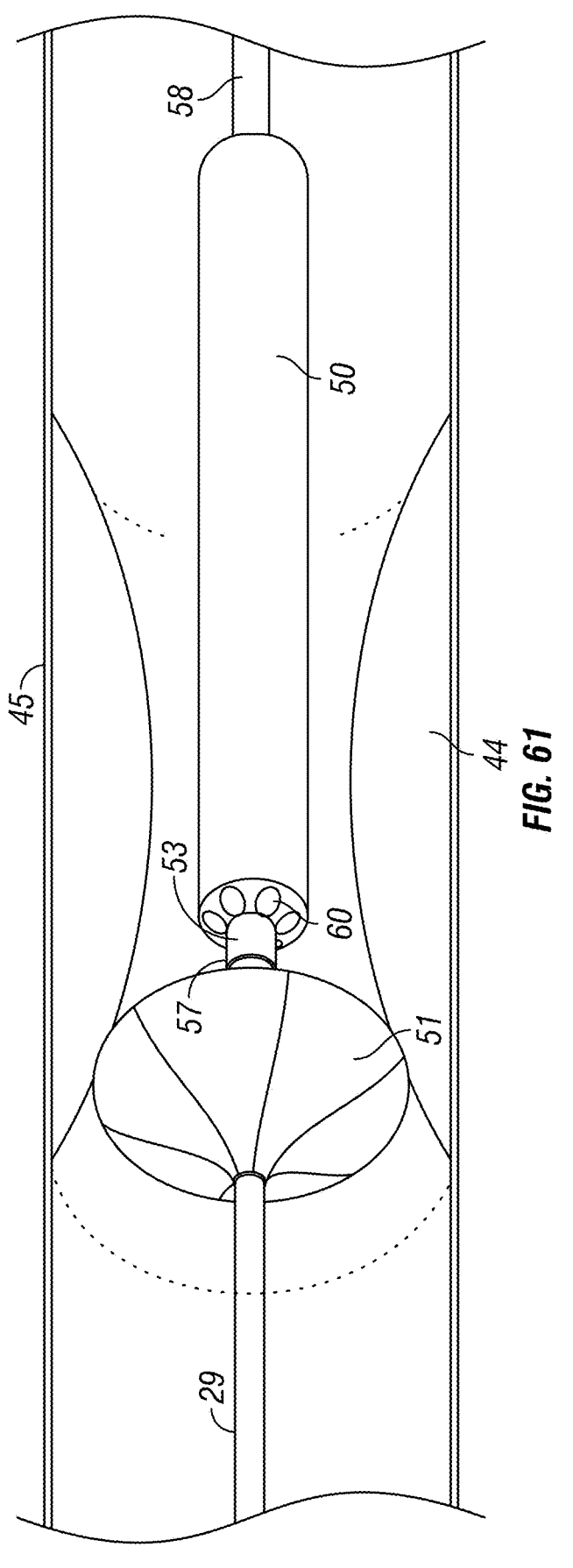
FIG. 61 is a profile view from the front of an assembly of FIG. 60 revealing the elements of the orifices arranged radially projecting towards an extended element according to embodiments.

FIG. 61 is a perspective view from the front looking back to further illustrate the mechanisms as well as to point out that space 57 between cannula 58 and larger cannula 53 is available for flush fluids and any agents desired especially where these agents may be able to be used in higher concentrations given the local isolation of a segment of interest, while as will be seen subsequently, orifices 60 have the capability for high speed flow and aspiration according to embodiments, to remove such agents when they are no longer needed, along with any harmful obstructing materials responsible for an acute occlusion, in this case in a vascular space. Additionally, in the case of utilizing high mechanical index impulses, laser energies and others that may disrupt and help remove such offending materials from the area, the open central lumen is also available for delivery of activating instruments, for example in the case of microbubble collapse to create sheer forces, (sonothrombolysis) a surface high frequency ultrasound transducer to create such integrity-disrupting forces may be sufficient for the dissolution of micro-thrombi, however in the case where a more local source of energy may be required, a transducer may be introduced (not shown here) more closely to the area via the central lumen of cannula 58 for the purpose according to embodiments.

Figure 62:
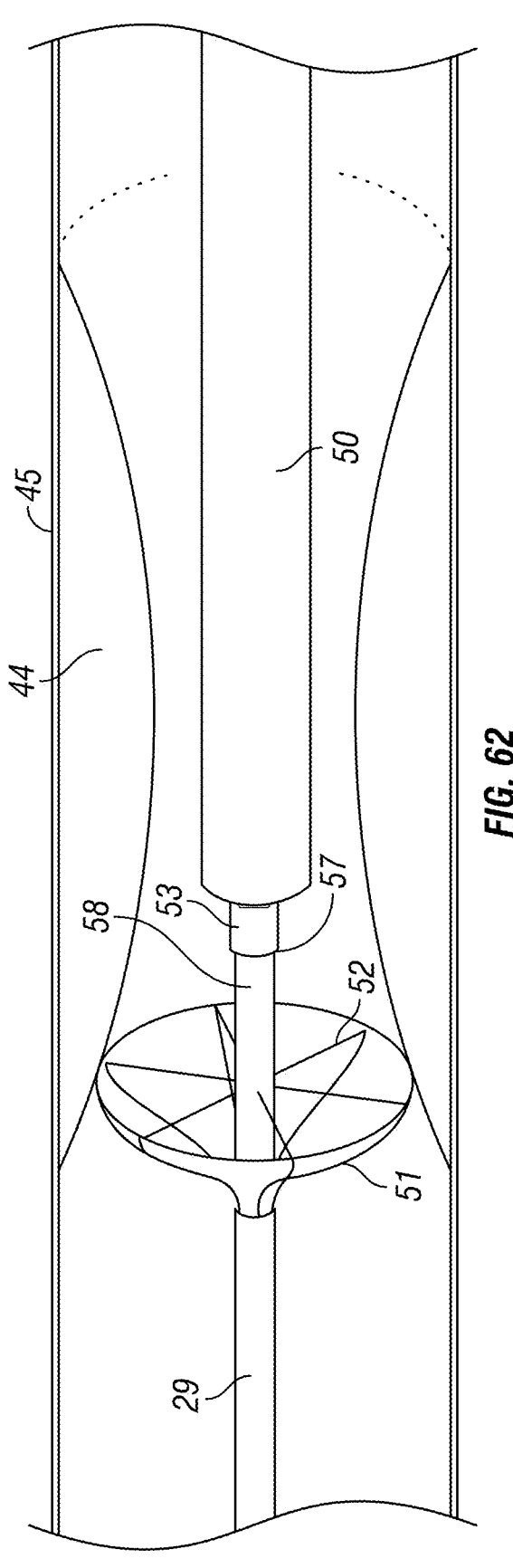
FIG. 62 is a profile view from the rear revealing strut deployment elements of an assembly of FIG. 61 according to embodiments.

FIG. 62 shows the same assembly as in FIG. 62 from the rear illustrating the septation spaces created by elements 52 that may serve to stabilize, vector and concentrate flows outwards while optimizing isolation and augmenting flows in the return path for aspiration, according to embodiments.

Figure 63:
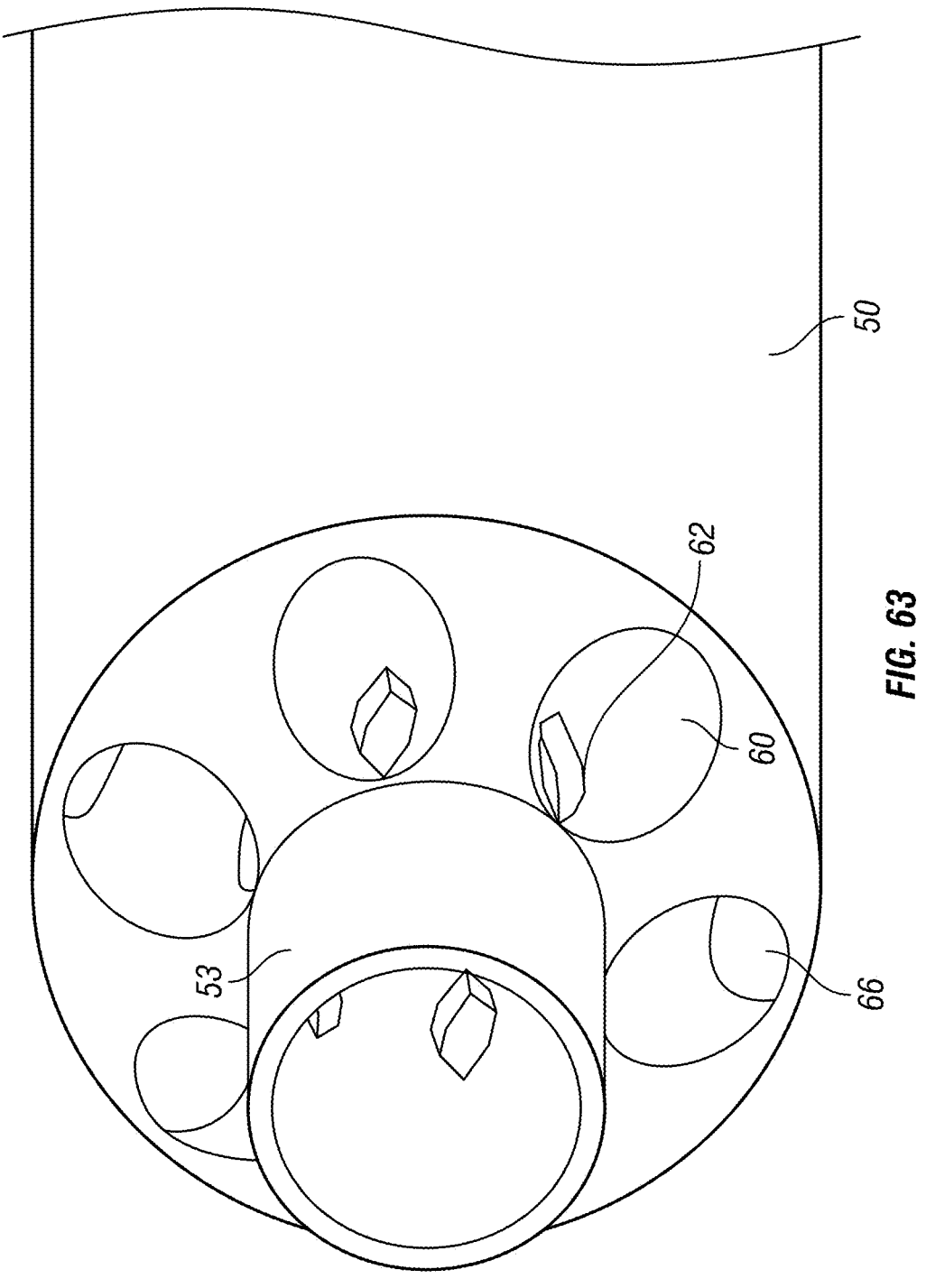
FIG. 63 is a close-up perspective view from the front of an element of an assembly of FIG. 61 with other elements removed to reveal the internal structures of the element according to embodiments.

FIG. 63 reveals inner details of catheter 50 including orifices 60 as well as internally placed hydrodynamic shapes 66 that, by directing flows over such shapes, create low pressure areas through low pressure orifices 62 for aspiration according to embodiments.

Figure 64:
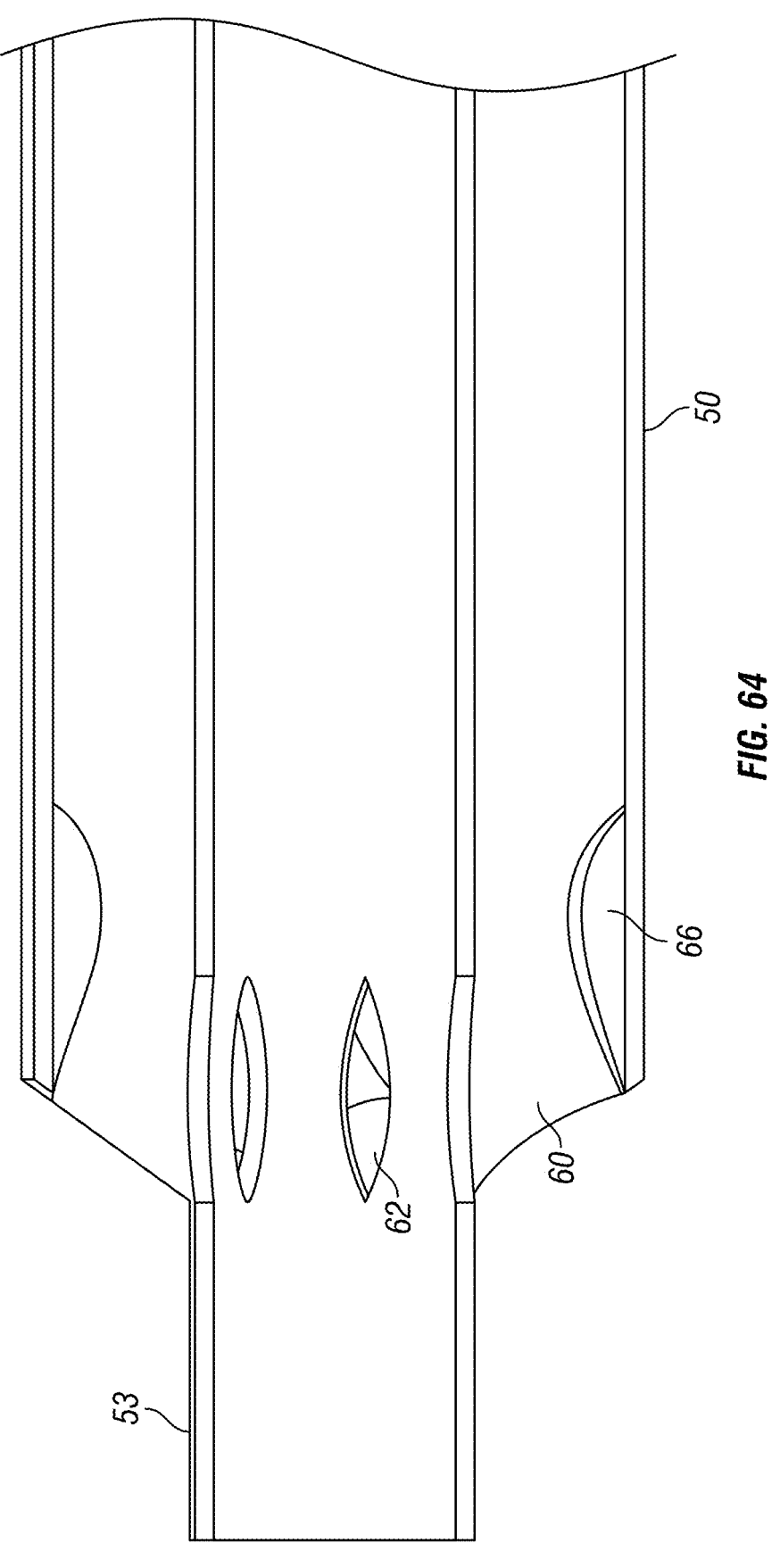
FIG. 64 is a section cutaway view of the element of FIG. 63 shown from the side revealing other internal details and shapes according to embodiments.

FIG. 64 is a sectional view of catheter 50 showing the internal chamber where shapes 66 create outwardly directed outbound flows that may include chemical agents, as well as activated physical disrupters, which following successful dislodging and dissolution of clinging materials from vessel walls, recirculate via flush, aspiration and protection cover 51 and 52 shown previously and then return for complete removal via aspiration through low pressure orifices 62 where such flow generated aspiration may be augmented by proximal vacuum sources, according to embodiments.

Figure 65:
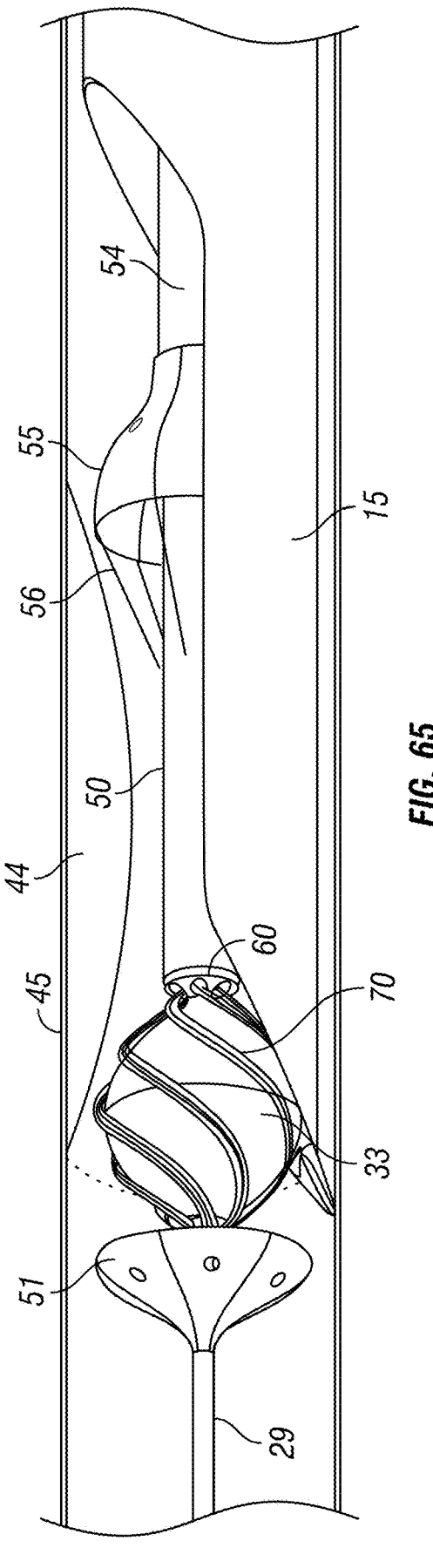
FIG. 65 is an assembly including elements of FIG. 60 as well as another excisional cutting and optionally imaging chamber supported with an expandable element inside its perimeter, supported by a scoopula and positioned beyond a partially occluding obstruction within a vessel such as a vascular structure, as well as a proximal extended element with its deploying members, similar to that shown distal to the cutting excisional, element, according to embodiments.

FIG. 65 is an illustration of an expandable, spirally deployable cutting element 70, which may function as a device introduced through the central lumen of device 10, whose function and deployment is similar to that previously fully described in U.S. Pat. No. 8,992,441, incorporated by reference in its entirety herein, as previously mentioned above, and as shown in this figure in fully deployed state within a vessel supported by an imaging, excisional assembly 10 of FIG. 1, and supported internally with an expandable inner chamber 33 that is transparent and imaging-capable, according to another embodiment. Also shown is a flush, aspiration and protection cover 51 and now also shown is an additional proximal expandable cover 55 to further isolate an area by protecting potential proximal escape of harmful materials, with its strut deploying elements 56 shown fully deploying into expanded configuration, cover 55, which itself is attached to cannula 54 according to embodiments. Upon rotation, excisional cutting device 70 may be retracted from its position distally through the area of the obstructing disease materials 44 in a vessel 45, to excise such materials. Device 70 in this way may work together with flush, aspiration and protection cover 51 and proximal expandable cover 55 to isolate, protect, capture and present for transport such obstructing and potentially embolic materials, according to embodiments.

Figure 66:
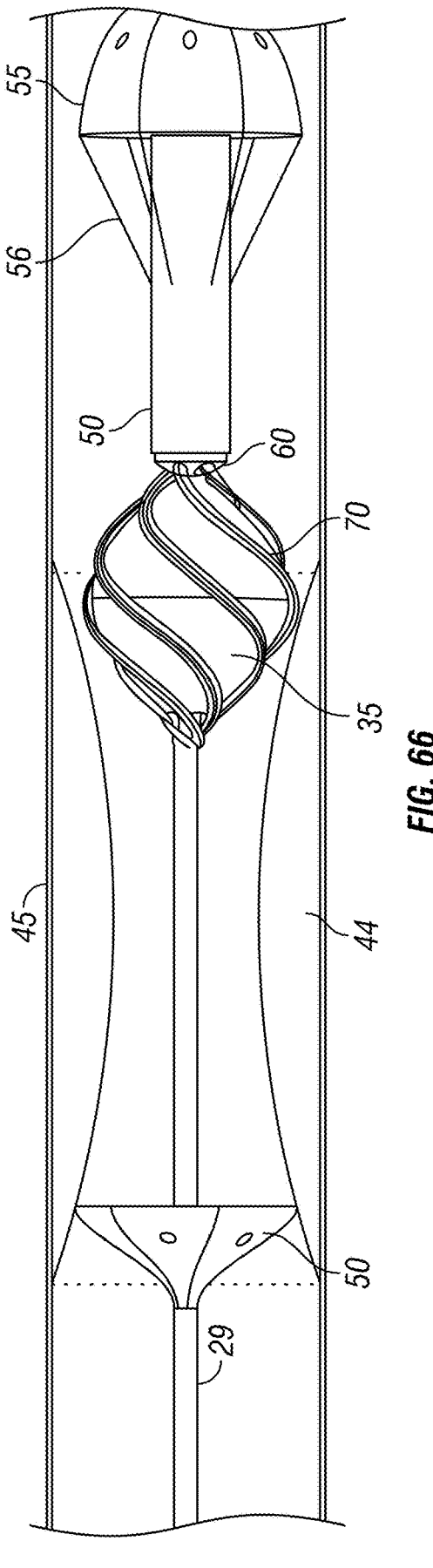
FIG. 66 is a side view of elements of FIG. 65 arranged about and within a partially occluded segment of a tubular vessel without the addition in this case of a supporting scoopula, according to embodiments.

FIG. 66 shows the above elements in a standalone configuration where they may be deployed and utilized to isolate, excise and capture by rotating ablation all obstructing materials 44 as shown in vessel 45, according to embodiments.

Figure 67:
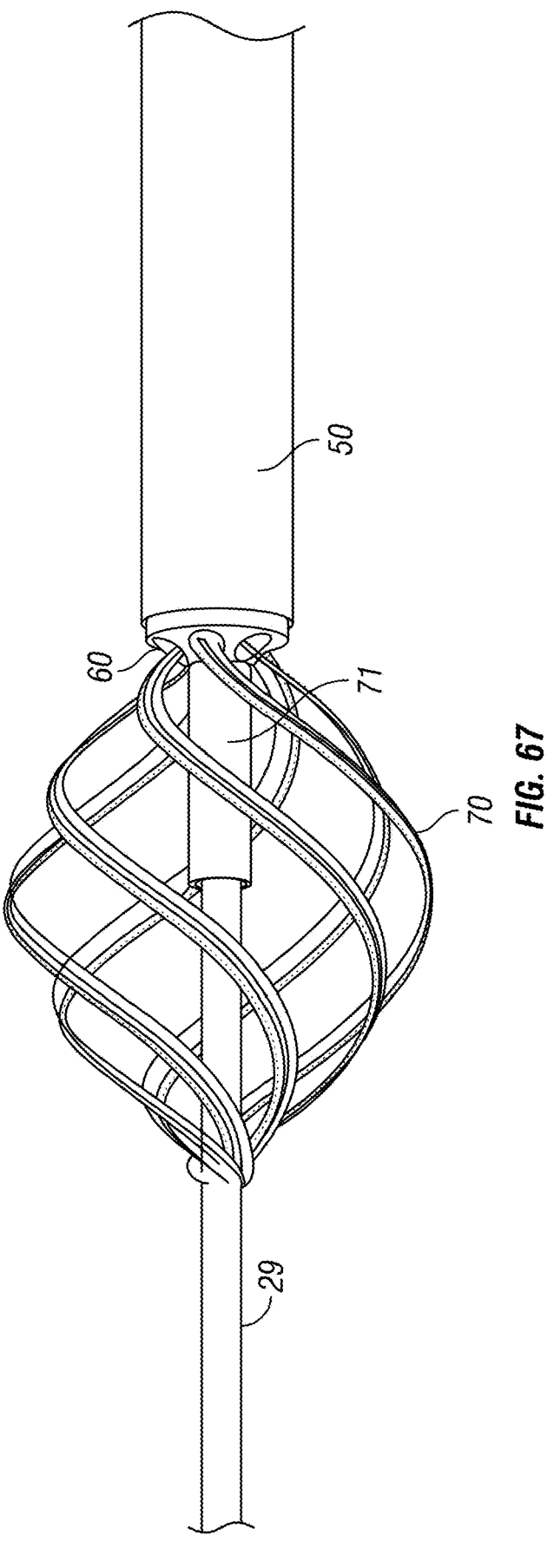
FIG. 67 is a side view of additional coaxially placed elements internal to the excisional cutting elements of FIG. 65, according to embodiments.

FIG. 67 shows, for further clarity, the way that the individual elements of device 70 may be deployed and retracted in a spiral fashion, with in this case the blade elements denoted by 67 in this figure shown somewhat more flattened in shape, due to the flexible nature of the blade elements of device 70 while a guiding wire is shown extended distally, all of which emanate from within sheath-cannula 50 according to embodiments.

Figure 68:
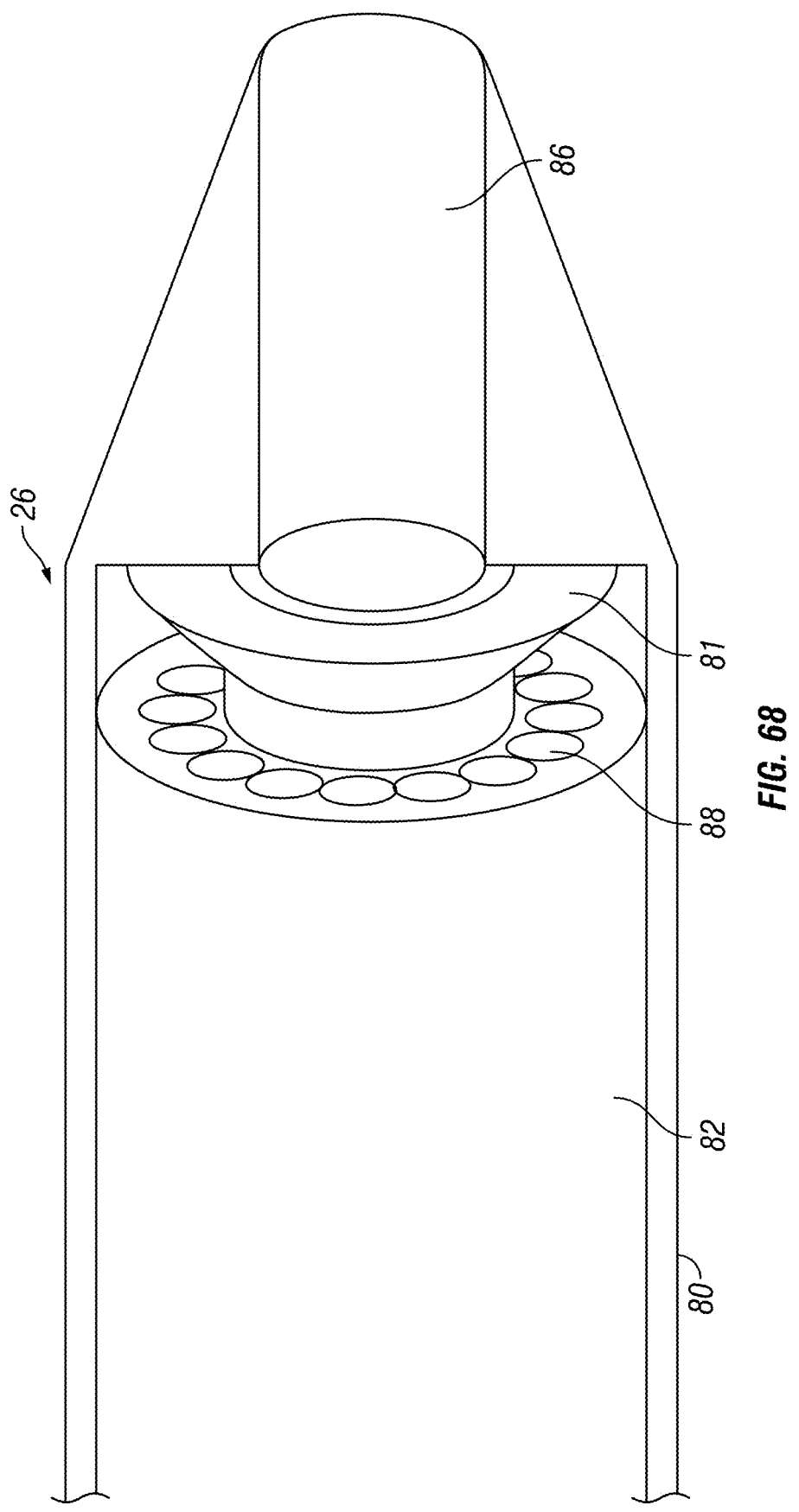
FIG. 68 is a profile view of an imaging catheter with an open internal lumen and imaging fibers arranged radially aiming towards a concentric reflecting element or elements, a central lumen terminating in a tapered nose cone according to embodiments.

FIG. 68 is an illustration of an additional configuration of an imaging element 26 that has been shown and described herein. In the configuration 80 shown in FIG. 68, however, it is optimized for coaxial imaging, simplicity of manufacture and operation. The imaging element may be configured to be independent of rotation of other elements, and may comprise an array of radially placed optical fibers 88 within a flexible covering 82 that may have an inner coating to contain any stray electromagnetic pulse-waves, with fibers 88 (which may likewise be surrounded with reflective coatings) transmitting to and receiving back from, a circular single or multiply constructed reflecting element 81, which receives optical energies from fibers 88, reflects them outwards into tissue and then receives altered (e.g., reflected and scattered) light back, and then in turn reflects these back to rearward image transmitting fibers for comparison, analysis and image generation by the actions of the generating OCT engine and the receiving and processing analytics that create useful tomographic images. In this case, conventional mechanical rotational signaling may occur with a single outbound and inbound fiber. However, pulse generation and reception may be provided digitally with fibers that need not rotate, in combination with a reflecting ring that likewise need not rotate in order to generate full 360 degrees of view while also permitting rotational elements to occupy a central open lumen according to embodiments. The integrity of multiple small imaging optical fibers, positioned within a flexible catheter, potentially spiral wound or straight for example, may be easier to protect during flexing of the assembly particularly in interventions that may require such flexibility, in the present arrangement and according to embodiments. Additionally, fibers may be arranged such that some may be dedicated to imaging alone, while others may be used to provide high energy electromagnetic particle waves to ablate, excise or dissolve materials that are causing harm by obstruction or other means, to normal structures. Another option that can be used according to embodiments includes the ability to utilize fibers for multiple rapid toggling between therapeutic and diagnostic and guidance functions. Therapeutic pulses can be quickly or in real time, guided and modulated with integrated imaging according to embodiments. Furthermore, the reflective face of reflective element 81 need not be singular, rather, the face of reflective element 81 may be constructed with multiple reflective bevels which may themselves be arranged in an arrangement of rings or individual reflective segments of element 81 may be beveled in radial sections next to one another around the circle, or there may be a combination of the two, even if the circular reflector is of a single piece with multiple grind angles, according to embodiments. Furthermore, the axial arrangement with respect to distance of such individual reflective segments may be individualized according to embodiments. Axially deposed reflective segments next to one another circumferentially for example, may be located at different levels in the axial plane, which then may be utilized to form arrays along both an axial plane (fore and aft of a reference point) and circumferentially. Images from reflective segments thus axially arranged and circumferentially arranged individually around the ring, may then be used as the basis for forming 3 dimensional images with refresh rates limited in practice only by processing speed and computing power according to embodiments. Such variations may be utilized to image and apply therapeutic pulses to and from various areas and angles with respect to the axial orientation of the catheter so equipped according to further embodiments. A full circle, partial circle, or partially circular, array may be placed on beaks 13 for example, together with their transmitting and receiving fibers in a way that maintains alignment between fibers and reflectors as well as alignment with the planes of the beak(s) element(s) as beak(s) 13 are rotated and actuated, which may make imaging and coring alignment directly linked, according to embodiments. Likewise, as a circular reflecting apparatus, reflective element 81 may be independently movable with respect to fibers proximal to it in the catheter according to embodiments, such that a variety of areas along an axis may be imaged or treated, for example, were there to be light activated agents delivered to a vessel wall, these areas could quickly be "painted" with electromagnetic energies using the freedom of movement of reflective element 81 according to embodiments. At the same time, access channel 86 could be available for simultaneous therapeutic or imaging elements that may be forward excising, delivery or forward looking and guiding according to embodiments. Fibers, whether diagnostic or for treatment, can be placed around an open central lumen, freeing up the central lumen for other working elements such as borers for a chronic total occlusion clearing, or for introducing elements distally such as other imaging or other working mechanisms (IVUS, physiologic, temperature sensing, flow measuring, debris catchers, tissue removers, wall expanders whether absorbable or permanent, among others). Furthermore, selected fibers could be utilized in a way that references virtually, the angle of the scoopula, including the position of its edges, since scoopula may be of a variety of shapes and configurations, and whether the presence of the scoopula is in the same position or not according to embodiments. In one example, preplanning of placement, including rotation and depth of working elements such as a scoopula, could be made prior to advancement of any or all of these working elements according to embodiments.

Figure 69:
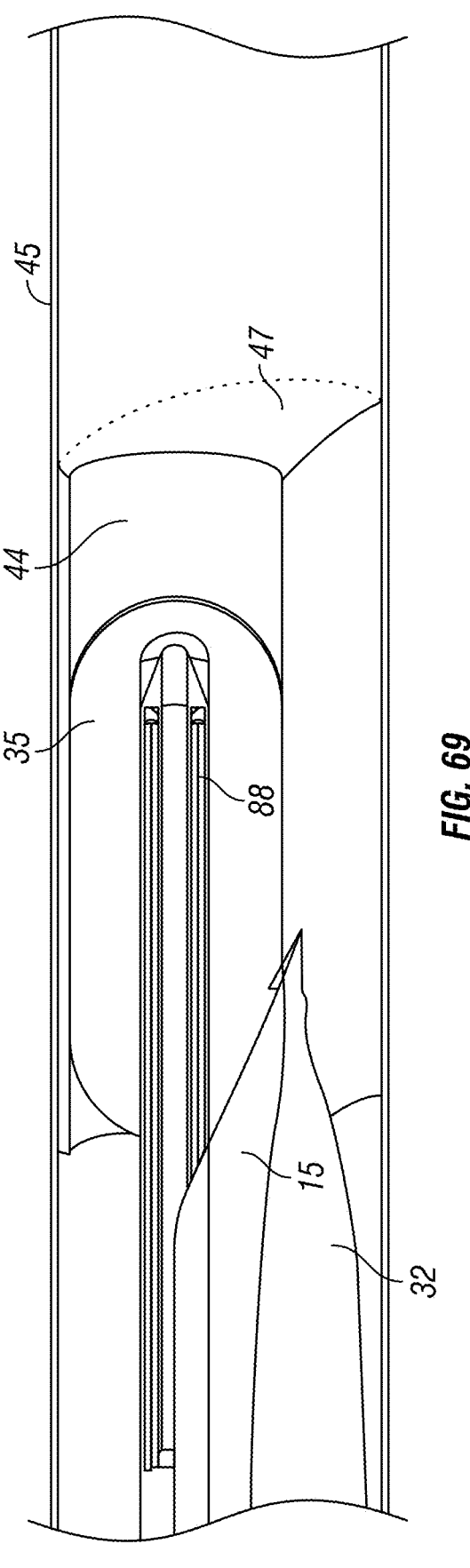
FIG. 69 is a side view in cutaway sectional illustration showing an imaging catheter of FIG. 68 positioned inside an expandable, transparent chamber within a partially occluded vessel aimed at the circumferential transmitting and receiving reflective element or plurality of elements, as well as an open central lumen for access through which other working elements such as a guidewire or other interventional elements according to embodiments and supported by a scoopula portion of an excisional imaging assembly of FIG. 49 according to embodiments.

FIG. 69 is an illustration of the above apparatus as shown in a working assembly of FIG. 1, including in this instance an expandable, transparent imaging chamber element 35 with parallel, distortion free sides that, by nature of its unobstructed, undistorted inner space, similar to that of element 33 previously described above, may extend the range of an OCT element such as element 80 with its multiple fibers 88, or an ultrasound element for another example, by creating a uniform and undistorted medium optimized for the imaging modality, between the source of energy waves of any frequency along the electromagnetic spectrum and the tissues being interrogated, according to embodiments. For example, in a pulmonary application where an air interface may obstruct ultrasound transmission, bringing an integrated chamber providing an optimal fluid medium directly to an area of interest within which a transducer may operate, may eliminate the need to continuously flush the area with fluids to create the same ultrasound pathway. In the same way, in a blood vessel and in the case of OCT modality, excluding blood between the OCT wire or catheter by allowing it to operate within a chamber of transparent medium, while positioning the chamber directly adjacent to the tissue of interest, may likewise eliminate the need for constant flushing away of blood flow to achieve the same relief of signal loss and distortion. These imaging modality working ends may be housed and utilized, shown in this example in a subtotal occlusion by materials 44 in a vessel 45, or they may be placed in any environment where it is desired to control the medium and pathway between signal outputs and inputs, such that any unwanted interfaces or intervening media can be minimized or eliminated altogether, for example, were the embodiments placed in any area of application where any non-uniform materials would normally exist in the signal pathway that would ordinarily diminish the penetration and efficiency of such an imaging modality, that limitation could be partially or even totally minimized by including at a minimum, one of the embodiments of chamber 33 (one of which is shown in this illustration and others), working together with enabling additional elements capable of positioning such a portable medium transmitting chamber remotely to any site desired, thus providing a self-contained apparatus for optimal localized imaging, according to embodiments.

Figure 70:
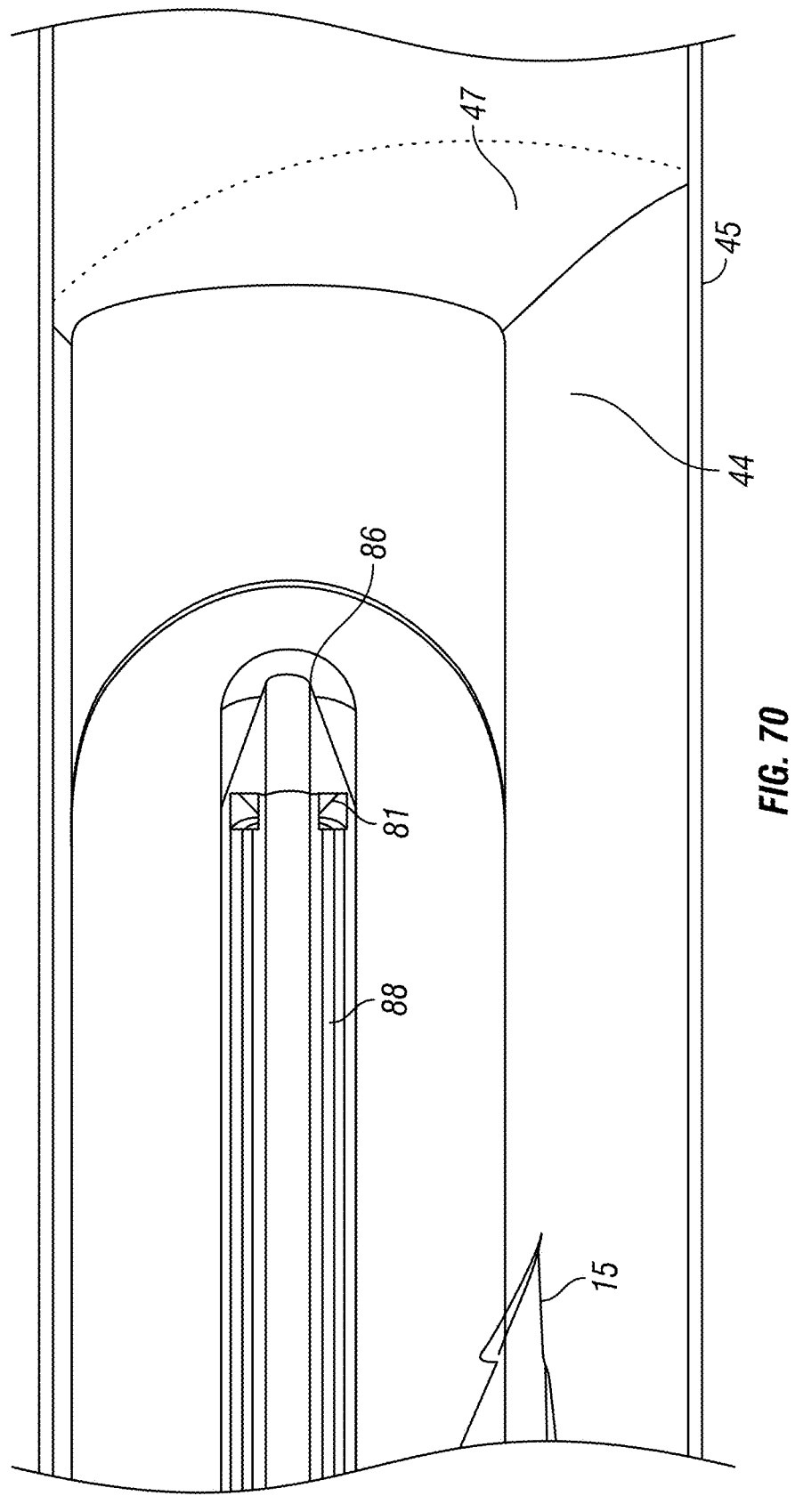
FIG. 70 is a closer view of an imaging assembly of FIG. 68 including an imaging catheter and supporting scoopula of an excisional imaging device of FIG. 49 according to embodiments.

FIG. 70 is a closer up view of element 80 of FIG. 68 with its fibers 88, circular receiving, reflecting, transmitting element 81 and its central lumen and nosecone 86 also all shown being supported and elevated by scoopula 15 according to embodiments. It should be noted that the illustrated central lumen 86 can be utilized by any of the excisional, ablative, dissolving or other physiologically altering devices that dimensionally may be introduced, directed and supported by such a space according to embodiments.

Figure 71:
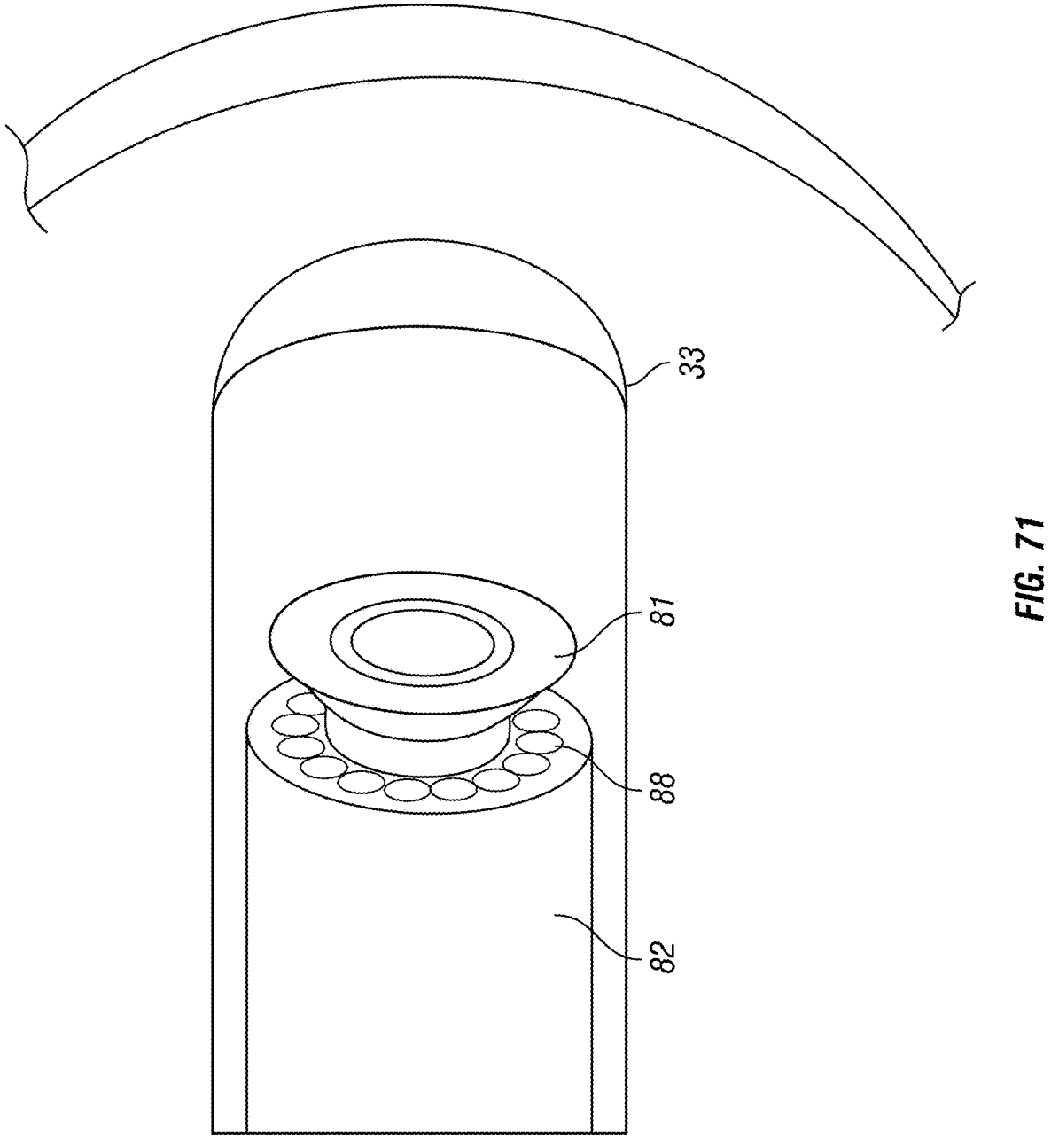
FIG. 71 is an even closer perspective view of an imaging catheter revealing its circular coaxial reflecting and transmitting fibers arranged as in FIGS. 68, 69 and 70 above, and within an outer expandable, transparent imaging chamber, according to embodiments.

FIG. 71 is another illustration of a device 80 of FIG. 68 with its outer covering 82, its optical fibers 88 and optical reception, reflection and re-transmission element or elements 81 shown within expandable, transparent imaging and extending chamber 33. In addition to imaging capabilities, laser and ultra-short wavelength modalities may be transmitted and feedback controlled utilizing multiple layers or sections of fibers to ablate materials using this configuration and in potential combination with imaging devices of a range of conventionally configured catheter and wire imaging modalities, introduced and positioned via the included open central lumen, according to embodiments.

Figure 72:
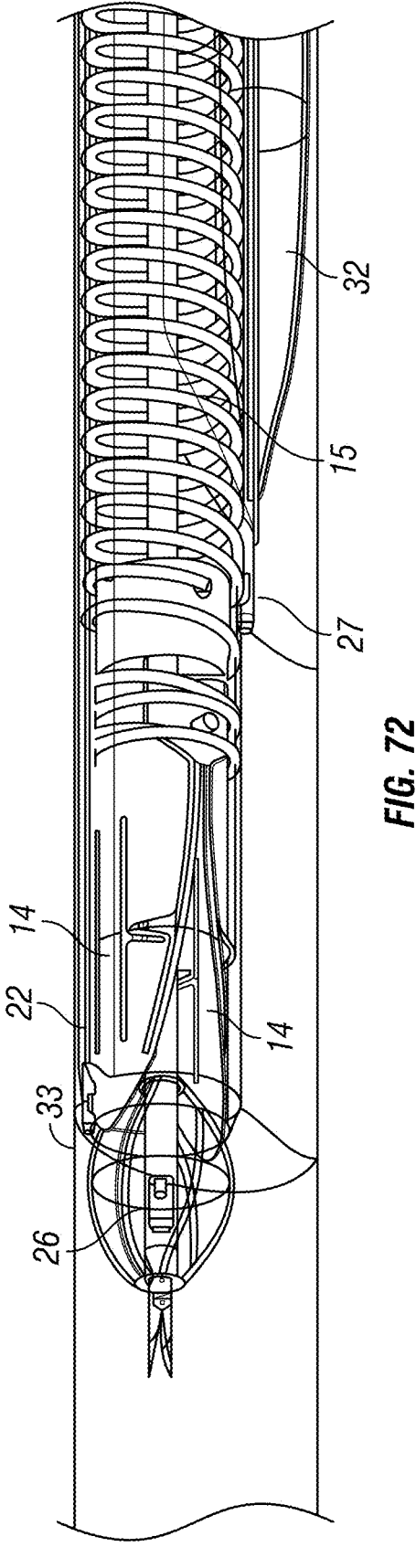
FIG. 72 is a perspective view of an imaging, excisional assembly within a new channel in a previously totally obliterated space in a tubular structure such as a vascular total occlusion according to embodiments.

FIG. 72 is an illustration of a device 10 with its stabilizing elements shown together with its guidance elements, including in this case, OCT and IVUS (26, 27), depth and elevation control elements, non-rotating sheath element 22, Scoopula 15 and expandable, flow enabling element 32 in a formerly totally occluded vessel, that is now shown as having partial restoration of original lumen diameter, at a stage where according to methods, may now continue or proceed in a remotely controlled, automated series of steps including repositioning utilizing each of the elements illustrated, followed by excising with beak(s) 14 of work element 13 as previously described, and rotational control and stability being provided by an outer sheath 25 (not shown in this illustration) alone or in combination with expandable, flow enabling element 32, to a precise depth and direction more of the material with each repetition of the logical steps with the ultimate end result being to remove as much of the remaining material as would be optimal for flow and healing, according to embodiments.

Figure 73:
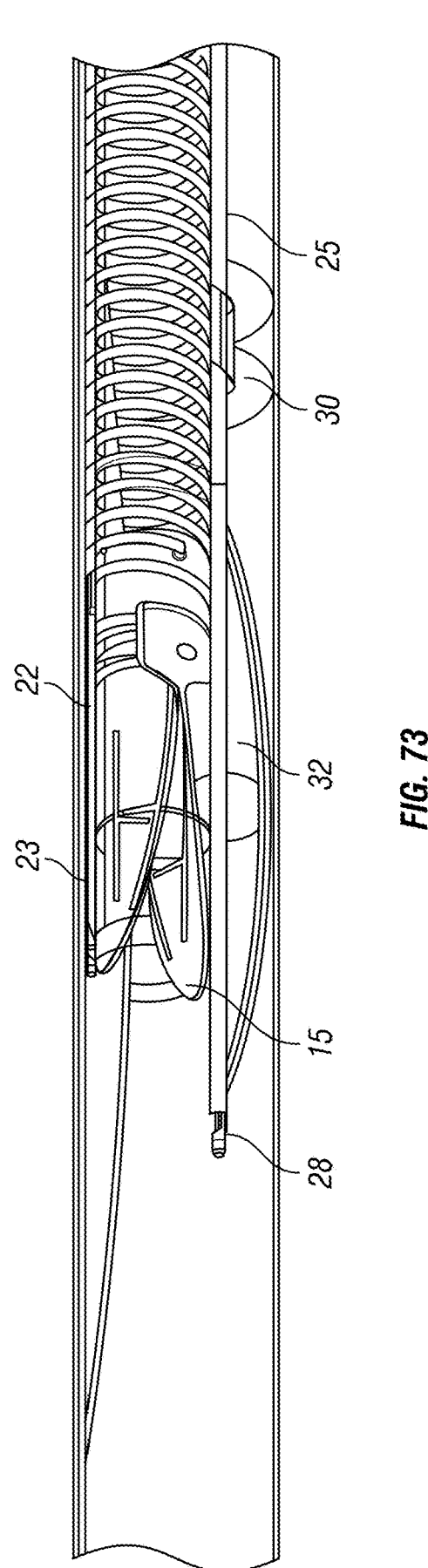
FIG. 73 is a perspective view of an imaging, excisional assembly with an additional asymmetric expansion, elevation and control element according to embodiments.

FIG. 73 is a perspective view of a device of FIG. 1 together with elements needed for the specific purpose of clearing asymmetrically located materials encountered initially or remaining from earlier excisions, achieving maximum control of positioning in rotation, elevation, and longitudinal excursion as well as precision in depth control, the execution of which is shown by illustrating a combination of imaging represented by generic imaging element 28, elevation, stabilization and flow control with expandable element(s) 32, further elevation, flow control, local rotational stability and angle of excision manipulation by an expandable cuff 30, in this case shown proximally but which could also be duplicated distally, along with precise depth control utilizing asymmetry of the circumference of NRS 22, in this case as shown with a larger diameter area contributed by lumen 23 in the NRS 22, by rotating independently, NRS 22 to create as little or much standoff between the cutting elements and the materials to be removed as desired according to embodiments. With elevation, rotation and longitudinal positioning and flow control established and stabilized with scoopula platform 15 as provided by expandable element(s) 32, along with further stabilization in those parameters as well as angulation by element 30 acting on outer flexible tube element 25 of a device of FIG. 1, rotation of NRS 22 combined with degree of exposure of beak elements 14 can be utilized to fine tune depth control. All of these parameters may be factored in and manipulated in an automated process based on precise in-situ imaging to refine to a maximal degree, precision control of all aspects of an excision procedure, according to embodiments.

One embodiment, therefore, includes using a scoopula-based work elements configured to create and isolate a work area within a vascular structure, while selectively allowing or disallowing the flow of fluids in the thus isolated area.

The creation of the "work area" protects the vascular walls that we don't want to damage and captures debris from whatever interventional work elements are introduced in any number of different stages and procedures, all of which may be introduced to the work area site thus established through the central lumen of the work element or elements that establish and maintain the work area site. This is in stark contrast to the current approach, where a single device tries to do it all, i.e., coring, shaving, capturing, expanding, re-establishing blood flow, preserving blood flow, etc. The devices and methods described and shown herein, according to embodiments, include a device, with a minimally invasive structure that first creates that protected work area, and that can be moved to successively expose additional incremental work areas, and that serves as the universal conduit for all kinds of different specialized work elements to be successively introduced through its central lumen in as many successive steps as are necessary to complete a gentle, thorough removal of blocking plaque or materials while preserving the vascular wall architecture and re-establishing or improving blood flow as quickly as possible.

Embodiments, therefore, create different types of "work area establishment" and a "isolating/debris capturing" work elements and a number of different interventional work elements configured to clear obstructive material from a first isolated and protected work area by being introduced through the work element that establishes the "work area".

One embodiment, therefore, is a device, comprising an outer flexible tube defining a longitudinal axis; a rotatable scoopula disposed within the outer flexible tube and defining an open side portion; at least one inflatable support element attached near a distal end of the rotatable scoopula; an inner sheath disposed within the rotatable scoopula and configured to move parallel to the longitudinal axis; a first pair of first and second rotatable and articulable beaks disposed within the inner sheath and partially extending into the open side portion of the scoopula, the first pair of first and second rotatable and articulable beaks being configured to cut tissue present within and beyond the open side portion of the scoopula by selectively assuming an open and a at least partially closed configuration while rotating and an expandable and collapsible cutting and imaging chamber disposed at a distal end of a central tube that is disposed coaxially between the first pair of first and second articulable beaks, the chamber being configured to enclose a removable imaging device within a volume of fluid and to move parallel to the longitudinal axis away from and back against the first pair of first and second articulable beaks.

According to further embodiments, the chamber further may include a plurality of curved blades disposed on a portion of an outer surface of the chamber that faces the first pair of first and second articulable beaks, the first and second articulable beaks being configured to engage with the plurality of curved blades when the chamber and the first and second articulable beaks are moved into contact with one another. The device may further comprise a tube defining a lumen configured to receive a guide wire. The device may also further comprise the removable imaging device disposed within the volume of fluid enclosed by the chamber. For example, the imaging device may include an optical coherence tomography imaging device including a rotating mirror or a phased array of circularly-arranged light sources disposed around a stationary reflective element. Other imaging modalities and devices are possible. For example, the imaging device may include an ultrasound imaging device disposed within the volume of fluid enclosed by the chamber. The chamber may be further configured to define a central lumen that emerges at a distal end of the chamber. The device may further comprise a second pair of first and second articulable beaks that are smaller than the first pair of first and second articulable beaks and that may be configured to be advanced within the central tube through the central lumen past the distal end of the chamber. The second pair of first and second articulable beaks may be independently articulable, movable and rotatable to cut tissue distal to the chamber. The second pair of the first and second articulable beaks may be configured to assume an open configuration to core through tissue distal to the chamber and to assume a closed configuration to part off cored tissue. An expandable cuff may be disposed proximal of the first pair of first and second articulable beaks on the outer flexible tube. The inflatable support element(s) may include a first inflatable support element and a second inflatable support element spaced apart from the first inflatable support element to define a through channel therebetween. For example, the at least one inflatable support element may be (generally) pontoon-shaped. The chamber may be further configured to deform against one side of a passageway when the inflatable support element(s) are inflated to press against an opposing side of the passageway.

Another embodiment is a method, comprising advancing a device within a vasculature to a target region, the device comprising a scoopula comprising an open side portion, a first pair of rotatable first and second articulable beaks that partially extend into the open portion of the scoopula, at least one inflatable support element attached near a distal end of an outer surface of the scoopula and an expandable and collapsible cutting and imaging chamber disposed at a distal end of a central tube coaxially disposed between the first pair of first and second articulable beaks; inflating the chamber and at least one inflatable support element such that the chamber may be pressed against a surface of the vasculature distal to the target region; imaging the vasculature using the chamber; rotating the first pair of first and second articulable beaks; and cutting tissue that comes into contact with the rotating first pair of first and second articulable beaks within the open side portion of the scoopula to a selectable depth that may be at least partially dependent on the inflation of at least one of the chamber and of the at least one inflatable support element.

The chamber further may include a plurality of curved blades disposed on a portion of an outer surface of the chamber that faces the first pair of first and second articulable beaks, and the method may further include bringing the first pair of first and second articulable beaks into contact with the plurality of curved blades to part off tissue cut by the rotating first pair of first and second articulable beaks. Advancing may be performed over a guidewire inserted within the vasculature. The imaging may be performed using optical coherence tomography or, for example, using ultrasound.

The device further may include an independently operable second pair of first and second articulable beaks that may be smaller than the first pair of first and second articulable beaks and the chamber may be further configured to define a central lumen that emerges at a distal end of the chamber. In such a case, the method may further comprise advancing the second pair of first and second articulable beaks through the central lumen past the distal end of the chamber. The method may also comprise coring through tissue disposed distal to the chamber with the second pair of the first and second articulable beaks rotating in an open configuration and parting off the cored tissue by causing the second pair of the first and second articulable beaks to assume a closed configuration. The method may also comprise stabilizing the coring and parting off of the tissue distal to the chamber by controlling inflation of the chamber and of the inflatable support element(s). The method may also further comprise deflating the chamber and advancing the chamber within a cored path created by the second pair of the first and second articulable beaks. The method may also include re-inflating the chamber within the cored path created by the second pair of the first and second articulable beaks. Also, an expandable cuff disposed proximal of the first pair of first and second articulable beaks may also be inflated to provide additional stabilization. The inflatable support element(s) may include a first inflatable support element and a second inflatable support element spaced apart from the first inflatable support element to define a channel therebetween. The method further may include enabling fluid flow from a distal end of the device downstream past a proximal end of the device through the channel. The method may also comprise selectably deforming the chamber against one side of a passageway by inflating the at least one inflatable support element to press against an opposing side of the passageway.

While certain embodiments of the disclosure have been described, these embodiments have been presented by way of example only and are not intended to limit the scope of the disclosure. Indeed, the novel methods, devices and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the figures. Depending on the embodiment, certain steps described in the example above may be removed, and others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

The invention claimed is:

1. A device configured to cut an occlusion within a vasculature, comprising:

an outer flexible tube defining a longitudinal axis;

a rotatable scoopula disposed within the outer flexible tube and defining an open side portion;

an inner sheath disposed within the rotatable scoopula and configured to move parallel to the longitudinal axis;

a first pair of first and second articulable beaks, disposed within the inner sheath and rotatable around the longitudinal axis, the first pair of articulable beaks partially extending into the open side portion of the scoopula, and a second pair of first and second articulable beaks that is smaller than and coaxially disposed relative to the first pair of articulable beaks, the second pair of articulable beaks being configured to advance distally relative to the rotatable scoopula and to cut a pilot hole in the occlusion in the vasculature by selectively assuming an open and an at least partially closed configuration while rotating against the occlusion;

wherein the first pair of articulable beaks are configured to advance over the second pair of articulable beaks and to further cut the occlusion by selectively assuming an open and a at least partially closed configuration while centered on the pilot hole and rotating against the occlusion.

2. The device of claim 1, further comprising an expandable and collapsible chamber that is configured to move parallel to the longitudinal axis and disposed at a distal end of a central tube positioned between the first pair of articu-lable beaks, the chamber being configured to accommodate an imaging device within a volume of fluid contained within the chamber.

3. The device of claim 2, further comprising a plurality of curved blades attached to an outer surface of the chamber, the chamber being configured to advance along and rotate about the longitudinal axis and to widen the pilot hole in the occlusion by selectively expanding or collapsing while cutting the occlusion using the curved blades.

4. The device of claim 2, wherein the second pair of articulable beaks is disposed at a distal end of the chamber.

5. The device of claim 2, wherein the imaging device is one of an optical coherence tomography imaging device and an ultrasound imaging device.

6. The device of claim 2, wherein the expandable and collapsible chamber comprises a surface that defines a central lumen that emerges at a distal end of the chamber.

7. The device of claim 6, wherein the second pair of articulable beaks are configured to be advanced within the central tube, through the central lumen and past the distal end of the chamber.

8. The device of claim 1, further comprising at least one inflatable support element attached to the rotatable scoopula or to the outer flexible tube, the at least one inflatable support element being configured to selectively anchor the device within the vasculature.

9. The device of claim 8, wherein the at least one inflatable support element comprises an expandable cuff attached to the flexible tube, the expandable cuff being configured to selectively enable a blood flow in the vasculature or seal off the blood flow in the vasculature.

10. The device of claim 8, wherein the at least one inflatable support element is attached to an outer surface of the rotatable scoopula and comprises a first inflatable support element and a second inflatable support element spaced apart from the first inflatable support to define a channel therebetween, the channel being configured to selectively enable blood flow therethrough.

* * * * *